United States Patent
Webster et al.

(10) Patent No.: US 9,834,549 B2
(45) Date of Patent: Dec. 5, 2017

(54) 3,3-DISUBSTITUTED-(8-AZA-BICYCLO[3.2.1]OCT-8-YL)-[5-(1H-PYRAZOL-4-YL)-THIOPHEN-3-YL]-METHANONES AS INHIBITORS OF 11 (β)-HSD1

(71) Applicant: The University Of Edinburgh, Edinburgh (GB)

(72) Inventors: Scott Peter Webster, Edinburgh (GB); Jonathan Robert Seckl, Edinburgh (GB); Brian Robert Walker, Edinburgh (GB); Peter Ward, Middlesex (GB); Thomas David Pallin, Harlow (GB); Hazel Joan Dyke, Storrington (GB); Trevor Robert Perrior, Bury St Edmunds (GB)

(73) Assignee: THE UNIVERSITY OF EDINBURGH, Edinburgh (GB)

( * ) Notice: Subject to any disclaimer, the term of this patent is extended or adjusted under 35 U.S.C. 154(b) by 0 days.

(21) Appl. No.: 15/154,254

(22) Filed: May 13, 2016

(65) Prior Publication Data

US 2016/0251346 A1 Sep. 1, 2016

Related U.S. Application Data

(63) Continuation of application No. 13/642,963, filed as application No. PCT/GB2011/000345 on Mar. 10, 2011, now Pat. No. 9,365,564.

(60) Provisional application No. 61/329,453, filed on Apr. 29, 2010.

(51) Int. Cl.
| | |
|---|---|
| *C07D 409/14* | (2006.01) |
| *C07D 451/02* | (2006.01) |
| *C07D 451/04* | (2006.01) |
| *C07D 451/06* | (2006.01) |

(52) U.S. Cl.
CPC ......... *C07D 451/06* (2013.01); *C07D 409/14* (2013.01); *C07D 451/02* (2013.01); *C07D 451/04* (2013.01)

(58) Field of Classification Search
CPC .. C07D 409/14; C07D 451/02; C07D 451/04; C07D 451/06
USPC ....... 514/252.04, 255.05, 256, 304; 544/333, 544/238, 405; 546/125
See application file for complete search history.

(56) References Cited

U.S. PATENT DOCUMENTS

| | | | |
|---|---|---|---|
| 5,087,631 A | 2/1992 | Shaffer et al. | |
| 6,340,678 B1 | 1/2002 | Matsuhisa et al. | |
| 8,299,063 B2 | 10/2012 | Webster et al. | |
| 8,362,008 B2 | 1/2013 | Webster et al. | |
| 8,609,690 B2 | 12/2013 | Eckhardt et al. | |
| 8,614,209 B2 | 12/2013 | Webster et al. | |
| 8,642,621 B2 | 2/2014 | Webster et al. | |
| 9,365,564 B2 | 6/2016 | Webster et al. | |
| 2006/0111366 A1 | 5/2006 | Andersen et al. | |
| 2007/0117800 A1 | 5/2007 | Arnold et al. | |
| 2007/0203154 A1 | 8/2007 | Zhou et al. | |
| 2010/0197662 A1 | 8/2010 | Ogawa | |
| 2010/0267696 A1 | 10/2010 | Webster et al. | |
| 2011/0015178 A1 | 1/2011 | Webster et al. | |

(Continued)

FOREIGN PATENT DOCUMENTS

| | | |
|---|---|---|
| EP | 1889842 A1 | 2/2008 |
| EP | 1894919 A1 | 3/2008 |

(Continued)

OTHER PUBLICATIONS

Thorber "Isosterism and molecular . . . " Chem. Soc. rev. v.8, pp. 563-580 (1979).*
Patani et al. "Bioisosterism . . . " Chem. Rev. 96 pp. 3147-3176 (1996).*
Andrews, R,C., et al., 2003, "Effects of the 11β-hydroxysteroid dehydrogenase inibitor carbenoxolone on insulin sensitivity in men with type 2 diabetes," *J. Clin. Endocrinol Metab.*, vol. 88, pp, 285-291.
Chengzhi et al. 1994 "Synthesis of a Pyrimidine Isostere of the N-Methyl-D-Aspartate Antagnoist SDZ EAB 515" Tetrahedron 50(19)5735-5740.
Christy, C. et al., 2003., "11β-hydroxysteroid dehydrogenase type 2 in mouse aorta; Localization and influence on response to glucocorticoids," *Hypertension*, vol. 42, pp. 580-587.

(Continued)

*Primary Examiner* — Niloofar Rahmani
(74) *Attorney, Agent, or Firm* — Swanson & Bratschun, L.L.C.

(57) ABSTRACT

The present invention pertains generally to the field of therapeutic compounds. More specifically the present invention pertains to certain 3,3-disubstituted-(8-aza-bicyclo [3.2.1]oct-8-yl)-[5-(1H-pyrazol-4-yl)-thiophen-3-yl]-methanone, 3,3-disubstituted-(6-aza-bicyclo[3.1.1]hept-6-yl)-[5-(1H-pyrazol-4-yl)-thiophen-3-yl]-methanone, and 4,4-disubstituted piperidin-1-yl)-[5-(1H-pyrazol-4-yl)-thiophen-3-yl]-methanone compounds of the following formula that, inter alia, inhibit 11β-hydroxysteroid dehydrogenase type 1 (11β-HSD1). The present invention also pertains to pharmaceutical compositions comprising such compounds, and the use of such compounds and compositions, both in vitro and in vivo, to inhibit 11β-hydroxysteroid dehydrogenase type 1; to treat disorders that are ameliorated by the inhibition of 11β-hydroxysteroid dehydrogenase type 1; to treat the metabolic syndrome, which includes disorders such as type 2 diabetes and obesity, and associated disorders including insulin resistance, hypertension, lipid disorders and cardiovascular disorders such as ischaemic (coronary) heart disease; to treat CNS disorders such as mild cognitive impairment and early dementia, including Alzheimer's disease; etc.

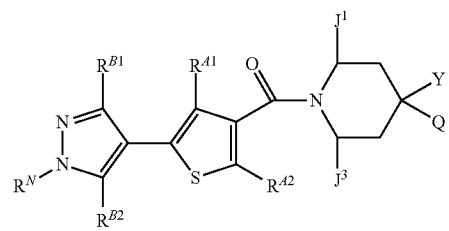

50 Claims, No Drawings

(56) References Cited

U.S. PATENT DOCUMENTS

| | | | |
|---|---|---|---|
| 2012/0095046 | A1 | 4/2012 | Webster et al. |
| 2012/0172393 | A1 | 7/2012 | Webster et al. |
| 2013/0012545 | A1 | 1/2013 | Webster et al. |
| 2013/0123268 | A1 | 5/2013 | Webster et al. |

FOREIGN PATENT DOCUMENTS

| | | | |
|---|---|---|---|
| WO | WO 1998/39325 | A1 | 9/1998 |
| WO | WO 2000/51608 | A1 | 9/2000 |
| WO | WO 2003/044009 | A1 | 5/2003 |
| WO | WO 2004/016617 | A1 | 2/2004 |
| WO | WO 2005/046685 | A1 | 5/2005 |
| WO | WO 2005/047250 | A1 | 5/2005 |
| WO | WO 2005/121145 | A2 | 12/2005 |
| WO | WO 2006/132197 | A1 | 12/2006 |
| WO | WO 2007/053776 | A1 | 5/2007 |
| WO | WO 20071082808 | A2 | 7/2007 |
| WO | WO 2008/011453 | A2 | 1/2008 |
| WO | WO 2008/103185 | | 8/2008 |
| WO | WO 2009/059666 | A1 | 5/2009 |
| WO | WO 2009/074789 | A1 | 6/2009 |
| WO | WO 2009/090239 | A1 | 7/2009 |
| WO | WO 20091112845 | A1 | 9/2009 |
| WO | WO 2010/023161 | A1 | 3/2010 |
| WO | WO 2010/146338 | A1 | 12/2010 |
| WO | WO 2011/033255 | A1 | 3/2011 |
| WO | WO 2011/135276 | A1 | 11/2011 |

OTHER PUBLICATIONS

Cooper, M.S., et al., Sep. 2000, "Expression and functional consequences of 11β-hydroxysteroid dehydrogenase activity in human bone," *Bone*, vol. 27(3), pp. 375-381.
GB Search Report for UK Patent Appln No. 0724251.4, dated Mar. 27, 2008.
GB Search Report for UK Patent Appln No. 0804685.6, dated Jul. 10, 2008.
Gotthardt, H., 1971, "1.3-Dipolare Cycloadditionen Mit 1.3.2-Oxathiazolium-5-oxiden. Ein Neuer Weg in Die 5-Aryl-Isothiazol-Reihe", *Tetrahedron Letters*, No. 17, pp. 1281-1284.
Hadoke, P.W.F., et al., 2001, "Endothelial cell dysfunction in mice after transgenic knockout of type 2, but not type 1, 11β-hydroxysteroid dehydrogenase", *Circulation*, vol. 104, pp. 2832-2837.
Hwang et al., 2001, "4-Hydroxy-6-oxo-6,7-dihydro-thieno[2,3-b]pyrimidine derivatives: synthesis and their biological evaluation for the glycine site acting on the N-methyl-D-aspartate (NMDA) receptor", *Archives of Pharmacol. Research*, vol. 24, No. 4, pp. 270-275.
IPRP for PCT/GB2008/004068, dated Jun. 15, 2010.
IPRP for PCT/GB2009/000686, dated Sep. 14, 2010.
IPRP for PCT/GB2010/001155, dated Dec. 16, 2011.
IPRP for PCT/GB2010/001732, dated Mar. 20, 2012.
IPRP for PCT/GB2011/000345, dated Oct. 30, 2012.
ISR and WOISA for PCT/GB2008/004068, dated Feb. 6, 2009.
ISR and WOISA for PCT/GB2009/000686, dated Jun. 5, 2009.
ISR and WOISA for PCT/GB2010/001155, dated Sep. 28, 2010.
ISR and WOISA for PCT/GB2010/001732, dated Mar. 20, 2012.
ISR and WOISA for PCT/GB2011/000345, dated May 4, 2011.
King, Frank D. "Bioisosteres, Conformational Restriction, and Pro-drugs—Case History: an Example of a Conformational Restriction Approach", Med. Chem. Principle and Practice Chapter 14, p. 206-209 (1994).

Kotelevtsev, Y.V., et al., Dec. 1997, "11β-Hydroxysteroid dehydrogenase type 1 knockout mice show attenuated glucocorticoid inducible responses and resist hyperglycaemia on obesity and stress," *Proc. Natl. Acad. Sci.*, vol. 94, pp. 14924-14929.
Masuzaki, H., et al., 2001, "A Transgenic Model of Visceral Obesity and the Metabolic Syndrome," *Science*, vol. 294, pp. 2166-2170.
Moisan, M.P., et al., 1990, "11β-hydroxysteroid dehydrogenase bioactivity and messenger RNA expression in rat forebrain: localization in hypothalamus, hippocampus, and cortx," *Endocrinology*, vol. 127(3), pp. 1450-1455.
Morton, N.M., et al., Apr. 2004, "Novel adipose tissue-mediated resistance to diet-induced visceral obesity in 11β-hydroxysteroid dehydrogenase type 1 deficient mice," *Diabetes*, vol. 53, pp. 931-938.
Morton, N.M., et al., Nov. 2, 2001, "Improved lipid and lipoprotein profile, hepatic insulin sensitivity, and glucose tolerance in 11β-hydroxysteroid dehydrogenase type 1 null mice," *J. Biol. Chem.*, vol. 276(44), pp. 41293-41300.
Patani, G.A., et al., 1996, "Bioisosterism: A rational approach in drug design", *American Chemical Society*, vol. 96, pp. 3147-3176.
Paterson, J.M., et al., May 4, 2004, "Metabolic syndrome without obesity: hepatic overexpression of 11β- hydroxysteroid dehydrogenase type 1 in transgenic mice," *Proc. Natl. Acad. Sci.*, vol. 101(18), pp. 7088-7093).
Pyrimidines "http://www.makehumans.com/htmx/pyrimidine.php" p. 1-2 (2014).
Rask, E., et al., 2001, "Tissue-specific dysregulation of cortisol metabolism in human obesity," *J. Clin. Endocrinol. Metab.*, vol. 86(3), pp. 1418-1421.
Rauz, S., et al., 2001, "Expression and putative role of 11β-hydroxysteroid dehydrogenase isozymes within the human eye," *Investigative Opthamology & Visual Science*, vol. 42(9), pp. 2037-2042.
Registry No. 717867-57-7, entered STN Jul. 28, 2004.
Registry No. 717867-85-1, entered STN Jul. 28, 2004.
Registry No. 727385-01-5, entered STN Aug. 16, 2004.
Sandeep, T.C., et al., Apr. 27, 2004, "11β-hydroxysteroid dehydrogenase inhibition improves cognitive function in healthy elderly men and type 2 diabetics," *Proc. Natl. Acad. Sci.*, vol. 101(17), pp. 6734-6739.
Seckl, J.R., Walker, B.R., 2001, "11β-Hydroxysteroid dehydrogenase type 1—a tissue specific amplifier of glucocorticoid action," *Endocrinology*, vol. 142(4), pp. 1371-1376.
Small, G.R., et al., Aug. 23, 2005, "Preventing local regeneration of glucocorticoids by 11β-hydroxysteroid dehydrogenase type 1 enhances angiogenesis," *Proc. Natl. Acad. Sci.*, vol. 102(34), pp. 12165-12170.
Stimson, R.H., et al., 2010, "Extra-adrenal cortisol production in obese men with type two diabetes mellitus—how big is the therapeutic target for 11βHSD1 inhibitors?" $92^{nd}$ Annual Meeting of the Endocrine Society, San Diego, USA.
Walker, B.R., et al., 1991, "11β-Hydroxysteroid dehydrogenase in vascular smooth muscle and heart: implications for cadiovascular responses to glucocorticoids," *Endocrinology*, vol. 129(6), pp. 3305-3312.
Walker, B.R., et al., 1995, "Carbenoxolone increases hepatic insulin sensitivity in man: a novel role for 11-oxosteroid reductase in enhancing glucocorticoid receptor activation," *J. Clin. Endocrinol. Metab.*, vol. 80(11), pp. 3155-3139.
Yau, J.L.W., et al., Apr. 10, 2001, "Lack of tissue glucocorticoid reactivation in 11β-hydroxysteroid dehydrogenase type 1 knockout mice ameliorates age-related learning impairments," *Proc. Natl. Acad. Sci.*, vol. 98(8), pp. 4716-4721.

\* cited by examiner

3,3-DISUBSTITUTED-(8-AZA-BICYCLO[3.2.1] OCT-8-YL)-[5-(1H-PYRAZOL-4-YL)- THIOPHEN-3-YL]-METHANONES AS INHIBITORS OF 11 (β)-HSD1

RELATED APPLICATION

This application is a continuation of U.S. application Ser. No. 13/642,963, filed Dec. 29, 2012. U.S. application Ser. No. 13/642,963 is a 35 U.S.C. §371 national phase application of PCT/GB2011/000345, filed Mar. 10, 2011 (WO 2011/135276). PCT/GB2011/000345 claims priority to U.S. provisional patent application No. 61/329,453, filed Apr. 29, 2010. The contents of all of the above-referenced applications are incorporated herein by reference in their entirety.

TECHNICAL FIELD

The present invention pertains generally to the field of therapeutic compounds. More specifically the present invention pertains to certain 3,3-disubstituted-(8-aza-bicyclo [3.2.1]oct-8-yl)-[5-(1H-pyrazol-4-yl)-thiophen-3-yl]- methanone, 3,3-disubstituted-(6-aza-bicyclo[3.1.1]hept-6- yl)-[5-(1H-pyrazol-4-yl)-thiophen-3-yl]-methanone, and 4,4-disubstituted piperidin-1-yl)-[5-(1H-pyrazol-4-yl)-thiophen-3-yl]-methanone compounds that, inter alia, inhibit 11β-hydroxysteroid dehydrogenase type 1 (11β-HSD1). The present invention also pertains to pharmaceutical compositions comprising such compounds, and the use of such compounds and compositions, both in vitro and in vivo, to inhibit 11β-hydroxysteroid dehydrogenase type 1; to treat disorders that are ameliorated by the inhibition of 11β- hydroxysteroid dehydrogenase type 1; to treat the metabolic syndrome, which includes disorders such as type 2 diabetes and obesity, and associated disorders including insulin resistance, hypertension, lipid disorders and cardiovascular disorders such as ischaemic (coronary) heart disease; to treat CNS disorders such as mild cognitive impairment and early dementia, including Alzheimer's disease; etc.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Glucocorticoids (cortisol in man, corticosterone in rodents) are hormones that regulate a range of pathways involved in stress and metabolic signalling. They are antagonists of insulin action and impair insulin-dependent glucose uptake, increase lipolysis, and enhance hepatic gluconeogenesis. These effects are evident in Cushing's syndrome, which is caused by elevated circulating levels of glucocorticoids. The features of Cushing's syndrome are diverse and reflect the tissue distribution of glucocorticoid receptors in the body. They include a cluster of metabolic (central/visceral obesity, insulin resistance, hyperglycaemia, dyslipidaemia) and cardiovascular (hypertension) abnormalities which, when observed in patients without Cushing's syndrome, constitute the metabolic syndrome. These abnormalities confer a substantial risk of cardiovascular disease. In addition, Cushing's syndrome is associated with neuropsychiatric manifestations including depression and cognitive impairment. The features of Cushing's syndrome are reversible upon removal of the cause of glucocorticoid excess.

It is recognised that glucocorticoid activity is controlled at the tissue level by the intracellular conversion of active cortisol and inactive cortisone by 11β-hydroxysteroid dehydrogenases (see, e.g., Seckl et al., 2001). These enzymes exist in two distinct isoforms. 11β-HSD1, which catalyses the reaction that activates cortisone, is expressed in liver, adipose tissue, brain, skeletal muscle, vascular smooth muscle and other organs, while, 11β-HSD2, which inactivates cortisol, is predominantly expressed in the kidney. Pharmacological inhibition of 11β-HSD1 in rat and man with carbenoxolone (see, e.g., Walker et al., 1995), and transgenic knockout in mice (see, e.g., Kotelevtsev et al., 1997), results in enhanced hepatic insulin sensitivity and reduced gluconeogenesis and glycogenolysis, suggesting that 11β-HSD1 inhibition will be a useful treatment in type 2 diabetes and other insulin resistance syndromes. Furthermore, mice lacking 11β-HSD1 possess low triglycerides, increased HDL cholesterol, and increased apo-lipoprotein A-I levels (see, e.g., Morton et al., 2001), suggesting that inhibitors of 11β-HSD1 may be of utility in the treatment of atherosclerosis.

The link between 11β-HSD1 and the metabolic syndrome has been strengthened by studies in transgenic mice and man. 11β-HSD1 knockout mice on two different genetic backgrounds are protected from dietary obesity (see, e.g., Morton et al., 2004), while administration of carbenoxolone to patients with type 2 diabetes enhances insulin sensitivity (see, e.g., Andrews et al., 2003). Although liver 11β-HSD1 exerts a major influence upon metabolic disease it has become apparent that 11β-HSD1 in the adipose tissue is also important in metabolic disease. Mice with transgenic overexpression of 11β-HSD1 in adipose tissue (see, e.g. Masuzaki et al., 2001) have a more profound metabolic syndrome and obesity than mice with overexpression in liver (see, e.g., Paterson et al., 2004). In obese humans, 11β-HSD1 activity is increased in adipose tissue, but enzyme activity is decreased in the liver (see, e.g., Rask et al., 2001). In obese humans with type 2 diabetes, 11β-HSD1 activity is similarly increased in adipose tissue and sustained in the liver (see, e.g., Stimson et al., 2010).

In the CNS, 11β-HSD1 is highly expressed in regions important for cognition such as hippocampus, frontal cortex, and cerebellum (see, e.g., Moisan et al., 1990). Elevated cortisol is associated with cognitive dysfunction, and glucocorticoids have a range of neurotoxic effects. 11β-HSD1 knockout mice are protected against age-related cognitive dysfunction (see, e.g., Yau et al., 2001), while administration of the 11β-HSD inhibitor carbenoxolone has been shown to enhance cognitive function in elderly men and type 2 diabetics who have a selective impairment in verbal memory (see, e.g., Sandeep et al., 2004). Thus, 11β-HSD1 inhibitors are of potential therapeutic utility in the treatment of diseases such as Alzheimer's Disease, which are characterised by cognitive impairment.

The isozymes of 11β-HSD are also expressed in the blood vessel wall (see, e.g., Walker et al., 1991; Christy et al, 2003). 11β-HSD1 is expressed in vascular smooth muscle, while 11β-HSD2 is expressed in endothelial cells where it modulates endothelial-dependent vasodilation (see, e.g., Hadoke et al., 2001). 11β-HSD1 knockout mice have normal vascular function, but they exhibit enhanced angiogenesis in response to inflammation or ischaemia (see, e.g., Small et al., 2005) and reduced neointimal proliferation following intra-luminal arterial injury or angioplasty. This offers therapeutic potential in the treatment of myocardial infarction, since inhibition of 11β-HSD1 may enhance revascularisation of ischaemic tissues, and in occlusive atherosclerotic vascular disease.

Studies have shown that 11β-HSD1 affects intraocular pressure in man (see, e.g., Rauz et al., 2001). Inhibition of 11β-HSD1 may be useful in reducing intraocular pressure in the treatment of glaucoma.

Glucocorticoids are involved in the regulation of bone formation and skeletal development. Treatment of healthy volunteers with carbenoxolone led to a decrease in bone resorption markers suggesting that 11β-HSD1 plays a role in bone resorption (see, e.g., Cooper et al., 2000). 11β-HSD1 inhibitors could be used as protective agents in the treatment of osteoporosis.

Certain compounds that inhibit 11β-hydroxysteroid dehydrogenase type 1 (11β-HSD1) that are useful in the treatment, control, and/or prevention of disorders (e.g., diseases) that are responsive to the inhibition of 11β-HSD1 are described in international (PCT) patent application number PCT/GB2009/000686 filed 13 Mar. 2009 (published as WO 2009/112845 on 17 Sep. 2009).

Certain compounds of the following formula which allegedly inhibit 11β-HSD1, and allegedly are useful in the treatment and prevention of diseases such as metabolic diseases, in particular, diabetes type 2, obesity, and dyslipidemia, are described in WO 2010/023161 A1 (published on 4 Mar. 2010).

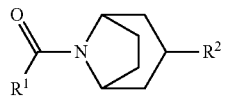

The inventors have discovered an especially preferred class of compounds, which inhibit 11β-hydroxysteroid dehydrogenase type 1 (11β-HSD1), and which additionally have improved pharmacokinetic and/or microsomal stability properties, and which are useful in the treatment, control, and/or prevention of disorders (e.g., diseases) that are responsive to the inhibition of 11β-HSD1.

SUMMARY OF THE INVENTION

One aspect of the invention pertains to certain 3,3-disubstituted-(8-aza-bicyclo[3.2.1]oct-8-yl)-[5-(1H-pyrazol-4-yl)-thiophen-3-yl]-methanone, 3,3-disubstituted-(6-aza-bicyclo[3.1.1]hept-6-yl)-[5-(1H-pyrazol-4-yl)-thiophen-3-yl]-methanone, and 4,4-disubstituted piperidin-1-yl)-[5-(1H-pyrazol-4-yl)-thiophen-3-yl]-methanone compounds (referred to herein as DSPT compounds), as described herein.

Another aspect of the invention pertains to a composition (e.g., a pharmaceutical composition) comprising a DSPT compound, as described herein, and a pharmaceutically acceptable carrier or diluent.

Another aspect of the invention pertains to a method of preparing a composition (e.g., a pharmaceutical composition) comprising the step of admixing a DSPT compound, as described herein, and a pharmaceutically acceptable carrier or diluent.

Another aspect of the present invention pertains to a method of inhibiting 11β-hydroxysteroid dehydrogenase type 1 (11β-HSD1) function (e.g., in a cell), in vitro or in vivo, comprising contacting the cell with an effective amount of a DSPT compound, as described herein.

Another aspect of the present invention pertains to a method of treatment comprising administering to a subject in need of treatment a therapeutically-effective amount of a DSPT compound, as described herein, preferably in the form of a pharmaceutical composition.

Another aspect of the present invention pertains to a DSPT compound as described herein for use in a method of treatment of the human or animal body by therapy.

Another aspect of the present invention pertains to use of a DSPT compound, as described herein, in the manufacture of a medicament for use in treatment.

In one embodiment, the treatment is treatment or prevention of a disorder (e.g., a disease) that is ameliorated by the inhibition of 11β-hydroxysteroid dehydrogenase type 1 (11β-HSD1).

In one embodiment, the treatment is treatment or prevention of metabolic syndrome, which includes conditions such as type 2 diabetes and obesity, and associated disorders including insulin resistance, hypertension, lipid disorders and cardiovascular disorders such as ischaemic (coronary) heart disease.

In one embodiment, the treatment is treatment or prevention of a CNS disorder (e.g., a CNS disease) such as mild cognitive impairment and early dementia, including Alzheimer's disease.

Another aspect of the present invention pertains to a kit comprising (a) a DSPT compound, as described herein, preferably provided as a pharmaceutical composition and in a suitable container and/or with suitable packaging; and (b) instructions for use, for example, written instructions on how to administer the compound.

Another aspect of the present invention pertains to a DSPT compound obtainable by a method of synthesis as described herein, or a method comprising a method of synthesis as described herein.

Another aspect of the present invention pertains to a DSPT compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

One aspect of the present invention relates to certain 3,3-disubstituted-(8-aza-bicyclo[3.2.1]oct-8-yl)-[5-(1H-pyrazol-4-yl)-thiophen-3-yl]methanone, 3,3-disubstituted-(6-aza-bicyclo[3.1.1]hept-6-yl)-[5-(1H-pyrazol-4-yl)-thiophen-3-yl]-methanone, and 4,4-disubstituted piperidin-1-yl)-[5-(1H-pyrazol-4-yl)-thiophen-3-yl]-methanone compounds (for convenience, collectively referred to herein as "DSPT compounds"), which are related to the following compounds:

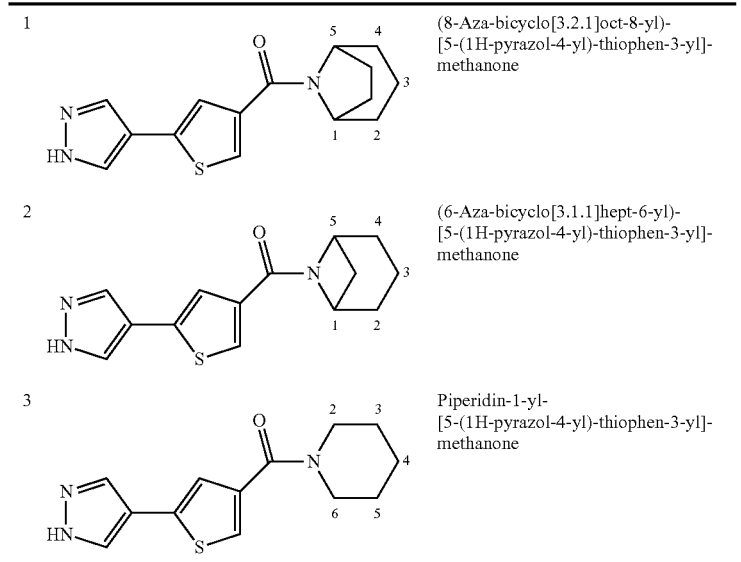

The compounds of the present invention are characterised, at least in part, by the presence of two substituents, Y and Q, at the position para to the piperidine nitrogen atom, as illustrated below.

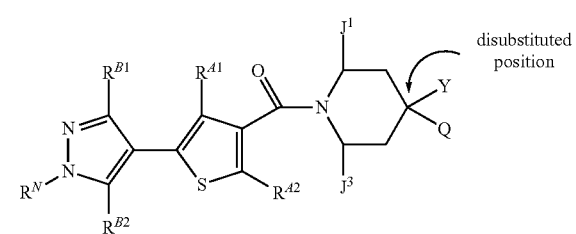

Some embodiments of the invention include the following:

(1) A compound selected from compounds of the following formula, and pharmaceutically acceptable salts, hydrates, and solvates thereof:

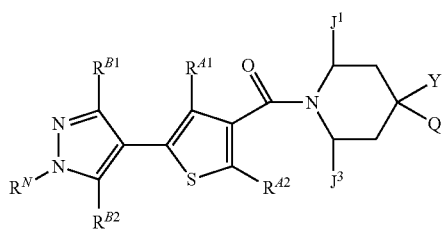

wherein:
-$J^1$ and -$J^3$ taken together form —$CH_2CH_2$— or —$CH_2$—; or
-$J^1$ is —H and -$J^3$ is —H;
and wherein:
-Q is independently $C_{5-10}$heteroaryl, and has n substituents —$R^F$;
wherein:
n is independently 0, 1, 2, or 3;
and wherein:
each —$R^F$ is independently —$R^Z$, —F, —Cl, —$CF_3$, —OH, —$OR^Z$, —$OCF_3$, —CN, —$NH_2$, —$NHR^{ZZ}$, —$NR^{ZZ}_2$, azetidino, pyrrolidino, piperidino, piperazino, morpholino, or azepino;
wherein each —$R^Z$ is independently saturated aliphatic $C_{1-6}$ alkyl or saturated $C_{3-6}$ cycloalkyl, and is optionally substituted with one or more substituents selected from —F, —OH, —$OR^{ZZ}$, —$OCH_2F$, —$OCHF_2$, and —$OCF_3$;
wherein each —$R^{ZZ}$ is independently saturated aliphatic $C_{1-4}$alkyl; and
wherein each azetidino, pyrrolidino, piperidino, piperazino, morpholino, and azepino is optionally substituted with one or more saturated aliphatic $C_{1-4}$alkyl groups;
and wherein:
—Y is independently —$Y^1$, —$Y^2$, —$Y^3$, —$Y^4$, —$Y^5$, —$Y^6$, or —$Y^7$;
—$Y^1$ is independently —OH;
—$Y^2$ is independently —$Y^{2A}$, —$Y^{2B}$, —$Y^{2C}$, or —$Y^{2D}$;
—$Y^3$ is independently —$Y^{3A}$, —$Y^{3B}$, —$Y^{3C}$, or —$Y^{3D}$;

—$Y^4$ is independently —F or —Cl;
—$Y^5$ is independently —CN;
—$Y^6$ is independently —NH$_2$;
—$Y^7$ is independently —$Y^{7A}$, —$Y^{7B}$, or —$Y^{7C}$;
wherein:
—$Y^{2A}$ is independently —OR$^{YA}$;
—$Y^{2B}$ is independently —OR$^{YB}$;
—$Y^{2C}$ is independently —OR$^{YC}$;
—$Y^{2D}$ is independently —OR$^{YD}$;
—$Y^{3A}$ is independently —R$^{YA}$;
—$Y^{3B}$ is independently —R$^{YB}$;
—$Y^{3C}$ is independently —R$^{YC}$;
—$Y^{3C}$ is independently —R$^{YD}$;
—$Y^{7A}$ is independently —NHR$^{YA}$, —NHR$^{YB}$, —NHR$^{YC}$, or —NHR$^{YD}$,
—$Y^{7B}$ is independently —NR$^{YA}_2$, —NR$^{YB}_2$, —NR$^{YC}_2$, —NR$^{YD}_2$, —NR$^{YA}$R$^{YB}$, —NR$^{YA}$R$^{YC}$, —NR$^{YA}$R$^{YD}$, —NR$^{YB}$R$^{YC}$, —NR$^{YB}$R$^{YD}$, or —NR$^{YC}$R$^{YD}$;
—$Y^{7C}$ is independently azetidino, pyrrolidino, piperidino, piperazino, morpholino, or azepino, and is optionally substituted with one or more groups —$Y^{7X}$, wherein each —$Y^{7X}$ is independently saturated aliphatic C$_{1-4}$alkyl;
wherein:
each —R$^{YA}$ is independently saturated aliphatic C$_{1-6}$alkyl;
each —R$^{YB}$ is independently saturated aliphatic halo-C$_{1-6}$alkyl;
each —R$^{YC}$ is independently saturated aliphatic hydroxy-C$_{1-6}$alkyl;
each —R$^{YD}$ is independently saturated C$_{3-6}$cycloalkyl;
and wherein:
—R$^{A1}$ is independently —H or —R$^{AA}$;
—R$^{A2}$ is independently —H or —R$^{AA}$;
wherein:
each —R$^{AA}$ is independently —R$^{AA1}$, —R$^{AA2}$, —R$^{AA3}$;
wherein:
each —R$^{AA1}$ is independently saturated aliphatic C$_{1-4}$alkyl, and is optionally substituted with one or more groups —F;
each —R$^{AA2}$ is independently —F or —Cl;
each —R$^{AA3}$ is independently —CN;
and wherein:
—R$^{B1}$ is independently —H or —R$^{BB}$;
—R$^{B2}$ is independently —H or —R$^{BB}$;
wherein:
each —R$^{BB}$ is independently —R$^{BB1}$, —R$^{BB2}$, or —R$^{BB3}$;
wherein:
each —R$^{BB1}$ is independently saturated aliphatic C$_{1-4}$alkyl, and is optionally substituted with one or more groups —F;
each —R$^{BB2}$ is independently —F or —Cl;
each —R$^{BB3}$ is independently —CN;
and wherein:
—R$^N$ is independently —H or —R$^{NN}$;
—R$^{NN}$ is independently saturated aliphatic C$_{1-4}$alkyl.

For the avoidance of doubt, it is not intended that the pyrazole ring (shown on the far left of the above formula) is fused to any other rings. For example, it is not intended that —R$^N$ and —R$^{B2}$, together with the atoms to which they are attached, form a ring.

For the avoidance of doubt, it is not intended that the thienyl ring (shown middle of the above formula) is fused to any other rings. For example, it is not intended that —R$^{A1}$ and —R$^{B1}$, together with the atoms to which they are attached, form a ring.

For the avoidance of doubt, it is not intended that the piperidine ring or 8-aza-bicyclo[3.2.1]oct-8-yl ring or 6-aza-bicyclo[3.1.1]hept-6-yl ring (shown at the far right of the above formula) is fused to any other rings. For example, it is not intended that -J$^1$ and —Y, together with the atoms to which they are attached, form a ring.

The term "halo-C$_{1-6}$alkyl" as used herein refers to a C$_{1-6}$alkyl that bears one or more halo groups, e.g., —F, —Cl, —Br, —I, as in, for example, —CF$_3$ and —CH$_2$CF$_3$.

The term "hydroxy-C$_{1-6}$alkyl" as used herein refers to a C$_{1-6}$alkyl that bears one or more hydroxyl groups, i.e., —OH, as in, for example, —CH$_2$OH.

The index "C$_{5-10}$" in the term "C$_{5-10}$heteroaryl" refers the number (i.e., 5 to 10) of aromatic ring atoms, whether carbon or a heteroatom, that form the ring structure of the heteroaryl group. In this way, pyrazolyl is an example of C$_5$heteroaryl; pyridyl is an example of C$_6$heteroaryl; benzothiazolyl is an example of C$_9$heteroaryl; and quinolinyl is an example of C$_{10}$heteroaryl.

The Groups -J$^1$ and -J$^3$ (2) A compound according to (1), wherein -J$^1$ and -J$^3$ taken together form —CH$_2$CH$_2$— or —CH$_2$—.

(3) A compound according to (1), wherein -J$^1$ and -J$^3$ taken together form —CH$_2$CH$_2$—.

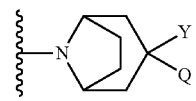

(4) A compound according to (1), wherein -J$^1$ and -J$^3$ taken together form —CH$_2$—.

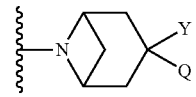

(5) A compound according to (1), wherein -J$^1$ is —H and -J$^3$ is —H.

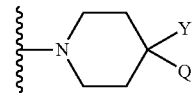

The Group -Q (6) A compound according to any one of (1) to (5), wherein -Q is independently C$_{5-10}$heteroaryl, and has n substituents —R$^F$.

(7) A compound according to any one of (1) to (5), wherein -Q is independently furanyl, thienyl, pyrrolyl, oxazolyl, thiazolyl, imidazolyl, isoxazolyl, isothiazolyl, pyrazolyl, furazanyl, [1,3,4]oxadiazolyl, [1,2,4]oxadiazolyl, [1,2,5]thiadiazolyl, [1,3,4]thiadiazolyl, [1,2,4]thiadiazolyl, 2H-[1,2,3]triazolyl, 4H-[1,2,4]triazolyl, 1H-[1,2,4]triazolyl, pyridyl, pyrimidinyl, pyridazinyl, pyrazinyl, [1,3,5]triazinyl, [1,2,3]triazinyl, [1,2,4]triazinyl, benzofuranyl, benzo[b]thienyl, indolyl, benzooxazolyl, benzothiazolyl, benzoimidazolyl, benzoisoxazolyl, benzoisothiazolyl, indazolyl, quinolinyl, or isoquinolinyl; and has n substituents —R$^F$.

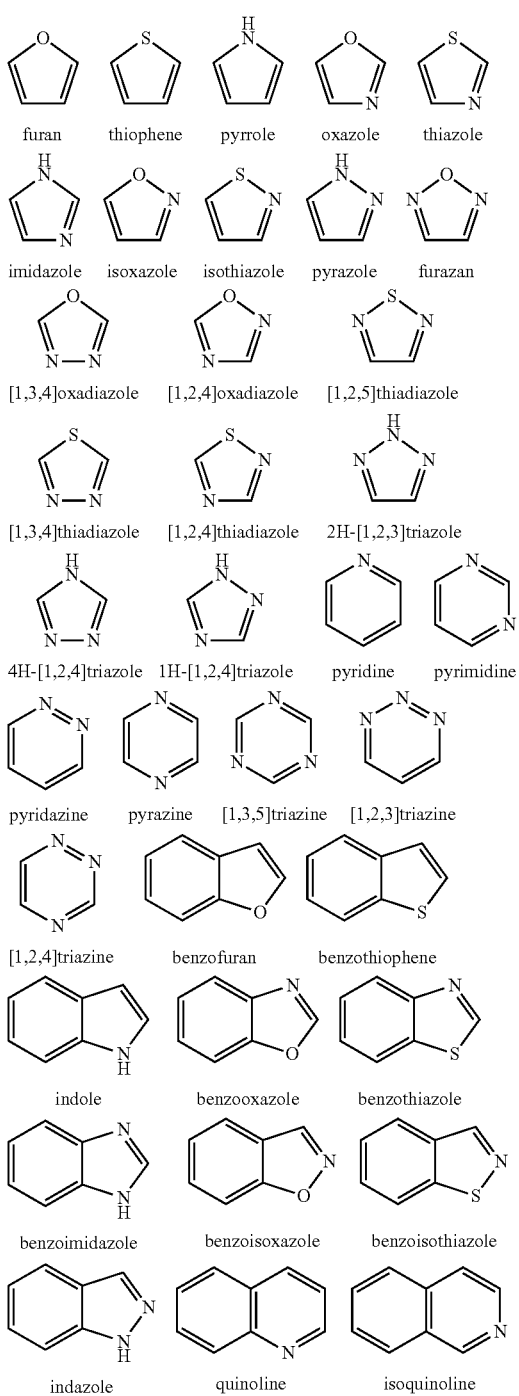

(8) A compound according to any one of (1) to (5), wherein -Q is independently furanyl, thienyl, pyrrolyl, imidazolyl, pyrazolyl, oxazolyl, isoxazolyl, thiazolyl, isothiazolyl, pyridyl, pyrimidinyl, pyridazinyl, pyrazinyl, benzofuranyl, benzo[b]thienyl, indolyl, benzooxazolyl, benzothiazolyl, benzoimidazolyl, benzoisoxazolyl, benzoisothiazolyl, or indazolyl; and has n substituents —$R^F$.

(9) A compound according to any one of (1) to (5), wherein -Q is independently imidazolyl, pyrazolyl, oxazolyl, thiazolyl, pyridyl, pyrimidinyl, pyridazinyl, pyrazinyl, or benzothiazolyl; and has n substituents —$R^F$.

(10) A compound according to any one of (1) to (5), wherein -Q is independently $C_{5-6}$heteroaryl, and has n substituents —$R^F$.

(11) A compound according to any one of (1) to (5), wherein -Q is independently furanyl, thienyl, pyrrolyl, imidazolyl, pyrazolyl, oxazolyl, isoxazolyl, thiazolyl, isothiazolyl, pyridyl, pyrimidinyl, pyridazinyl, or pyrazinyl; and has n substituents —$R^F$.

(12) A compound according to any one of (1) to (5), wherein -Q is independently imidazolyl, pyrazolyl, oxazolyl, thiazolyl, pyridyl, pyrimidinyl, pyridazinyl, or pyrazinyl; and has n substituents —$R^F$.

(13) A compound according to any one of (1) to (5), wherein -Q is independently pyridyl, pyrimidinyl, pyridazinyl, or pyrazinyl; and has n substituents —$R^F$.

(14) A compound according to any one of (1) to (5), wherein -Q is independently pyridyl or pyrimidinyl; and has n substituents —$R^F$.

(15) A compound according to any one of (1) to (5), wherein -Q is independently pyridyl; and has n substituents —$R^F$.

(16) A compound according to any one of (1) to (5), wherein -Q is independently pyrid-2-yl; and has n substituents —$R^F$.

(17) A compound according to any one of (1) to (5), wherein -Q is independently pyrid-3-yl; and has n substituents —$R^F$.

(18) A compound according to any one of (1) to (5), wherein -Q is independently pyrid-4-yl; and has n substituents —$R^F$.

(19) A compound according to any one of (1) to (5), wherein -Q is independently pyrimidinyl; and has n substituents —$R^F$.

(20) A compound according to any one of (1) to (5), wherein -Q is independently pyrimidin-2-yl; and has n substituents —$R^F$.

(21) A compound according to any one of (1) to (5), wherein -Q is independently pyrimidin-4-yl; and has n substituents —$R^F$.

(22) A compound according to any one of (1) to (5), wherein -Q is independently pyrimidin-5-yl; and has n substituents —$R^F$.

(23) A compound according to any one of (1) to (5), wherein -Q is independently pyridazinyl, and has n substituents —$R^F$.

(24) A compound according to any one of (1) to (5), wherein -Q is independently pyridazin-3-yl, and has n substituents —$R^F$.

(25) A compound according to any one of (1) to (5), wherein -Q is independently pyridazin-4-yl, and has n substituents —$R^F$.

(26) A compound according to any one of (1) to (5), wherein -Q is independently pyrazinyl, and has n substituents —$R^F$.

(27) A compound according to any one of (1) to (5), wherein -Q is independently pyrazin-2-yl; and has n substituents —$R^F$.

(28) A compound according to any one of (1) to (5), wherein -Q is independently imidazolyl, pyrazolyl, oxazolyl, or thiazolyl; and has n substituents —$R^F$.

(29) A compound according to any one of (1) to (5), wherein -Q is independently thiazolyl; and has n substituents —$R^F$.

(30) A compound according to any one of (1) to (5), wherein -Q is independently thiazol-2-yl; and has n substituents —$R^F$.

(31) A compound according to any one of (1) to (5), wherein -Q is independently thiazol-4-yl; and has n substituents —$R^F$.

(32) A compound according to any one of (1) to (5), wherein -Q is independently thiazol-5-yl; and has n substituents —$R^F$.

(33) A compound according to any one of (1) to (5), wherein -Q is independently imidazolyl, and has n substituents —$R^F$.

(34) A compound according to any one of (1) to (5), wherein -Q is independently imidazol-2-yl, and has n substituents —$R^F$.

(35) A compound according to any one of (1) to (5), wherein -Q is independently imidazol-4-yl, and has n substituents —$R^F$.

(36) A compound according to any one of (1) to (5), wherein -Q is independently imidazol-5-yl, and has n substituents —$R^F$.

(37) A compound according to any one of (1) to (5), wherein -Q is independently pyrazolyl, and has n substituents —$R^F$.

(38) A compound according to any one of (1) to (5), wherein -Q is independently pyrazol-3-yl, and has n substituents —$R^F$.

(39) A compound according to any one of (1) to (5), wherein -Q is independently pyrazol-4-yl, and has n substituents —$R^F$.

(40) A compound according to any one of (1) to (5), wherein -Q is independently pyrazol-5-yl, and has n substituents —$R^F$.

(41) A compound according to any one of (1) to (5), wherein -Q is independently oxazolyl, and has n substituents —$R^F$.

(42) A compound according to any one of (1) to (5), wherein -Q is independently oxazol-2-yl, and has n substituents —$R^F$.

(43) A compound according to any one of (1) to (5), wherein -Q is independently oxazol-4-yl, and has n substituents —$R^F$.

(44) A compound according to any one of (1) to (5), wherein -Q is independently oxazol-5-yl, and has n substituents —$R^F$.

(45) A compound according to any one of (1) to (5), wherein -Q is independently benzothiazolyl, and has n substituents —$R^F$.

(46) A compound according to any one of (1) to (5), wherein -Q is independently benzothiazol-2-yl, and has n substituents —$R^F$.

The Index n

(47) A compound according to any one of (1) to (46), wherein n is independently 0, 1, or 2.

(48) A compound according to any one of (1) to (46), wherein n is independently 0 or 1.

(49) A compound according to any one of (1) to (46), wherein n is independently 1, 2, or 3.

(50) A compound according to any one of (1) to (46), wherein n is independently 1 or 2.

(51) A compound according to any one of (1) to (46), wherein n is independently 0.

(52) A compound according to any one of (1) to (46), wherein n is independently 1.

(53) A compound according to any one of (1) to (46), wherein n is independently 2.

(54) A compound according to any one of (1) to (46), wherein n is independently 3.

The Group —$R^F$

(55) A compound according to any one of (1) to (54), wherein each —$R^F$, if present, is independently —$R^Z$, —F, —Cl, —$CF_3$, —OH, —$OR^Z$, —$OCF_3$, —$NH_2$, —$NHR^{ZZ}$, —$NR^{ZZ}_2$, azetidino, pyrrolidino, piperidino, piperazino, morpholino, or azepino;
  wherein each azetidino, pyrrolidino, piperidino, piperazino, morpholino, and azepino is optionally substituted with one or more saturated aliphatic $C_{1-4}$alkyl groups.

(56) A compound according to any one of (1) to (54), wherein each —$R^F$, if present, is independently —$R^Z$, —F, —Cl, —$CF_3$, —OH, —$OR^Z$, —$OCF_3$, —$NH_2$, —$NHR^{ZZ}$, —$NR^{ZZ}_2$, azetidino, pyrrolidino, piperidino, piperazino, morpholino, or azepino;
  wherein each azetidino, pyrrolidino, piperidino, piperazino, morpholino, and azepino is optionally substituted with one or more saturated aliphatic $C_{1-4}$alkyl groups.

(57) A compound according to any one of (1) to (54), wherein each —$R^F$, if present, is independently —$R^Z$, —F, —Cl, —$CF_3$, —OH, —$OR^Z$, —$OCF_3$, —$NH_2$, —$NHR^{ZZ}$, —$NR^{ZZ}_2$, pyrrolidino, piperidino, piperazino, or morpholino;
  wherein each pyrrolidino, piperidino, piperazino, and morpholino is optionally substituted with one or more saturated aliphatic $C_{1-4}$alkyl groups.

(58) A compound according to any one of (1) to (54), wherein each —$R^F$, if present, is independently —$R^Z$, —F, —Cl, —$CF_3$, —OH, —$OR^Z$, —$OCF_3$, —$NH_2$, —$NHR^{ZZ}$, or —$NR^{ZZ}_2$.

The Group —$R^Z$

(59) A compound according to any one of (1) to (58), wherein each —$R^Z$, if present, is independently saturated aliphatic $C_{1-6}$alkyl, and is optionally substituted with one or more substituents selected from —F, —OH, —$OR^{ZZ}$, —$OCH_2F$, —$OCHF_2$, and —$OCF_3$.

(60) A compound according to any one of (1) to (58), wherein each —$R^Z$, if present, is independently saturated aliphatic $C_{1-4}$alkyl or saturated $C_{3-4}$cycloalkyl, and is optionally substituted with one or more substituents selected from —F, —OH, —$OR^{ZZ}$, —$OCH_2F$, —$OCHF_2$, and —$OCF_3$.

(61) A compound according to any one of (1) to (58), wherein each —$R^Z$, if present, is independently saturated aliphatic $C_{1-4}$alkyl, and is optionally substituted with one or more substituents selected from —F, —OH, —$OR^{ZZ}$, —$OCH_2F$, —$OCHF_2$, and —$OCF_3$.

(62) A compound according to any one of (1) to (58), wherein each —$R^Z$, if present, is independently saturated aliphatic $C_{1-6}$alkyl, and is optionally substituted with one or more substituents selected from —F, —OH, and —$OR^{ZZ}$.

(63) A compound according to any one of (1) to (58), wherein each —$R^Z$, if present, is independently saturated aliphatic $C_{1-4}$alkyl or saturated $C_{3-4}$cycloalkyl, and is optionally substituted with one or more substituents selected from —F, —OH, and —$OR^{ZZ}$.

(64) A compound according to any one of (1) to (58), wherein each —$R^Z$, if present, is independently saturated aliphatic $C_{1-4}$alkyl, and is optionally substituted with one or more substituents selected from —F, —OH, and —$OR^{ZZ}$.

(65) A compound according to any one of (1) to (58), wherein each —$R^Z$, if present, is independently unsubstituted saturated aliphatic $C_{1-6}$alkyl or unsubstituted saturated $C_{3-6}$cycloalkyl.

(66) A compound according to any one of (1) to (58), wherein each —$R^Z$, if present, is independently unsubstituted saturated aliphatic $C_{1-6}$alkyl.

(67) A compound according to any one of (1) to (58), wherein each —$R^Z$, if present, is independently unsubstituted saturated aliphatic $C_{1-4}$alkyl or unsubstituted saturated $C_{3-4}$cycloalkyl.

(68) A compound according to any one of (1) to (58), wherein each —$R^Z$, if present, is independently unsubstituted saturated aliphatic $C_{1-4}$alkyl.

(69) A compound according to any one of (1) to (58), wherein each —$R^Z$, if present, is independently -Me, -Et, -nPr, -iPr, -nBu, -iBu, -tBu, cyclopropyl, or cyclobutyl.

(70) A compound according to any one of (1) to (58), wherein each —$R^Z$, if present, is independently -Me, -Et, -nPr, -iPr, -nBu, -iBu, -tBu, or cyclopropyl.

(71) A compound according to any one of (1) to (58), wherein each —$R^Z$, if present, is independently -Me, -Et, -nPr, -iPr, -nBu, -iBu, or -tBu.

(72) A compound according to any one of (1) to (58), wherein each —$R^Z$, if present, is independently -Me or -Et.

The Group —$R^{ZZ}$

(73) A compound according to any one of (1) to (72), wherein each —$R^{ZZ}$, if present, is independently -Me, -Et, -nPr, -iPr, -nBu, -iBu, or -tBu.

(74) A compound according to any one of (1) to (72), wherein each —$R^{ZZ}$, if present, is independently -Me or -Et.

(75) A compound according to any one of (1) to (72), wherein each —$R^{ZZ}$, if present, is independently -Me.

The Group —$R^F$: Some Preferred Groups

(76) A compound according to any one of (1) to (54), wherein each —$R^F$, if present, is independently -Me, -Et, cyclopropyl, —F, —Cl, —$CF_3$, —$CHF_2$, —$CH_2F$, —OH, —OMe, —OEt, —$OCF_3$, —$OCHF_2$, —$OCH_2F$, —$NH_2$, —NHMe, —NHEt, —$NMe_2$, —$NEt_2$, or —NMeEt.

(77) A compound according to any one of (1) to (54), wherein each —$R^F$, if present, is independently -Me, -Et, —F, —Cl, —$CF_3$, —OH, —OMe, —$OCF_3$, —$NH_2$, —NHMe, or —$NMe_2$.

(78) A compound according to any one of (1) to (54), wherein each —$R^F$, if present, is independently -Me, —F, —Cl, —$CF_3$, —OMe, —$OCF_3$, or —$NMe_2$.

The Group —Y

(79) A compound according to any one of (1) to (78), wherein —Y is independently —$Y^1$, —$Y^2$, —$Y^3$, —$Y^4$, or —$Y^5$.

(80) A compound according to any one of (1) to (78), wherein —Y is independently —$Y^1$, —$Y^2$, —$Y^3$, or —$Y^4$.

(81) A compound according to any one of (1) to (78), wherein —Y is independently —$Y^1$, —$Y^2$, or —$Y^3$.

(82) A compound according to any one of (1) to (78), wherein —Y is independently —$Y^1$ or —$Y^2$.

(83) A compound according to any one of (1) to (78), wherein —Y is independently —$Y^1$ or —$Y^3$.

(84) A compound according to any one of (1) to (78), wherein —Y is independently —$Y^1$.

(85) A compound according to any one of (1) to (78), wherein —Y is independently —$Y^2$.

(86) A compound according to any one of (1) to (78), wherein —Y is independently —$Y^3$.

(87) A compound according to any one of (1) to (78), wherein —Y is independently —$Y^4$.

(88) A compound according to any one of (1) to (78), wherein —Y is independently —$Y^5$.

(89) A compound according to any one of (1) to (78), wherein —Y is independently —$Y^6$ or —$Y^7$.

(90) A compound according to any one of (1) to (78), wherein —Y is independently —$Y^6$.

(91) A compound according to any one of (1) to (78), wherein —Y is independently —$Y^7$.

The Group —$Y^2$

(92) A compound according to any one of (1) to (91), wherein —$Y^2$, if present, is independently —$Y^{2A}$, —$Y^{2B}$, or —$Y^{2C}$.

(93) A compound according to any one of (1) to (91), wherein —$Y^2$, if present, is independently —$Y^{2A}$ or —$Y^{2B}$.

(94) A compound according to any one of (1) to (91), wherein —$Y^2$, if present, is independently —$Y^{2A}$.

(95) A compound according to any one of (1) to (91), wherein —$Y^2$, if present, is independently —$Y^{2B}$.

(96) A compound according to any one of (1) to (91), wherein —$Y^2$, if present, is independently —$Y^{2C}$.

(97) A compound according to any one of (1) to (91), wherein —$Y^2$, if present, is independently —$Y^{2D}$.

The Group —$Y^3$

(98) A compound according to any one of (1) to (97), wherein —$Y^3$, if present, is independently —$Y^{3A}$, —$Y^{3B}$, or —$Y^3C$

(99) A compound according to any one of (1) to (97), wherein —$Y^3$, if present, is independently —$Y^{3A}$ or —$Y^{3B}$.

(100) A compound according to any one of (1) to (97), wherein —$Y^3$, if present, is independently —$Y^{3A}$ (101) A compound according to any one of (1) to (97), wherein —$Y^3$, if present, is independently —$Y^{3B}$.

(102) A compound according to any one of (1) to (97), wherein —$Y^3$, if present, is independently —$Y^{3C}$.

(103) A compound according to any one of (1) to (97), wherein —$Y^3$, if present, is independently —$Y^{3D}$ The Group —$Y^4$ (104) A compound according to any one of (1) to (103), wherein —$Y^4$, if present, is independently —F.

(105) A compound according to any one of (1) to (103), wherein —$Y^4$, if present, is independently —Cl.

The Group —$Y^7$ (106) A compound according to any one of (1) to (105), wherein —$Y^7$, if present, is independently —$Y^{7A}$ or —$Y^{7B}$.

(107) A compound according to any one of (1) to (105), wherein —$Y^7$, if present, is independently —$Y^{7A}$.

(108) A compound according to any one of (1) to (105), wherein —$Y^7$, if present, is independently —$Y^{7B}$ (109) A compound according to any one of (1) to (105), wherein —$Y^7$, if present, is independently —$Y^{7C}$.

The Group —$Y^{7A}$ (110) A compound according to any one of (1) to (109), wherein —$Y^{7A}$, if present, is independently —$NHR^{YA}$, —$NHR^{YB}$, or —$NHR^{YD}$.

(111) A compound according to any one of (1) to (109), wherein —$Y^{7A}$, if present, is independently —$NHR^{YA}$, —$NHR^{YB}$, or —$NHR^{YD}$.

(112) A compound according to any one of (1) to (109), wherein —$Y^{7A}$, if present, is independently —$NHR^{YA}$ or —$NHR^{YD}$.

(113) A compound according to any one of (1) to (109), wherein —$Y^{7A}$, if present, is independently —$NHR^{YA}$.

The Group —$Y^{7B}$ (114) A compound according to any one of (1) to (113), wherein —$Y^{7B}$, if present, is independently —$NR^{YA}_2$, —$NR^{YB}_2$, —$NR^{YC}_2$, or —$NR^{YD}_2$.

(115) A compound according to any one of (1) to (113), wherein —$Y^{7B}$, if present, is independently —$NR^{YA}_2$, —$NR^{YB}_2$, or —$NR^{YC}_2$.

(116) A compound according to any one of (1) to (113), wherein —$Y^{7B}$, if present, is independently —$NR^{YA}_2$ or —$NR^{YB}_2$.

(117) A compound according to any one of (1) to (113), wherein —$Y^{7B}$, if present, is independently —$NR^{YA}_2$.

The Group —$Y^7C$ (118) A compound according to any one of (1) to (117), wherein —Y$^{7C}$, if present, is independently pyrrolidino, piperidino, piperazino, or morpholino, and is optionally substituted with one or more groups —Y$^{7X}$, wherein each —Y$^{7X}$ is independently saturated aliphatic C$_{1-4}$alkyl.

(119) A compound according to any one of (1) to (117), wherein —Y$^{7C}$, if present, is independently pyrrolidino, piperidino, piperazino, N-methylpiperazino, or morpholino.

The Group —R$^{YA}$ (120) A compound according to any one of (1) to (119), wherein each —R$^{YA}$, if present, is independently saturated aliphatic C$_{1-4}$alkyl.

(121) A compound according to any one of (1) to (119), wherein each —R$^{YA}$, if present, is independently -Me, -Et, -nPr, -iPr, -nBu, -iBu, or -tBu.

(122) A compound according to any one of (1) to (119), wherein each —R$^{YA}$, if present, is independently -Me, -Et, -nPr, or -iPr.

(123) A compound according to any one of (1) to (119), wherein each —R$^{YA}$, if present, is independently -Me or -Et.

(124) A compound according to any one of (1) to (119), wherein each —R$^{YA}$, if present, is independently -Me.

The Group —R$^{YB}$ (125) A compound according to any one of (1) to (124), wherein each —R$^{YB}$, if present, is independently saturated aliphatic halo-C$_{1-4}$alkyl.

(126) A compound according to any one of (1) to (124), wherein each —R$^{YB}$, if present, is independently —CF$_3$, —CHF$_2$, —CH$_2$F, —CH$_2$CF$_3$, —CH$_2$CHF$_2$, or —CH$_2$CH$_2$F.

(127) A compound according to any one of (1) to (124), wherein each —R$^{YB}$, if present, is independently —CF$_3$, —CHF$_2$, —CH$_2$F, or —CH$_2$CF$_3$.

(128) A compound according to any one of (1) to (124), wherein each —R$^{YB}$, if present, is independently —CF$_3$ or —CHF$_2$.

(129) A compound according to any one of (1) to (124), wherein each —R$^{YB}$, if present, is independently —CF$_3$.

The Group —R$^{YC}$ (130) A compound according to any one of (1) to (129), wherein each —R$^{YC}$, if present, is independently saturated aliphatic hydroxy-C$_{1-4}$alkyl.

(131) A compound according to any one of (1) to (129), wherein each —R$^{YC}$, if present, is independently —CH$_2$OH, —CH$_2$CH$_2$OH, —CH$_2$CH$_2$CH$_2$OH, —CH(CH$_3$)$_2$OH, or —CH$_2$CH$_2$CH$_2$CH$_2$OH.

(132) A compound according to any one of (1) to (129), wherein each —R$^{YC}$, if present, is independently —CH$_2$OH, —CH$_2$CH$_2$OH, —CH$_2$CH$_2$CH$_2$OH, or —CH$_2$CH$_2$CH$_2$CH$_2$OH.

(133) A compound according to any one of (1) to (129), wherein each —R$^{YC}$, if present, is independently —CH$_2$OH, —CH$_2$CH$_2$OH or —CH$_2$CH$_2$CH$_2$OH.

(134) A compound according to any one of (1) to (129), wherein each —R$^{YC}$, if present, is independently —CH$_2$OH.

The Group —R$^{YD}$ (135) A compound according to any one of (1) to (134), wherein each —R$^{YD}$, if present, is independently cyclopropyl, cyclobutyl, or cyclopentyl.

(136) A compound according to any one of (1) to (134), wherein each —R$^{YD}$, if present, is independently cyclopropyl.

The Group —Y: Some Preferred Groups (137) A compound according to any one of (1) to (78), wherein Y is independently -Me, -Et, —OH, —OMe, —OEt, —F, —Cl, —CN, —CH$_2$CF$_3$, or —OCH$_2$CF$_3$.

(138) A compound according to any one of (1) to (78), wherein Y is independently —OH, —OMe, —F, —Cl, —CN, or —CH$_2$CF$_3$.

(139) A compound according to any one of (1) to (78), wherein Y is independently —OH, —OMe, —F, —Cl, or —CN.

(140) A compound according to any one of (1) to (78), wherein Y is independently —OH, —F, —Cl, or —CN.

(141) A compound according to any one of (1) to (78), wherein Y is independently —OH, —OMe, —F, or —CN.

(142) A compound according to any one of (1) to (78), wherein Y is independently —OH, —F, or —CN.

(143) A compound according to any one of (1) to (78), wherein Y is independently —OH.

(144) A compound according to any one of (1) to (78), wherein Y is independently —F.

(145) A compound according to any one of (1) to (78), wherein Y is independently —CN.

The Groups —R$^{A1}$ and —R$^{A2}$ (146) A compound according to any one of (1) to (145), wherein:
—R$^{A1}$ is independently —H or —R$^{AA}$; and
—R$^{A2}$ is independently —H.

(147) A compound according to any one of (1) to (145), wherein:
—R$^{A1}$ is independently —H; and
—R$^{A2}$ is independently —H or —R$^{AA}$.

(148) A compound according to any one of (1) to (145), wherein:
—R$^{A1}$ is independently —H; and
—R$^{A2}$ is independently —H.

(149) A compound according to any one of (1) to (145), wherein:
—R$^{A1}$ is independently —R$^{AA}$; and
—R$^{A2}$ is independently —R$^{AA}$.

The Group —R$^{AA}$ (150) A compound according to any one of (1) to (149), wherein each —R$^{AA}$, if present, is independently —R$^{AA1}$ or —R$^{AA2}$.

(151) A compound according to any one of (1) to (149), wherein each —R$^{AA}$, if present, is independently —R$^{AA1}$ or —R$^{AA3}$.

(152) A compound according to any one of (1) to (149), wherein each —R$^{AA}$, if present, is independently —R$^{AA2}$ or —R$^{AA3}$.

(153) A compound according to any one of (1) to (149), wherein each —R$^{AA}$, if present, is independently —R$^{AA1}$.

(154) A compound according to any one of (1) to (149), wherein each —R$^{AA}$, if present, is independently —R$^{AA2}$.

(155) A compound according to any one of (1) to (149), wherein each —R$^{AA}$, if present, is independently —R$^{AA3}$.

The Group —R$^{AA1}$ (156) A compound according to any one of (1) to (155), wherein each —R$^{AA1}$, if present, is independently -Me, -Et, -nPr, -iPr, -nBu, -iBu, -sBu, -tBu, —CF$_3$, —CH$_2$F, —CHF$_2$, or —CH$_2$CHF$_3$.

(157) A compound according to any one of (1) to (155), wherein each —R$^{AA1}$, if present, is independently unsubstituted saturated aliphatic C$_{1-4}$alkyl.

(158) A compound according to any one of (1) to (155), wherein each —R$^{AA}$, if present, is independently -Me, -Et, -nPr, -iPr, -nBu, -iBu, or -tBu.

(159) A compound according to any one of (1) to (155), wherein each —R$^{AA1}$, if present, is independently -Me or -Et.

(160) A compound according to any one of (1) to (155), wherein each —R$^{AA1}$, if present, is independently -Me.

The Group —$R^{AA2}$ (161) A compound according to any one of (1) to (160), wherein each —$R^{AA2}$, if present, is independently —F.

(162) A compound according to any one of (1) to (160), wherein each —$R^{AA2}$, if present, is independently —Cl.

The Groups —$R^{B1}$ and —$R^{B2}$ (163) A compound according to any one of (1) to (162), wherein:
—$R^{B1}$ is independently —H or —$R^{BB}$; and
—$R^{B2}$ is independently —H.

(164) A compound according to any one of (1) to (162), wherein:
—$R^{B1}$ is independently —H; and
—$R^{B2}$ is independently —H or —$R^{BB}$.

(165) A compound according to any one of (1) to (162), wherein:
—$R^{B1}$ is independently —H; and
—$R^{B2}$ is independently —H.

(166) A compound according to any one of (1) to (162), wherein:
—$R^{B1}$ is independently —$R^{BB}$; and
—$R^{B2}$ is independently —$R^{BB}$.

The Group —$R^{BB}$ (167) A compound according to any one of (1) to (166), wherein each —$R^{BB}$, if present, is independently —$R^{BB1}$ or —$R^{BB2}$.

(168) A compound according to any one of (1) to (166), wherein each —$R^{BB}$, if present, is independently —$R^{BB1}$ or —$R^{BB3}$.

(169) A compound according to any one of (1) to (166), wherein each —$R^{BB}$, if present, is independently —$R^{BB2}$ or —$R^{BB3}$.

(170) A compound according to any one of (1) to (166), wherein each —$R^{BB}$, if present, is independently —$R^{BB1}$.

(171) A compound according to any one of (1) to (166), wherein each —$R^{BB}$, if present, is independently —$R^{BB2}$.

(172) A compound according to any one of (1) to (166), wherein each —$R^{BB}$, if present, is independently —$R^{BB3}$.

The Group —$R^{BB1}$ (173) A compound according to any one of (1) to (172), wherein each —$R^{BB1}$, if present, is independently -Me, -Et, -nPr, -iPr, -nBu, -iBu, -sBu, -tBu, —$CF_3$, —$CH_2F$, —$CHF_2$, or —$CH_2CHF_2$.

(174) A compound according to any one of (1) to (172), wherein each —$R^{BB1}$, if present, is independently unsubstituted saturated aliphatic $C_{1-4}$alkyl.

(175) A compound according to any one of (1) to (172), wherein each —$R^{BB1}$, if present, is independently -Me, -Et, -nPr, -iPr, -nBu, -iBu, or -tBu.

(176) A compound according to any one of (1) to (172), wherein each —$R^{BB1}$, if present, is independently -Me or -Et.

(177) A compound according to any one of (1) to (172), wherein each —$R^{BB1}$, if present, is independently -Me.

The Group —$R^{BB2}$ (178) A compound according to any one of (1) to (177), wherein each —$R^{BB2}$, if present, is independently —F.

(179) A compound according to any one of (1) to (177), wherein each —$R^{BB2}$, if present, is independently —Cl.

The Group —$R^{N}$ (180) A compound according to any one of (1) to (179), wherein —$R^{N}$ is independently —H.

(181) A compound according to any one of (1) to (179), wherein —$R^{N}$ is independently —$R^{NN}$.

The Group —$R^{NN}$ (182) A compound according to any one of (1) to (181), wherein —$R^{NN}$, if present, is independently -Me, -Et, -nPr, -iPr, -nBu, -iBu, or -tBu.

(183) A compound according to any one of (1) to (181), wherein —$R^{NN}$, if present, is independently -Me or -Et.

Orientation of —Y and -Q (184) A compound according to any one of (1) to (183), wherein:
-$J^1$ and -$J^3$ taken together form —$CH_2$— or —$CH_2CH_2$—; and
—Y and the -$J^1$-$J^3$-bridge are positioned on the same face of the piperidine ring.

(185) A compound according to any one of (1) to (183), wherein:
-$J^1$ and -$J^3$ taken together form —$CH_2$—; and
—Y and the —$CH_2$— bridge are positioned on the same face of the piperidine ring;

as in, for example:

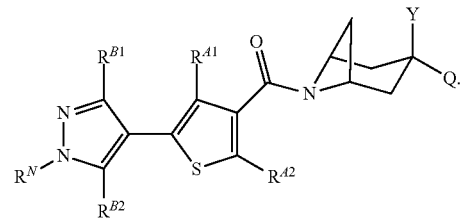

(186) A compound according to any one of (1) to (183), wherein:
-$J^1$ and -$J^3$ taken together form —$CH_2CH_2$—; and
—Y and the —$CH_2CH_2$— bridge are positioned on the same face of the piperidine ring;

as in, for example:

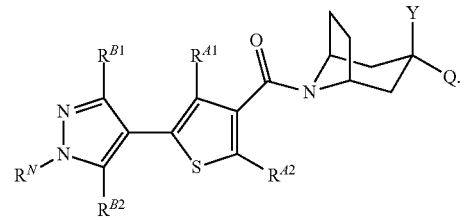

(187) A compound according to any one of (1) to (183), wherein:
-$J^1$ and -$J^3$ taken together form —$CH_2$— or —$CH_2CH_2$—; and
—Y and the -J-$J^3$-bridge are positioned on opposite faces of the piperidine ring.

(188) A compound according to any one of (1) to (183), wherein:
-$J^1$ and -$J^3$ taken together form —$CH_2$—; and
—Y and the —$CH_2$— bridge are positioned on opposite faces of the piperidine ring;

as in, for example:

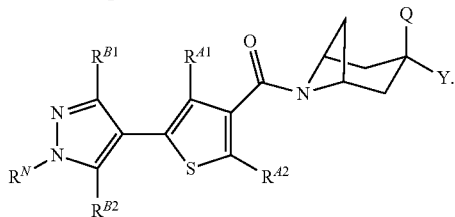

(189) A compound according to any one of (1) to (183), wherein:
-J¹ and -J³ taken together form —CH₂CH₂—; and
—Y and the —CH₂CH₂— bridge are positioned on opposite faces of the piperidine ring;
as in, for example:

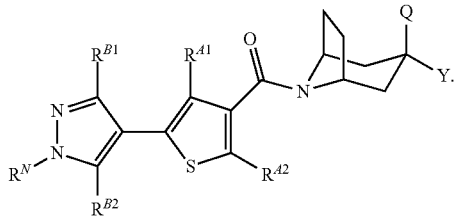

For the avoidance of doubt, unless otherwise indicated, where no conformation is indicated, both or all possible conformations are encompassed.

Molecular Weight (190) A compound according to any one of (1) to (189), wherein has a molecular weight of from 341 to 1200.

(191) A compound according to (190), wherein the bottom of the range is 350, 370, 375, 400, or 425.

(192) A compound according to (190) or (191), wherein the top of the range is 1100, 1000, 900, 800, 700, 600, 500, or 450.

(193) A compound according to any one of (1) to (189), wherein the compound has a molecular weight of from 370 to 450.

Examples of Some Specific Embodiments (194) A compound according to (1), selected from compounds of the following formulae and pharmaceutically acceptable salts, hydrates, and solvates thereof:

| Compound No. | Synthesis No. | Structure |
|---|---|---|
| XX-01 | 1 | 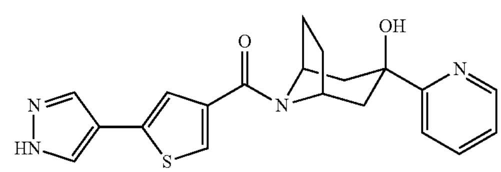 |
| XX-02 | 1 | 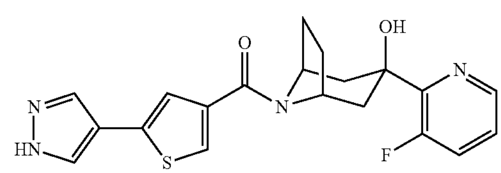 [SMILES: O=C(c1csc(-c2cn[nH]c2)c1)N1C2CCC1CC(O)(c1ncccc1F)C2] |
| XX-03 | 1 | 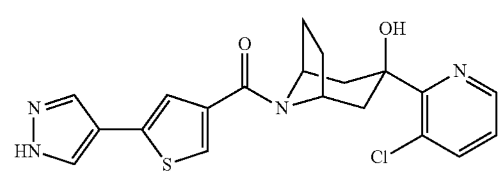 |
| XX-04 | 1 | 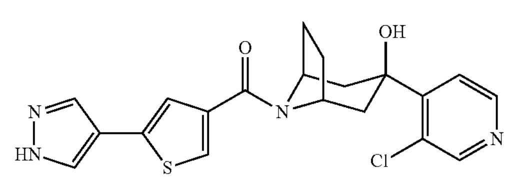 [SMILES: O=C(c1csc(-c2cn[nH]c2)c1)N1C2CCC1CC(O)(c1ccncc1Cl)C2] |
| XX-05 | 1 | 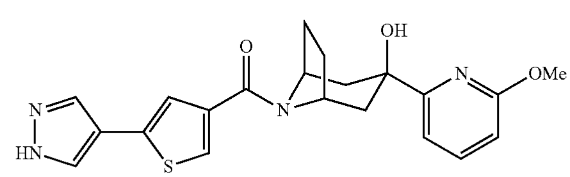 [SMILES: COc1cccc(C2(O)CC3CCC(C2)N3C(=O)c2csc(-c3cn[nH]c3)c2)n1] |

-continued

| Compound No. | Synthesis No. | Structure |
|---|---|---|
| XX-06 | 1 | 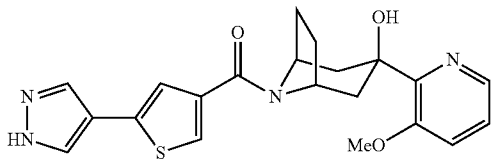 [SMILES: COc1cccnc1C1(O)CC2CCC(C1)N2C(=O)c1csc(-c2cn[nH]c2)c1] |
| XX-07 | 1 | 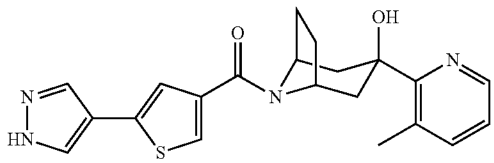 [SMILES: Cc1cccnc1C1(O)CC2CCC(C1)N2C(=O)c1csc(-c2cn[nH]c2)c1] |
| XX-08 | 1 | 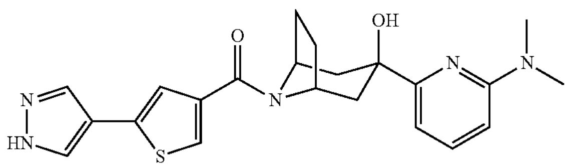 [SMILES: CN(C)c1cccc(C2(O)CC3CCC(C2)N3C(=O)c2csc(-c3cn[nH]c3)c2)n1] |
| XX-09 | 1 | 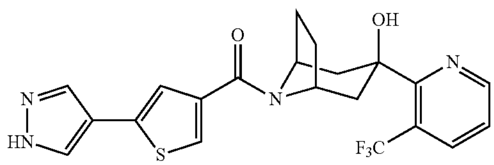 [SMILES: O=C(c1csc(-c2cn[nH]c2)c1)N1C2CCC1CC(O)(c1ncccc1C(F)(F)F)C2] |
| XX-10 | 1 | 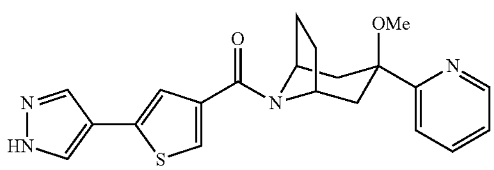 [SMILES: COC1(c2ccccn2)CC2CCC(C1)N2C(=O)c1csc(-c2cn[nH]c2)c1] |
| XX-11 | 1 | 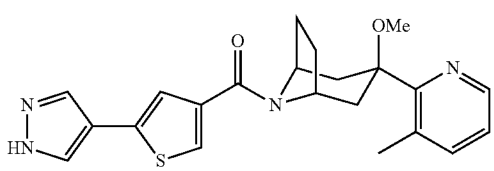 [SMILES: COC1(c2ncccc2C)CC2CCC(C1)N2C(=O)c1csc(-c2cn[nH]c2)c1] |
| XX-12 | 1 | 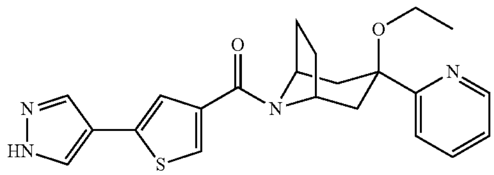 [SMILES: CCOC1(c2ccccn2)CC2CCC(C1)N2C(=O)c1csc(-c2cn[nH]c2)c1] |
| XX-13 | 33 | 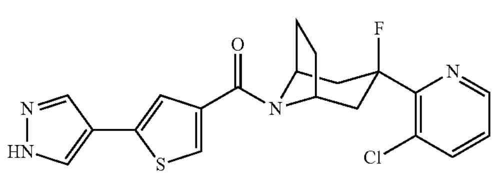 |

PA Mixture

-continued
| Compound No. | Synthesis No. | Structure |
|---|---|---|
| XX-14 | 1 | 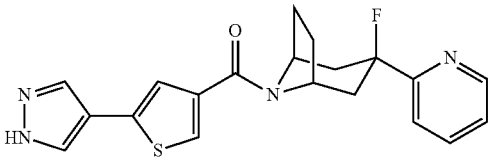<br>PA Isomer 1 |
| XX-15 | 1 | 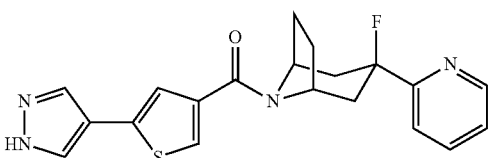<br>PA Isomer 2 |
| XX-16 | 2 | 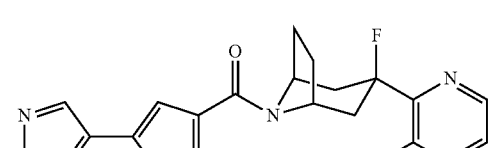<br>PA Isomer 1 |
| XX-17 | 2 | 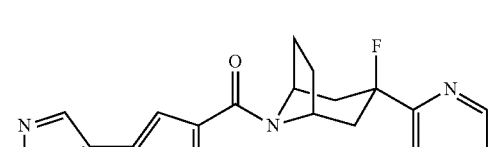<br>PA Isomer 2 |
| XX-18 | 1 | 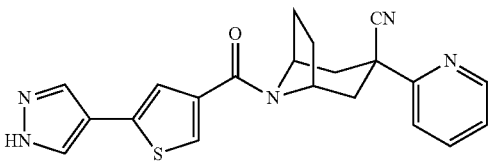 [SMILES: N#CC1(c2ccccn2)CC2CCC(C1)N2C(=O)c1csc(-c2cn[nH]c2)c1] |
| XX-19 | 1 | 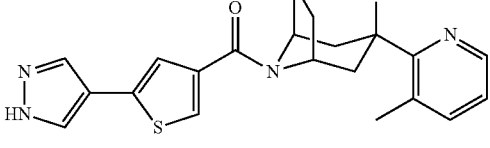 |
| XX-20 | 1 | 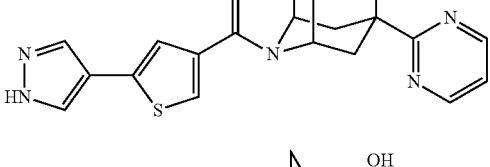 |
| XX-21 | 1 | 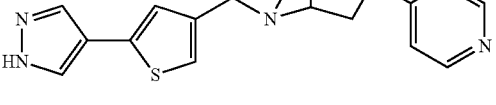 |

-continued
| Compound No. | Synthesis No. | Structure |
|---|---|---|
| XX-22 | 1 | 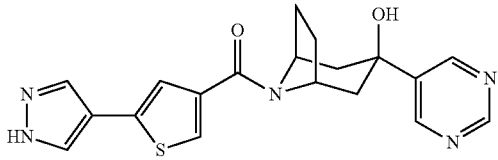 [SMILES: O=C(c1csc(-c2cn[nH]c2)c1)N1C2CCC1CC(O)(c1cncnc1)C2] |
| XX-23 | 1 | 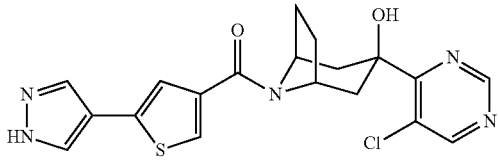 [SMILES: O=C(c1csc(-c2cn[nH]c2)c1)N1C2CCC1CC(O)(c1ncncc1Cl)C2] |
| XX-24 | 1 | 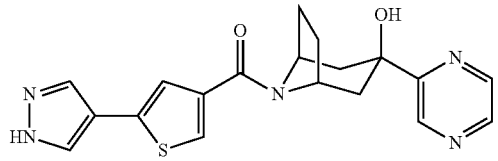 [SMILES: O=C(c1csc(-c2cn[nH]c2)c1)N1C2CCC1CC(O)(c1cnccn1)C2] |
| XX-25 | 1 | 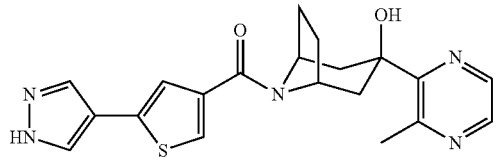 |
| XX-26 | 1 | 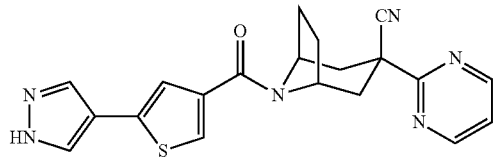 |
| XX-27 | 1 | 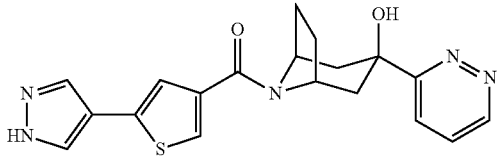<br>PA Isomer 1 |
| XX-28 | 1 | 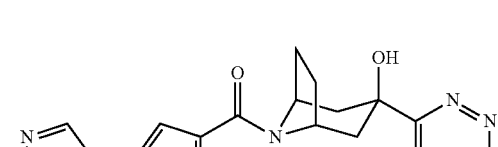<br>PA Isomer 2 |
| XX-29 | 1 | 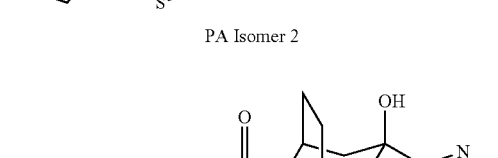 |

-continued
| Compound No. | Synthesis No. | Structure |
|---|---|---|
| XX-30 | 1 | 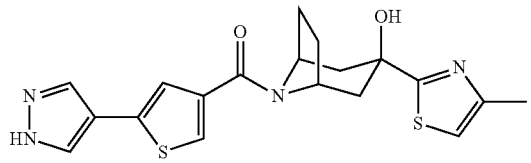<br>PA Isomer 1 |
| XX-31 | 1 | 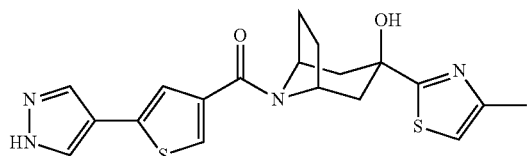<br>PA Isomer 2 |
| XX-32 | 1 | 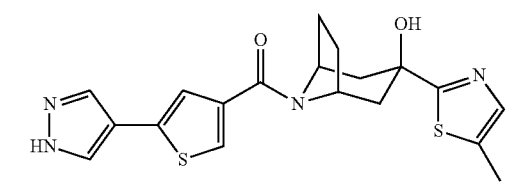<br>PA Isomer 1 |
| XX-33 | 1 | 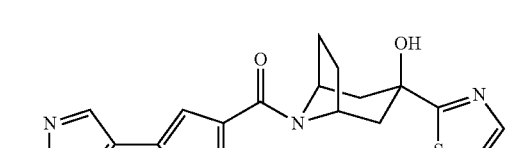<br>PA Isomer 2 |
| XX-34 | 34 | 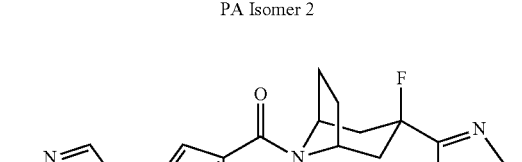<br>PA Isomer 1 |
| XX-35 | 1 | 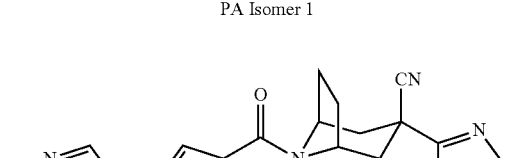 |
| XX-36 | 1 | 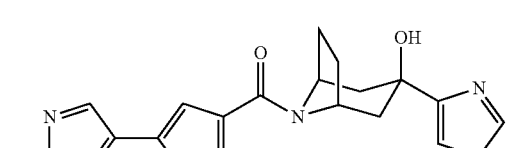 |

-continued
| Compound No. | Synthesis No. | Structure |
|---|---|---|
| XX-37 | 1 | 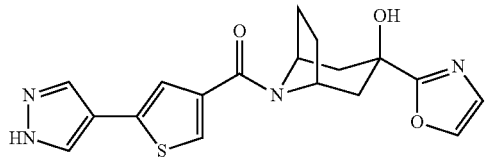 [SMILES: O=C(c1csc(-c2cn[nH]c2)c1)N1C2CCC1CC(O)(c1nccs1)C2]<br>PA mixture |
| XX-38 | 1 | 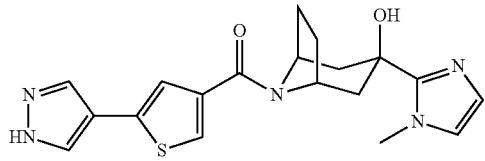 [SMILES: Cn1ccnc1C1(O)CC2CCC(C1)N2C(=O)c1csc(-c2cn[nH]c2)c1] |
| XX-39 | 1 | 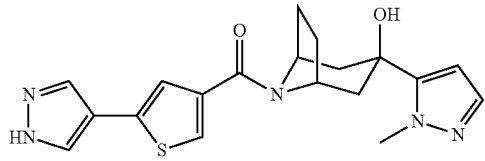 [SMILES: Cn1nccc1C1(O)CC2CCC(C1)N2C(=O)c1csc(-c2cn[nH]c2)c1] |
| XX-40 | 1 | 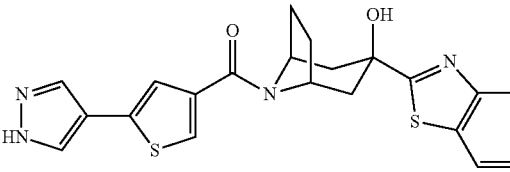 |
| XX-41 | 1 | 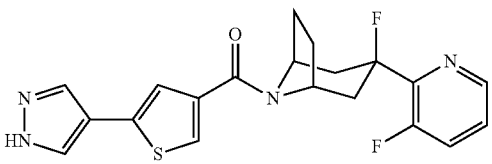<br>PA Isomer 1 |
| XX-42 | 1 | 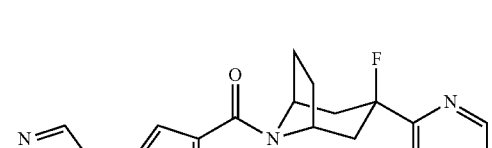<br>PA Isomer 2 |
| XX-43 | 1 | 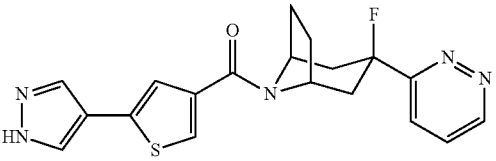<br>PA Isomer 1 |

(195) A compound according to (1), selected from compounds of the following formulae and pharmaceutically acceptable salts, hydrates, and solvates thereof:

| Compound No. | Synthesis No. | Structure |
| --- | --- | --- |
| YY-01 | 1 | 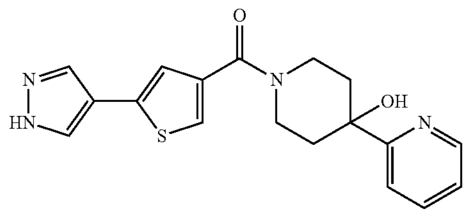 [SMILES: O=C(c1csc(-c2cn[nH]c2)c1)N1CCC(O)(c2ccccn2)CC1] |
| YY-02 | 1 | 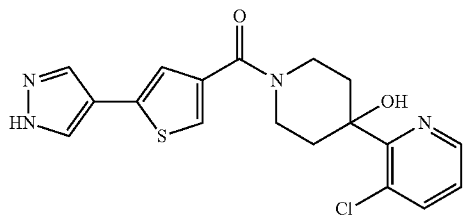 [SMILES: O=C(c1csc(-c2cn[nH]c2)c1)N1CCC(O)(c2ncccc2Cl)CC1] |
| YY-03 | 1 | 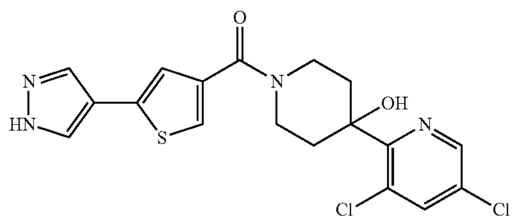 [SMILES: O=C(c1csc(-c2cn[nH]c2)c1)N1CCC(O)(c2ncc(Cl)cc2Cl)CC1] |
| YY-04 | 1 | 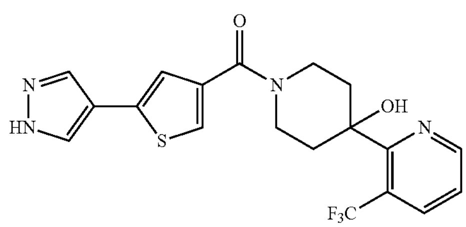 [SMILES: O=C(c1csc(-c2cn[nH]c2)c1)N1CCC(O)(c2ncccc2C(F)(F)F)CC1] |
| YY-05 | 1 | 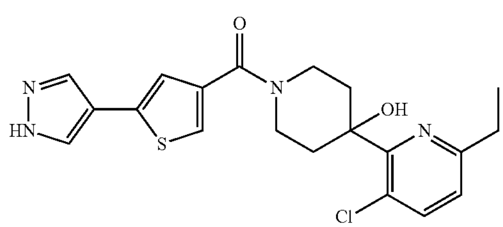 [SMILES: CCc1ccc(Cl)c(C2(O)CCN(C(=O)c3csc(-c4cn[nH]c4)c3)CC2)n1] |
| YY-06 | 1 | 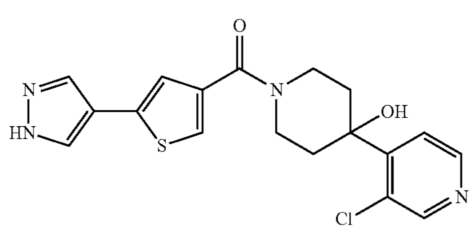 [SMILES: O=C(c1csc(-c2cn[nH]c2)c1)N1CCC(O)(c2ccncc2Cl)CC1] |

-continued

| Compound No. | Synthesis No. | Structure |
|---|---|---|
| YY-07 | 1 | 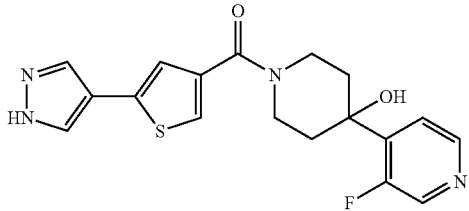 [SMILES: O=C(c1csc(-c2cn[nH]c2)c1)N1CCC(O)(c2ccncc2F)CC1] |
| YY-08 | 1 | 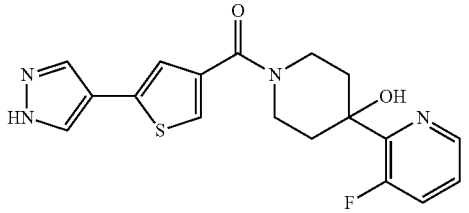 [SMILES: O=C(c1csc(-c2cn[nH]c2)c1)N1CCC(O)(c2ncccc2F)CC1] |
| YY-09 | 1 | 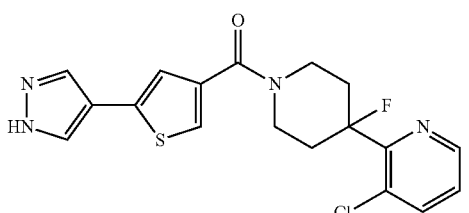 |
| YY 10 | 1 | 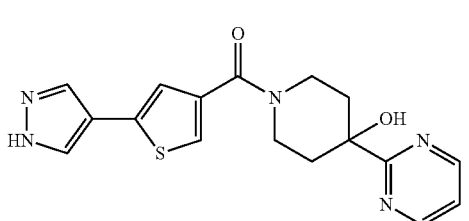 |
| YY-11 | 1 | 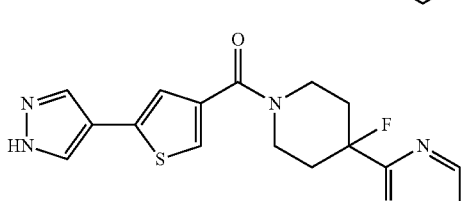 |

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., -$J^1$, -$J^3$, -Q, n, —$R^F$, —$R^F$, —$R^Z$, —$R^{ZZ}$, —Y, —$Y^1$, —$Y^2$, —$Y^3$, —$Y^4$, —$Y^5$, —$Y^6$, —$Y^7$, —$Y^{2A}$, —$Y^{2B}$, —$Y^{2C}$, —$Y^{2D}$, —$Y^{3A}$, —$Y^{3B}$, —$Y^{3C}$, —$Y^{3D}$, —$Y^{7A}$, —$Y^{7B}$, —$Y^{7C}$, —$R^{YA}$, —$R^{YB}$, —$R^{YC}$, —$R^{YD}$, $R^{A1}$, $R^{A2}$, —$R^{AA}$, —$R^{AA1}$, —$R^{AA2}$, —$R^{AA3}$, $R^{B1}$, —$R^{B2}$, —$R^{BB}$, —$R^{BB1}$, —$R^{BB2}$, —$R^{BB3}$, —$R^N$, —$R^{NN}$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to DSPT compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diasteriomeric, epimeric, atropic, stereoisomeric, tautomeric, conformational, pseudo-asymmetric or anomeric forms, including but not limited to, cis- and trans-forms; E- and Z-forms; c-, t-, s- and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Some of the DSPT compounds have a piperidine ring with a —CH$_2$— bridge (giving a 6-aza-bicyclo[3.1.1]heptane group) or with a —CH$_2$CH$_2$— bridge (giving a 8-aza-bicyclo[3.2.1]octane group). Such compounds contain a pseudo-asymmetric centre at the carbon bearing the groups -Q and —Y, and can exist in two isomeric forms. For convenience, one isomeric form is defined as having both the group —Y and the bridge (i.e., —CH$_2$— or —CH$_2$CH$_2$—) on the same face of the piperidine ring, and the other isomeric form is defined as having the group —Y and the bridge (i.e., —CH$_2$— or —CH$_2$CH$_2$—) on opposite faces of the piperidine ring.

Unless otherwise specified, a reference to a particular compound includes all such isomeric forms, including mixtures thereof. Methods for the preparation (e.g., asymmetric synthesis), and separation (e.g., fractional crystallisation and chromatographic means) of such isomeric forms are known in the art or are readily obtained by adapting the methods taught therein, or known methods in a known manner.

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

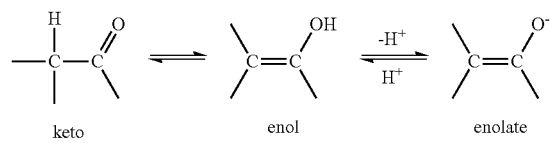

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., $-NH_2$ may be $-NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 4th Edition; John Wiley and Sons, 2006).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether ($-OR$) or an ester ($-OC(=O)R$), for example, as: a t-butyl ether; a benzyl, benzhydryl (diphenylmethyl), or trityl (triphenylmethyl) ether; a trimethylsilyl or t-butyldimethylsilyl ether; or an acetyl ester ($-OC(=O)CH_3$, $-OAc$).

For example, an aldehyde or ketone group may be protected as an acetal ($R-CH(OR)_2$) or ketal ($R_2C(OR)_2$), respectively, in which the carbonyl group ($>C=O$) is converted to a diether ($>C(OR)_2$), by reaction with, for example, a primary alcohol. The aldehyde or ketone group is readily regenerated by hydrolysis using a large excess of water in the presence of acid.

For example, an amine group may be protected, for example, as an amide ($-NRCO-R$) or a urethane ($-NRCO-OR$), for example, as: a methyl amide ($-NHCO-CH_3$); a benzyl amide ($-NHCH_2C_6H_5$); a benzyloxy amide ($-NHCO-OCH_2C_6H_5$, $-NH$-Cbz); as a t-butoxy amide ($-NHCO-OC(CH_3)_3$, $-NH$-Boc); a 2-biphenyl-2-propoxy amide ($-NHCO-OC(CH_3)_2C_6H_4C_6H_5$, $-NH$-Bpoc), as a 9-fluorenylmethoxy amide ($-NH$-Fmoc), as a 6-nitroveratryloxy amide ($-NH$-Nvoc), as a 2-trimethylsilylethyloxy amide ($-NH$-Teoc), as a 2,2,2-trichloroethyloxy amide ($-NH$-Troc), as an allyloxy amide ($-NH$-Alloc), as a 2(-phenylsulfonyl)ethyloxy amide ($-NH$-Psec); or, in suitable cases (e.g., cyclic amines), as a nitroxide radical ($>N-O.$).

For example, a carboxylic acid group may be protected as an ester for example, as: a $C_{1-7}$alkyl ester (e.g., a methyl ester; a t-butyl ester); a $C_{1-7}$haloalkyl ester (e.g., a $C_{1-7}$trihaloalkyl ester); a $triC_{1-7}$alkylsilyl-$C_{1-7}$alkyl ester; or a $C_{5-20}$aryl-$C_{1-7}$alkyl ester (e.g., a benzyl ester; a nitrobenzyl ester); or as an amide, for example, as a methyl amide.

For example, a thiol group may be protected as a thioether ($-SR$), for example, as: a benzyl thioether; an acetamidomethyl ether ($-S-CH_2NHC(=O)CH_3$).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Several methods for the chemical synthesis of DSPT compounds of the present invention are described herein. These and/or other well known methods may be modified and/or adapted in known ways in order to facilitate the synthesis of additional compounds within the scope of the present invention.

Compositions

One aspect of the present invention pertains to a composition (e.g., a pharmaceutical composition) comprising a DSPT compound, as described herein, and a pharmaceutically acceptable carrier, diluent, or excipient.

Another aspect of the present invention pertains to a method of preparing a composition (e.g., a pharmaceutical composition) comprising admixing a DSPT compound, as described herein, and a pharmaceutically acceptable carrier, diluent, or excipient.

Uses

The DSPT compounds, as described herein, are useful, for example, in the treatment of disorders (e.g., diseases) that are ameliorated by the inhibition of 11β-hydroxysteroid dehydrogenase type 1 (11β-HSD1), as described herein.

Use in Methods of Inhibiting 11β-Hydroxysteroid Dehydrogenase Type 1 (1β-HSD1)

One aspect of the present invention pertains to a method of inhibiting 11β-hydroxysteroid dehydrogenase type 1 in a cell, in vitro or in vivo, comprising contacting the cell with an effective amount of a DSPT compound, as described herein.

Suitable assays for determining 11β-hydroxysteroid dehydrogenase type 1 inhibition are described herein and/or are known in the art. In one embodiment, the method is performed in vitro.

In one embodiment, the method is performed in vivo.

In one embodiment, the DSPT compound is provided in the form of a pharmaceutically acceptable composition.

Any type of cell may be treated, including but not limited to, adipose, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound inhibits 11β-hydroxysteroid dehydrogenase type 1. For example, suitable assays are described herein.

For example, a sample of cells may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to a DSPT compound, as described herein, for use in a method of treatment of the human or animal body by therapy.

Use in the Manufacture of Medicaments

Another aspect of the present invention pertains to use of a DSPT compound, as described herein, in the manufacture of a medicament for use in treatment.

In one embodiment, the medicament comprises the DSPT compound.

Methods of Treatment

Another aspect of the present invention pertains to a method of treatment comprising administering to a patient in need of treatment a therapeutically effective amount of a DSPT compound, as described herein, preferably in the form of a pharmaceutical composition.

Disorders Treated—Disorders Ameliorated by the Inhibition of 11β-Hydroxysteroid Dehydrogenase Type 1

In one embodiment (e.g., of use in methods of therapy, of use in the manufacture of medicaments, of methods of treatment), the treatment is treatment or prevention of a disorder (e.g., a disease) that is ameliorated by the inhibition of 11β-hydroxysteroid dehydrogenase type 1.

Disorders Treated—Disorders Characterised by Up-Regulation of 11β-HSD1 Etc.

In one embodiment (e.g., of use in methods of therapy, of use in the manufacture of medicaments, of methods of treatment), the treatment is treatment or prevention of a disorder (e.g., a disease) that is characterised by one or more of: up-regulation of 11β-HSD1; up-regulation of glucocorticoid receptor mediated pathways; elevated PEPCK levels; other biochemical markers pertaining to glucocorticoid excess and insulin resistance.

Disorders Treated

In one embodiment (e.g., of use in methods of therapy, of use in the manufacture of medicaments, of methods of treatment), the treatment is treatment or prevention of one or more of the following:

(1) Cushing's syndrome;
(2) type 2 diabetes and impaired glucose tolerance;
(3) insulin resistance syndromes such as myotonic dystrophy, Prader Willi, lipodystrophies, polycystic ovary syndrome, gastrointestinal diabetes, etc.;
(4) obesity and being overweight;
(5) lipid disorders including dyslipidaemia;
(6) atherosclerosis and its sequelae, including myocardial infarction and peripheral vascular disease;
(7) Metabolic Syndrome;
(8) steatohepatitis/fatty liver and non-alcoholic fatty liver disease;
(9) cognitive impairment in type 2 diabetes, glucose intolerance and ageing, and in psychotic disorders and pre-schizophrenia;
(10) dementias such as Alzheimer's disease, multi-infarct dementia, dementia with Lewy bodies, fronto-temporal dementia (including Pick's disease), progressive supranuclear palsy, Korsakoff's syndrome, Binswanger's disease, HIV-associated dementia, Creutzfeldt-Jakob disease (CJD), multiple sclerosis, motor neurone disease, Parkinson's disease, Huntington's disease, Niemann-Pick disease type C, normal pressure hydrocephalus, and Down's syndrome;
(11) mild cognitive impairment (cognitive impairment, no dementia);
(12) β-cell dysfunction in pancreatic disease;
(13) glaucoma;
(14) anxiety;
(15) depression and other affective disorders; typical (melancholic) and atypical depression; dysthymia; post-partum depression; bipolar affective disorder; drug-induced affective disorders; anxiety; posttraumatic stress disorder; panic; phobias;
(16) delirium and acute confusional state;
(17) inflammatory disease;
(18) osteoporosis;
(19) myocardial infarction, for example, to prevent left ventricular dysfunction after myocardial infarction; and
(20) stroke, for example, to limit ischaemic neuronal loss after cardiovascular accident.

In one embodiment (e.g., of use in methods of therapy, of use in the manufacture of medicaments, of methods of treatment), the treatment is treatment or prevention of one or more of the following:

(1) hyperglycaemia;
(2) glucose intolerance and impaired glucose tolerance;
(3) insulin resistance;
(4) hyperlipidaemia;
(5) hypertriglyceridaemia;
(6) hypercholesterolaemia;
(7) low HDL levels;
(8) high LDL levels;
(9) vascular restenosis;
(10) abdominal obesity;

(11) neurodegenerative disease;
(12) retinopathy;
(13) neuropathy;
(14) hypertension; and
(15) other diseases where insulin resistance is a component.

In one embodiment (e.g., of use in methods of therapy, of use in the manufacture of medicaments, of methods of treatment), the treatment is treatment or prevention of an adverse effect of glucocorticoids used to treat inflammatory diseases, such as asthma, chronic obstructive pulmonary disease, skin diseases, rheumatoid arthritis and other arthropathies, inflammatory bowel disease, and giant cell arthritis/polymyalgia rheumatica.

In one embodiment (e.g., of use in methods of therapy, of use in the manufacture of medicaments, of methods of treatment), the treatment is treatment or prevention of metabolic syndrome, which includes disorders such as type 2 diabetes and obesity, and associated disorders including insulin resistance, hypertension, lipid disorders and cardiovascular disorders such as ischaemic (coronary) heart disease.

In one embodiment (e.g., of use in methods of therapy, of use in the manufacture of medicaments, of methods of treatment), the treatment is treatment or prevention of a CNS disorder (e.g., a CNS disease) such as mild cognitive impairment and early dementia, including Alzheimer's disease.

Treatment

The term "treatment," as used herein in the context of treating a disorder, pertains generally to treatment and therapy, whether of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment."

For example, treatment includes the prophylaxis of metabolic syndrome, reducing the incidence of metabolic syndrome, alleviating the symptoms of metabolic syndrome, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

One aspect of the present invention pertains to a compound as described herein, in combination with one or more (e.g., 1, 2, 3, 4, etc.) additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Examples of additional agents/therapies that may be co-administered/combined with treatment with the DSPT compounds described herein include the following:

(1) insulin and insulin analogues;
(2) insulin sensitising agents, for example: PPAR-γ agonists; PPAR-α agonists; PPAR-α/γ dual agonists; biguanides;
(3) incretin-based therapies and incretin mimetics;
(4) sulfonylureas and other insulin secretogogues;
(5) α-glucosidase inhibitors;
(6) glucagon receptor antagonists;
(7) GLP-1, GLP-1 analogues, and GLP-receptor agonists;
(8) GIP, GIP mimetics, and GIP receptor agonists;
(9) PACAP, PACAP mimetics, and PACAP receptor 3 agonists;
(10) agents that suppress hepatic glucose output, such as metformin;
(11) agents designed to reduce the absorption of glucose from the intestine, such as acarbose;
(12) phosphotyrosine phosphatase 1B inhibitors;
(13) glucose 6-phosphatase inhibitors;
(14) glucokinase activators;
(15) glycogen phosphorylase inhibitors;
(16) fructose 1,6-biphosphatase inhibitors;
(17) SIRT1 activators;
(18) SGLT2 inhibitors;
(19) glutamine:fructose-6-phosphate amidotransferase inhibitors;
(20) anti-obesity agents, including: orilistat, pramlintide, sibutramine, fenfluramine, phentermine, dexfenfluramine, cannabinoid CB1 receptor antagonists or inverse agonists such as rimonobant, ghrelin antagonists, oxyntomodulin, neuropeptide Y1 or Y5 antagonists, 5-HT$_{1B}$ receptor agonists, 5-HT$_{2C}$ receptor agonists, 5-HT$_{1B/2C}$ receptor dual agonists, melanocortin receptor agonists, and melanin-concentrating hormone receptor antagonists, bupropion, naltrexone, phentermine, topiramate, growth hormone analogues, and β3 agonists;
(21) anti-dyslipidaemia agents, including: HMG-CoA reductase inhibitors, PPAR-α agonists, PPAR-α/γ dual agonists, bile acid sequestrants, ileal bile acid absorption inhibitors, acyl CoA:cholesterol acyltransferase inhibitors, cholesterol absorption inhibitors, cholesterol ester transfer protein inhibitors, nicotinyl alcohol and its analogues, and anti-oxidants;
(22) anti-inflammatory agents, including: non-steroidal anti-inflammatory drugs such as aspirin; and steroidal anti-inflammatory agents such as hydrocortisone and dexamethasone;

(23) anti-hypertensive agents, including: 3-blockers such as atenolol and inderal; calcium antagonists such as nifedipine; ACE inhibitors such as lisinopril, aptopril and captopril; angiotensin receptor antagonists such as candesartan, losartan and cilexetil; diuretic agents such as furosemide and benzthiazide; α-antagonists; centrally acting agents such as clonidine, methyl dopa, and indapamide; renin inhibitors; and vasodilators such as hydralazine;

(24) dipeptidyl peptidase IV (DPP-IV) inhibitors such as sitagliptin and saxagliptin;

(25) acetylcholinesterase inhibitors, including: donezepil hydrochloride, rivastigmine and galanthamine;

(26) NMDA receptor blockers, including memantine hydrochloride;

(27) Histamine H3 antagonists;

(28) 5-HT$_6$ receptor antagonists;

(29) α7 receptor agonists; and

(30) γ-secretase modulators, including tarenflurbil.

Other Uses

The DSPT compounds described herein may also be used as cell culture additives to inhibit 11β-hydroxysteroid dehydrogenase type 1 (11β-HSD1), etc.

The DSPT compounds described herein may also be used as part of an in vitro assay, for example, in order to determine whether a candidate host is likely to benefit from treatment with the compound in question.

The DSPT compounds described herein may also be used as a standard, for example, in an assay, in order to identify other active compounds, other 11β-hydroxysteroid dehydrogenase type 1 (11β-HSD1) inhibitors, etc.

Kits

One aspect of the invention pertains to a kit comprising (a) a DSPT compound as described herein, or a composition comprising a DSPT compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The DSPT compound or pharmaceutical composition comprising the DSPT compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the DSPT compound to be administered alone, it is preferable to present it as a pharmaceutical formulation (e.g., composition, preparation, medicament) comprising at least one DSPT compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one DSPT compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichloro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient.

Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about μg/mL, for example from about 10 ng/mL to about 1 μg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the DSPT compounds, and compositions comprising the DSPT compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular DSPT compound, the route of administration, the time of administration, the rate of excretion of the DSPT compound, the duration of the treatment, other drugs, compounds, and/or materials used in combination, the severity of the disorder, and the species, sex, age, weight, condition, general health, and prior medical history of the patient. The amount of DSPT compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the DSPT compound is in the range of about 10 μg to about 250 mg (more typically about 100 μg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

Examples

Chemical Synthesis

The following examples are provided solely to illustrate the present invention and are not intended to limit the scope of the invention, as described herein.

Analytical Method 1:

The system consisted of a Waters Acquity UPLC system and an Acquity BEH C18 1.7 μm 100×2.1 mm column, maintained at 40° C. Detection was achieved using a Waters Micromass ZQ2000 quadrupole mass spectrometer (electrospray, positive ion and negative ion), a PDA UV detector. Mobile Phase A: 0.1% aqueous formic acid, Mobile Phase B: 0.1% formic acid in MeCN. Flow rate 0.4 mL/min: Gradient: 0-0.4 min 5% B; 0.4-6.0 min 5-95% B; 6-6.8 min 95% B; 6.8-7.0 min 95-5% B; 7-8 min 5% B.

Analytical Method 2:

The system consisted of a Hewlett Packard HP1100 LC system and a Higgins Clipeus 5 μm C18 100×3.0 mm column maintained at 40° C. Detection was achieved using a Waters Quattro Micro triple quadrupole mass spectrometer (electrospray, positive ion and negative ion), a DAD UV detector and a Sedex ELS 85 evaporative light scattering detector. Mobile Phase A: 0.1% aqueous formic acid. Mobile Phase B: 0.1% formic acid in MeOH. Flow rate 1 mL/min: Gradient: 0-1 min 15% B; 1-13 min 15-95% B; 13-20 min 95% B; 20-22 min 95-15% B; 22-25 min 15% B.

Analytical Method 3:

The system consisted of a Hewlett Packard 1050 LC system and a Luna 3 μm C18(2) 30×4.6 mm column. Detection was achieved using a Finnigan AQA single quadrupole mass spectrometer (electrospray, positive ion), a UV diode array detector and a Sedex ELS 65 evaporative light scattering detector. Mobile Phase A: 0.1% aqueous formic acid, Mobile Phase B: 0.1% formic acid in MeOH. Flow rate 2 mL/min: Gradient: 0-0.5 min 5% B; 0.5-4.5 min 5-95% B; 4.5-5 min 95% B; 5.5-6.0 min 95-5% B.

NMR Analysis

Proton NMR spectra were obtained using a Varian Unity Inova 400 spectrometer operating at 400 MHz.

Abbreviations

DAST=Diethylaminosulphur trifluoride.
DABCO=1,4-Diazabicyclo[2,2,2]octane.
DCM=Dichloromethane.
DIPEA=Diisopropylethylamine.
DIPA=Diisopropylamine.
DMF=Dimethylformamide.
HATU=(O-(7-azabenzotriazol-1-yl)-N,N,N',N'-tetramethyl-uroniumhexafluoro-phosphate).
HCl=Hydrochloric acid.
HMDS=Hexamethyldisilazane.
IMS=Industrial methylated spirit.
R.T.=retention time.
TFA=Trifluoroacetic acid.
THF=Tetrahydrofuran.
s=singlet.
d=doublet.
t=triplet.
m=multiplet.
q=quartet.

Compounds were named using Autonom.

Compounds containing chiral centres were prepared as racemic mixtures, unless otherwise stated.

Compounds containing a pseudo-asymmetric centre were isolated from the reaction mixture as a single isomer unless otherwise stated.

Where a mixture of two pseudo-asymmetric isomers was obtained and the isomers were not separated, this has been designated as "PA Mixture".

Where such a mixture of two pseudo-asymmetric isomers was separated by chromatography to give individual isomers, each component has been designated as "PA Isomer 1" and "PA Isomer 2".

Synthesis 1

(3-Hydroxy-3-pyrimidin-2-yl-8-aza-bicyclo[3.2.1]oct-8-yl)-[5-(1H-pyrazol-4-yl)-thiophen-3-yl]-methanone (XX-20)

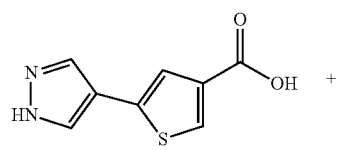

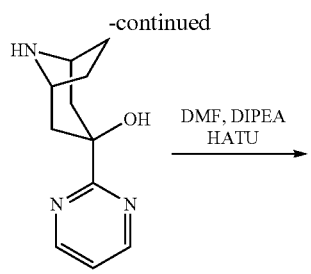

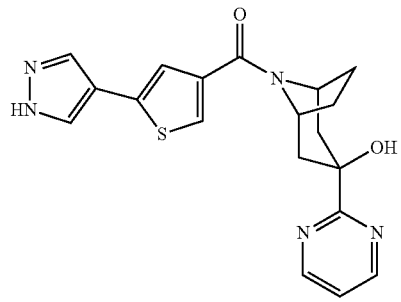

5-(1H-Pyrazol-4-yl)-thiophene-3-carboxylic acid (0.06 g, 0.31 mmol) and 4-pyrimidin-2-yl-piperidin-4-ol (0.082 g, 0.34 mmol) were dissolved in DMF (5 mL). HATU (0.13 g, 0.34 mmol) and diisopropylethylamine (0.32 mL, 1.85 mmol) were added and the resulting mixture was stirred for 2 hours. Aqueous sodium hydroxide (1 N, 3 mL) was added and the mixture stirred for 0.5 hours. The mixture was diluted with ethyl acetate and washed with brine, dried over magnesium sulphate, filtered and the solvent evaporated under vacuum. The residues were purified by HPLC on a C18 cartridge, eluting with 40%-70% methanol/water with 0.1% formic acid. The fractions containing the desired product were concentrated under vacuum and further lyophilised from methanol and water to give the title compound.

LCMS m/z 382.08 [M+H]$^+$ R.T.=3.08 min (Analytical Method 1). $^1$H NMR (400 MHz, d6-DMSO): δ 12.5 (s, broad, 1H), 8.85 (d, 2H), 7.9 (s, 2H), 7.7 (s, 1H), 7.4 (t, 1H), 7.35 (s, 1H), 5.3 (m, broad, 1H), 4.8-4.4 (m, broad, 2H), 2.4-2.3 (m, broad, 3H), 2.1-1.8 (m, broad, 4H).

The following compounds were prepared from substituted piperidines using analogous methods.

| Cmpd. No. | Structure | Analytical Method | R.T. (min) | MS [m/z] [M + H]$^+$ |
|---|---|---|---|---|
| XX-01 | 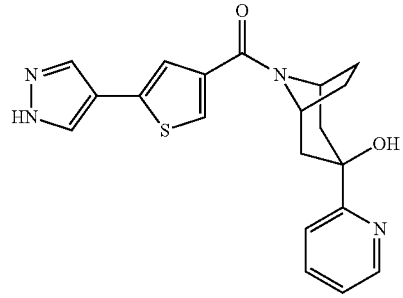 [SMILES: O=C(c1csc(-c2cn[nH]c2)c1)N1C2CCC1CC(O)(c1ccccn1)C2] | 1 | 2.40 | 381.1 |

-continued
| Cmpd. No. | Structure | Analytical Method | R.T. (min) | MS [m/z] [M + H]+ |
|---|---|---|---|---|
| XX-02 | 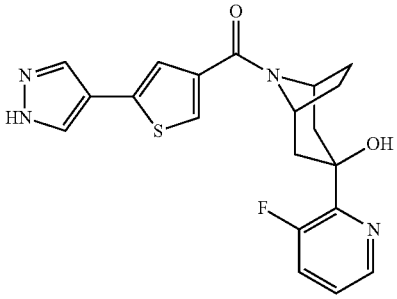 [SMILES: O=C(c1csc(-c2cn[nH]c2)c1)N1C2CCC1CC(O)(c1ncccc1F)C2] | 1 | 3.48 | 399.1 |
| XX-03 | 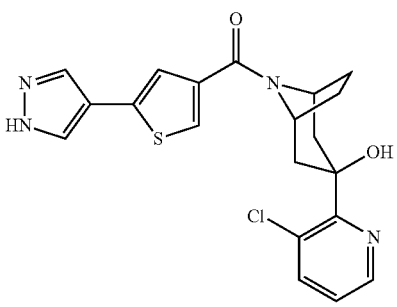 [SMILES: O=C(c1csc(-c2cn[nH]c2)c1)N1C2CCC1CC(O)(c1ncccc1Cl)C2] | 1 | 3.74 | 416.9 |
| XX-04 | 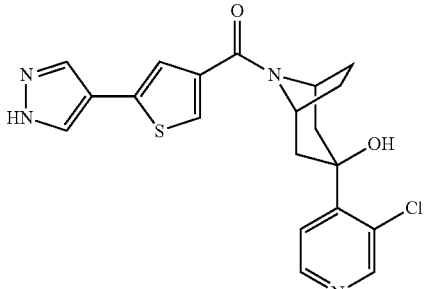 | 1 | 2.93 | 416.9 |
| XX-05 | 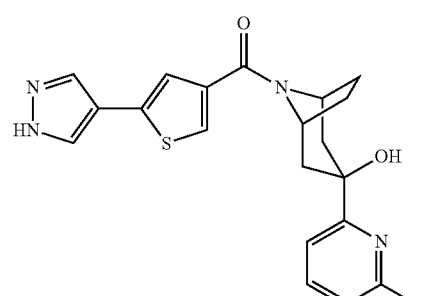 | 1 | 3.63 | 411.1 |
| XX-06 | 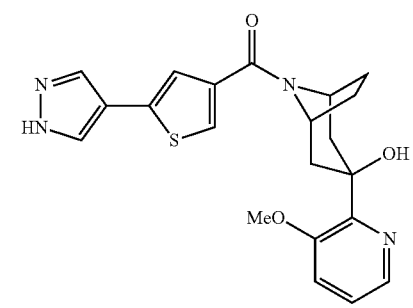 [SMILES: COc1cccnc1C1(O)CC2CCC(C1)N2C(=O)c1csc(-c2cn[nH]c2)c1] | 1 | 2.45 | 411.1 |

-continued

| Cmpd. No. | Structure | Analytical Method | R.T. (min) | MS [m/z] [M + H]+ |
|---|---|---|---|---|
| XX-07 | 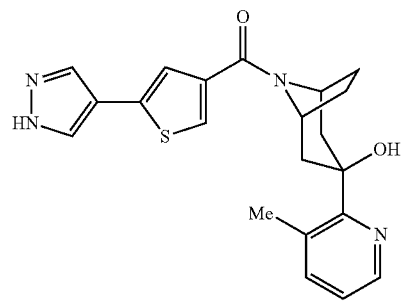 [SMILES: Cc1cccnc1C1(O)CC2CCC(C1)N2C(=O)c1csc(-c2cn[nH]c2)c1] | 1 | 2.28 | 395.1 |
| XX-08 | 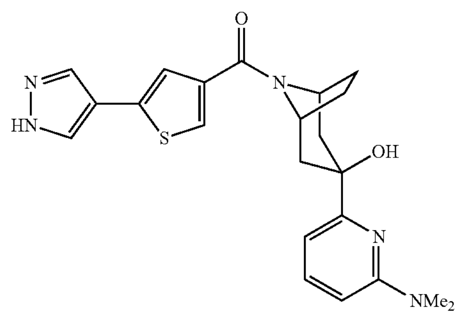 [SMILES: CN(C)c1cccc(C2(O)CC3CCC(C2)N3C(=O)c2csc(-c3cn[nH]c3)c2)n1] | 1 | 2.75 | 424.2 |
| XX-09 | 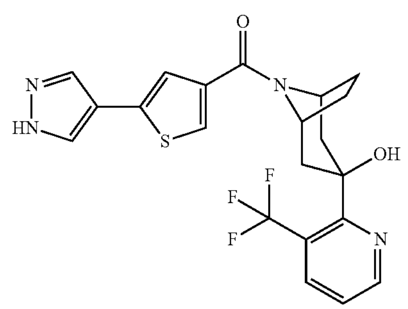 [SMILES: O=C(c1csc(-c2cn[nH]c2)c1)N1C2CCC1CC(O)(c1ncccc1C(F)(F)F)C2] | 1 | 3.88 | 449.2 |
| XX-10 | 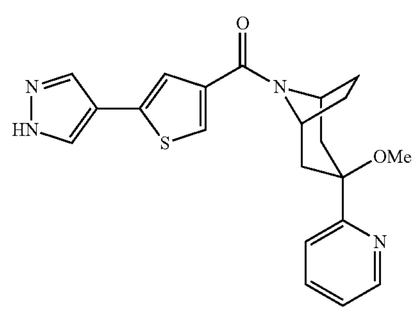 [SMILES: COC1(c2ccccn2)CC2CCC(C1)N2C(=O)c1csc(-c2cn[nH]c2)c1] | 1 | 3.19 | 395.2 |
| XX-11 | 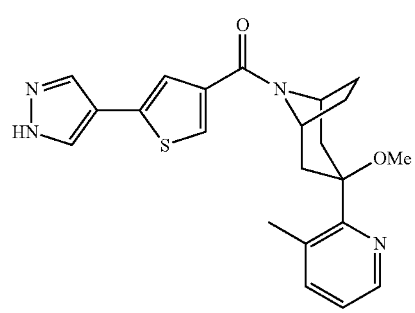 [SMILES: COC1(c2ncccc2C)CC2CCC(C1)N2C(=O)c1csc(-c2cn[nH]c2)c1] | 1 | 3.62 | 409.2 |

-continued
| Cmpd. No. | Structure | Analytical Method | R.T. (min) | MS [m/z] [M + H]+ |
|---|---|---|---|---|
| XX-12 | 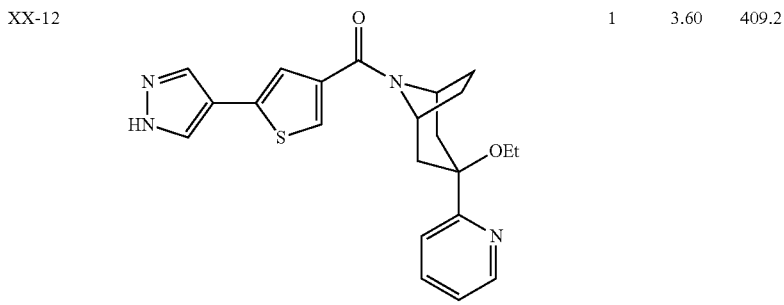 | 1 | 3.60 | 409.2 |
| XX-14 | 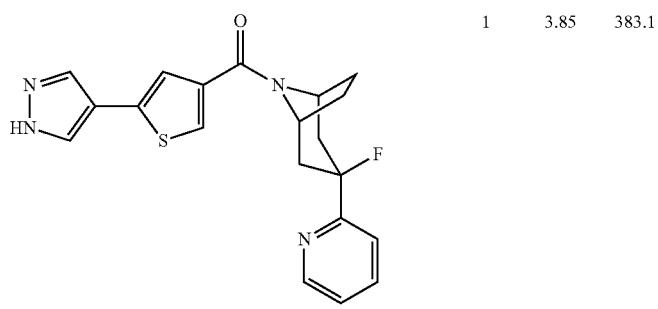  PA Isomer 1 | 1 | 3.85 | 383.1 |
| XX-15 | 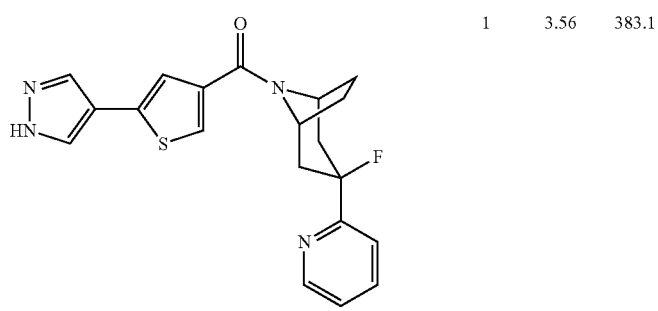  PA Isomer 2 | 1 | 3.56 | 383.1 |
| XX-18 | 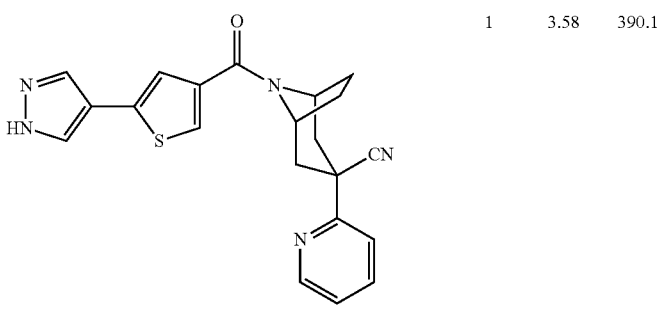 | 1 | 3.58 | 390.1 |

-continued

| Cmpd. No. | Structure | Analytical Method | R.T. (min) | MS [m/z] [M + H]+ |
|---|---|---|---|---|
| XX-19 | 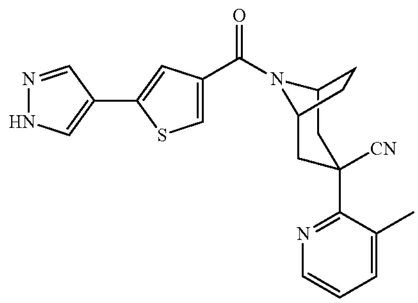 [SMILES: Cc1cccnc1C1(C#N)CC2CCC(C1)N2C(=O)c1csc(-c2cn[nH]c2)c1] | 1 | 3.83 | 404.2 |
| XX-21 | 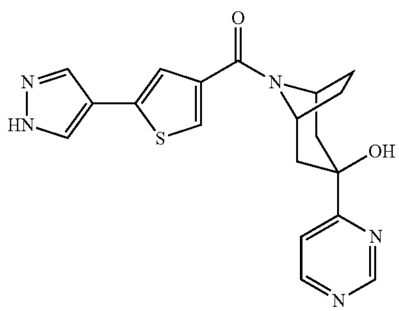 [SMILES: O=C(c1csc(-c2cn[nH]c2)c1)N1C2CCC1CC(O)(c1ccncn1)C2] | 1 | 2.76 | 382.0 |
| XX-22 | 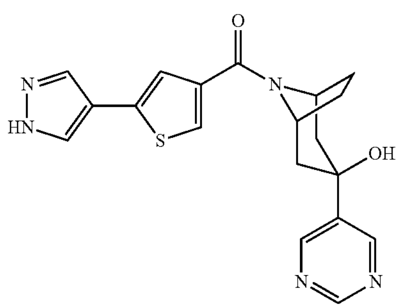 [SMILES: O=C(c1csc(-c2cn[nH]c2)c1)N1C2CCC1CC(O)(c1cncnc1)C2] | 1 | 2.63 | 382.1 |
| XX-23 | 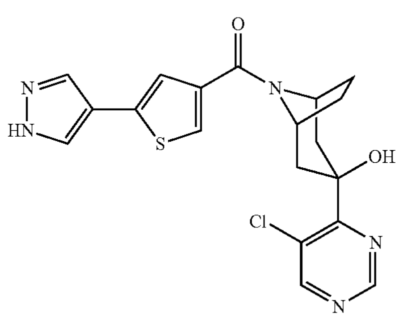 [SMILES: O=C(c1csc(-c2cn[nH]c2)c1)N1C2CCC1CC(O)(c1ncncc1Cl)C2] | 1 | 3.25 | 416.1 |
| XX-24 | 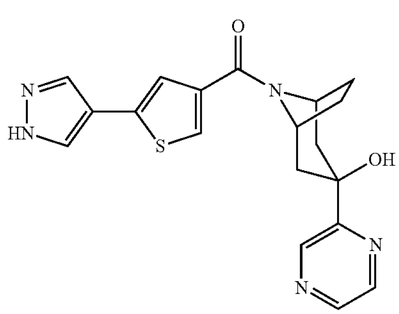 [SMILES: O=C(c1csc(-c2cn[nH]c2)c1)N1C2CCC1CC(O)(c1cnccn1)C2] | 1 | 2.80 | 382.1 |

-continued
| Cmpd. No. | Structure | Analytical Method | R.T. (min) | MS [m/z] [M + H]+ |
|---|---|---|---|---|
| XX-25 | 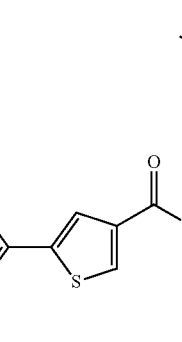 | 1 | 3.23 | 396.2 |
| XX-26 | 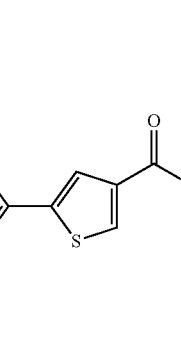 | 1 | 3.22 | 391.1 |
| XX-27 | 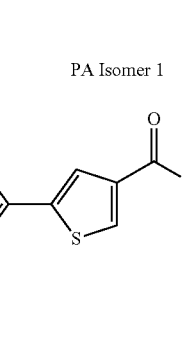  PA Isomer 1 | 1 | 2.66 | 382.1 |
| XX-28 | 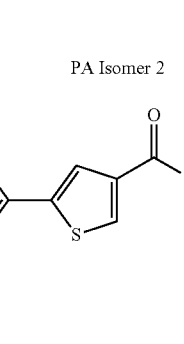  PA Isomer 2 | 1 | 2.60 | 382.1 |
| XX-29 | 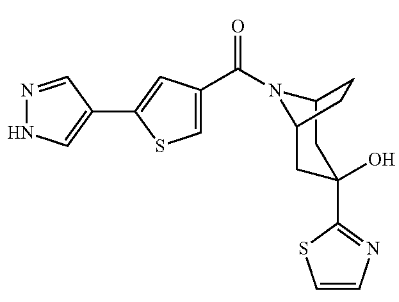 [SMILES: O=C(c1csc(-c2cn[nH]c2)c1)N1C2CCC1CC(O)(c1nccs1)C2] | 1 | 3.00 | 387.9 |

-continued
| Cmpd. No. | Structure | Analytical Method | R.T. (min) | MS [m/z] [M + H]+ |
|---|---|---|---|---|
| XX-30 | 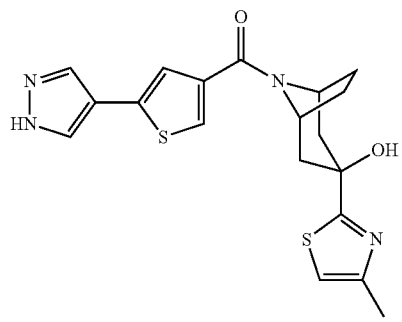<br>PA Isomer 1 | 2 | 6.89 | 401.1 |
| XX-31 | 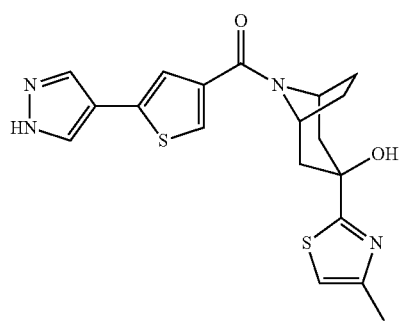<br>PA Isomer 2 | 2 | 7.22 | 401.1 |
| XX-32 | 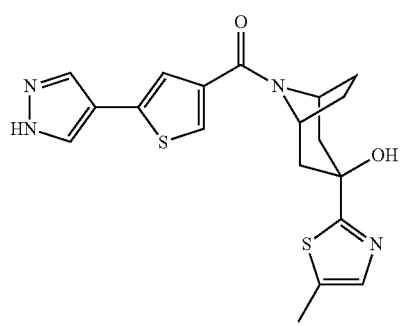<br>PA Isomer 1 | 2 | 7.06 | 401.1 |
| XX-33 | 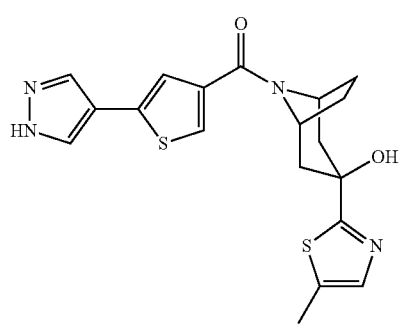<br>PA Isomer 2 | 1 | 3.37 | 401.0 |

-continued

| Cmpd. No. | Structure | Analytical Method | R.T. (min) | MS [m/z] [M + H]+ |
|---|---|---|---|---|
| XX-35 | 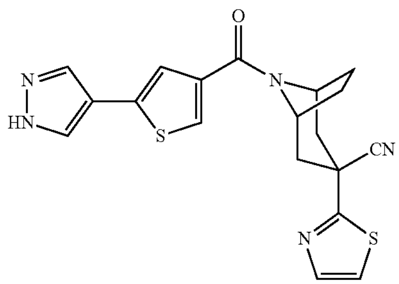 [SMILES: N#CC1(c2nccs2)CC2CCC(C1)N2C(=O)c1csc(-c2cn[nH]c2)c1] | 1 | 3.51 | 396.1 |
| XX-36 | 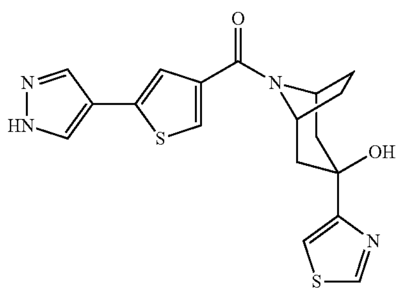 [SMILES: O=C(c1csc(-c2cn[nH]c2)c1)N1C2CCC1CC(O)(c1cscn1)C2] | 1 | 2.90 | 387.1 |
| XX-37 | PA Mixture | 2 | 5.90 6.12 | 371.1 |
| XX-38 | 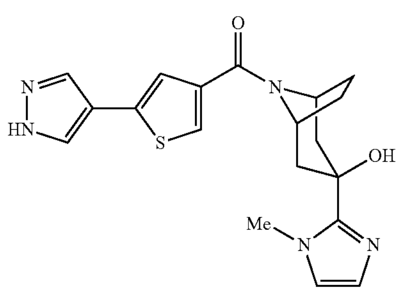 [SMILES: Cn1ccnc1C1(O)CC2CCC(C1)N2C(=O)c1csc(-c2cn[nH]c2)c1] | 1 | 2.22 | 384.1 |
| XX-39 | 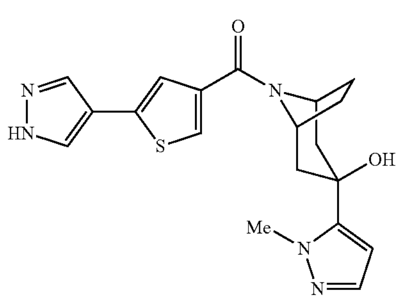 [SMILES: Cn1nccc1C1(O)CC2CCC(C1)N2C(=O)c1csc(-c2cn[nH]c2)c1] | 1 | 2.83 | 384.1 |

-continued

| Cmpd. No. | Structure | Analytical Method | R.T. (min) | MS [m/z] [M + H]+ |
|---|---|---|---|---|
| XX-40 | 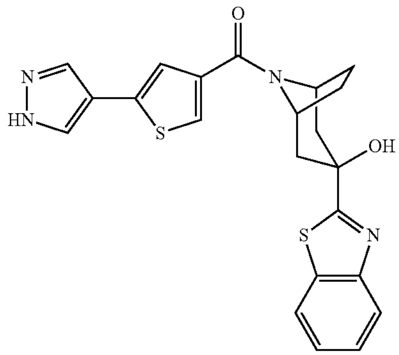 [SMILES: O=C(c1csc(-c2cn[nH]c2)c1)N1C2CCC1CC(O)(c1nc3ccccc3s1)C2] | 2 | 8.59 | 437.1 |
| XX-41 | PA Isomer 1 | 1 | 3.89 | 401.2 |
| XX-42 | PA Isomer 2 | 1 | 3.82 | 401.3 |
| XX-43 | PA Isomer 1 | 1 | 2.96 | 384.2 |

-continued

| Cmpd. No. | Structure | Analytical Method | R.T. (min) | MS [m/z] [M + H]+ |
|---|---|---|---|---|
| YY-01 | 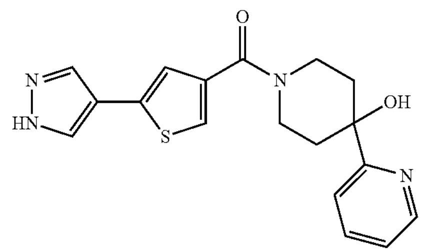 [SMILES: O=C(c1csc(-c2cn[nH]c2)c1)N1CCC(O)(c2ccccn2)CC1] | 1 | 2.15 | 355.1 |
| YY-02 | 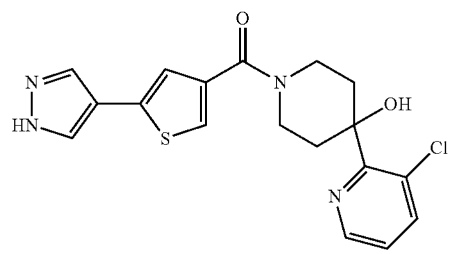 [SMILES: O=C(c1csc(-c2cn[nH]c2)c1)N1CCC(O)(c2ncccc2Cl)CC1] | 1 | 3.37 | 389.0 |
| YY-03 | 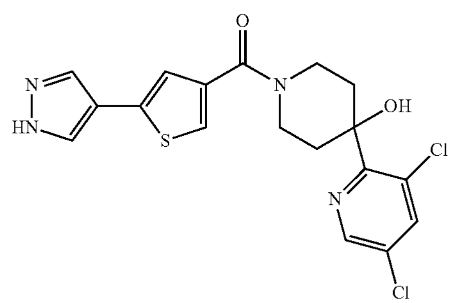 [SMILES: O=C(c1csc(-c2cn[nH]c2)c1)N1CCC(O)(c2ncc(Cl)cc2Cl)CC1] | 1 | 3.97 | 422.9 |
| YY-04 | 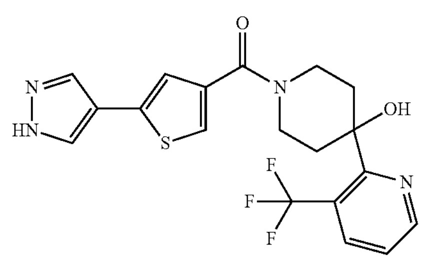 [SMILES: O=C(c1csc(-c2cn[nH]c2)c1)N1CCC(O)(c2ncccc2C(F)(F)F)CC1] | 1 | 3.56 | 423.0 |
| YY-05 | 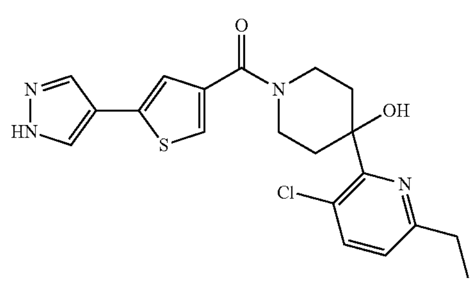 [SMILES: CCc1ccc(Cl)c(C2(O)CCN(C(=O)c3csc(-c4cn[nH]c4)c3)CC2)n1] | 1 | 4.26 | 418.9 |

-continued

| Cmpd. No. | Structure | Analytical Method | R.T. (min) | MS [m/z] [M + H]+ |
|---|---|---|---|---|
| YY-06 | (structure) | 1 | 2.85 | 389.0 |
| YY-07 | (structure) | 1 | 2.63 | 373.0 |
| YY-08 | (structure) | 1 | 3.10 | 373.0 |
| YY-09 | (structure) | 1 | 4.02 | 390.9 |
| YY-10 | (structure) | 1 | 2.66 | 356.0 |
| YY-11 | (structure) | 1 | 2.92 | 358.0 |

NMR data for selected compounds is shown below.

| Cmpd. No. | $^1$H NMR (400 MHz, d6-DMSO): |
|---|---|
| XX-01 | δ 13.1 (s, broad, 1H), 8.5 (d, 1H), 8.15 (s, broad 1H), 7.8 (m, broad, 2H), 7.65 (d, 1H), 7.6 (s, 1H), 7.35 (s, 1H), 7.25 (t, 1H), 5.35 (s, 1H), 4.8-4.4 (m, broad, 2H), 2.6-2.25 (m, broad, 4H), 2.0-1.7 (m, broad, 4H). |
| XX-04 | $^1$H NMR (400 MHz, d6-DMSO): δ 13.1 (s, broad, 1H), 8.55 (d, 1H), 8.5 (s, 1H), 8.0 (s, broad, 2H), 7.75 (d, 1H), 7.65 (s, 1H), 7.3 (s, 1H), 5.6 (s, 1H), 4.8-4.5 (m, broad, 2H), 2.9-2.6 (m, broad, 2H), 2.4-1.8 (m, broad, 6H). |
| XX-05 | δ 13.1 (s, broad, 1H), 8.15 (s, 1H), 7.8 (s, 1H), 7.7 (t, 1H), 7.65 (s, 1H), 7.3 (s, 1H), 7.2 (d, 1H), 6.6 (d, 1H), 5.3 (s, 1H), 4.7-4.4 (m, broad, 2H), 3.8 (s, 3H), 2.6-2.3 (m, broad, 4H), 2.05-1.7 (m, broad, 4H). |
| XX-06 | δ 13.1 (s, broad, 1H), 8.15 (d, 1H), 8.0 (m, broad, 2H), 7.75 (s, 1H), 7.55 (s, 1H), 7.4 (d, 1H), 7.45 (s, 1H), 6.15 (s, 1H), 4.7-4.4 (m, broad, 2H), 3.8 (s, 3H), 2.9-2.6 (m, broad, 4H), 2.1-1.5 (m, broad, 4H). |
| XX-07 | δ 13.1 (s, broad, 1H), 8.35 (d, 1H), 8.0 (m, broad, 2H), 7.75 (s, 1H), 7.6 (d, 1H), 7.3 (s, 1H), 7.25 (t, 1H), 6.05 (s, 1H), 4.8-4.4 (m, broad, 2H), 2.7-2.3 (m, broad, 4H), 2.1-1.8 (m, broad, 4H). |
| XX-09 | $^1$H NMR (400 MHz, d6-DMSO): δ 13.05 (s, broad, 1H), 8.9 (d, 1H), 8.2 (d, 1H), 8.15 (s, broad, 1H), 7.8 (s, broad, 1H), 7.65 (s, 1H), 7.45 (q, 1H), 7.35 (s, 1H), 5.35 (s, 1H), 4.8-4.4 (m, broad, 2H), 2.7-2.6 (m, broad, 2H), 2.4-2.3 (m, broad, 2H), 2.05-1.75 (m, broad, 4H). |
| XX-23 | δ 13.05 (s, broad, 1H), 9.15 (s, 1H), 8.85 (s, 1H), 8.15 (s, broad, 1H), 7.85 (s, broad, 1H), 7.7 (s, 1H), 7.35 (s, 1H), 5.6 (s, 1H), 4.8-4.4 (m, broad, 2H), 2.8-2.3 (m, broad, 4H), 2.01-1.8 (m, broad, 4H). |
| XX-24 | δ 13.05 (s, broad, 1H), 8.95 (s, 1H), 8.6 (d, 1H), 8.5 d, 1H), 8.15 (s, broad, 1H), 7.85 (s, broad, 1H), 7.7 (s, 1H), 7.35 (s, 1H), 5.55 (s, 1H), 4.8-4.6 (m, broad, 2H), 2.6-2.3 (m, broad, 4H), 2.05-1.8 (m, broad, 4H). |
| XX-26 | $^1$H NMR (400 MHz, d6-DMSO): δ 13.1 (s, broad, 1H), 8.9 (d, 2H), 8.15 (s, broad, 1H), 7.85 (s, broad, 1H), 7.7 (s, 1H), 7.55 (t, 1H), 7.35 (s, 1H), 4.9-4.5 (m, broad, 2H), 2.6-2.0 (m, broad, 8H). |
| XX-27 | δ 13.1 (s, broad, 1H), 9.15 (d, 1H), 8.15 (s, 1H), 7.95 (d, 1H), 7.85 (s, 1H), 7.7 (m, 2H), 7.35 (s, 1H), 5.55 (s, 1H), 4.8-4.4 (m, broad, 2H), 2.6-2.3 (m, broad, 4H), 2.1-1.8 (m, broad, 4H). |
| XX-28 | $^1$H NMR (400 MHz, d6-DMSO): δ 13.1 (s, broad, 1H), 9.15 (d, 1H), 8.15 (s, 1H), 8.0 (d, 1H), 7.85 (s, 1H), 7.75 (m, 2H), 7.35 (s, 1H), 5.55 (s, 1H), 4.75-4.35 (m, broad, 2H), 3.0-2.8 (m, broad, 2H), 2.3-2.0 (m, broad, 2H), 1.8-1.2 (m, broad, 4H). |
| XX-29 | δ 13.1 (s, broad, 1H), 8.15 (s, broad, 1H), 7.85 (s, broad, 1H), 7.75 (d, 1H), 7.7 (s, 1H), 7.55 (d, 1H), 7.35 (s, 1H), 6.1 (s, 1H), 4.7-4.4 (m, broad, 2H), 2.6-2.2 (m, broad, 4H), 2.1-1.7 (m, broad, 4H). |
| XX-34 | δ 13.1 (s, broad, 1H), 8.15 (s, 1H), 8.0 (d, 1H), 7.95 (d, 1H), 7.85 (s, 1H), 7.8 (s, 1H), 7.4 (s, 1H), 4.8-4.5 (m, broad, 2H), 2.9-2.4 (m, broad, 4H), 1.9-1.4 (m, broad, 4H). |
| XX-36 | δ 13.1 (s, broad, 1H), 9.0 (s, 1H), 8.1 (s, broad, 1H), 7.9 (s, broad, 1H), 7.75 (s, 1H), 7.45 (s, 1H), 7.3 (s, 1H), 5.35 (s, 1H), 4.7-4.4 (m, broad, 2H), 2.5-2.3 (m, broad, 4H), 2.1-1.7 (m, broad, 4H). |
| XX-39 | δ 13.05 (s, broad, 1H), 8.15 (s, 1H), 7.8 (s, 1H), 7.7 (s, 1H), 7.35 (s, 1H), 7.2 (2, 1H), 6.15 (s, 1H), 5.35 (s, 1H), 4.75-4.35 (m, broad, 2H), 3.95 (s, 3H), 2.4-1.8 (m, broad, 8H). |
| XX-40 | δ 13.05 (s, broad, 1H), 8.15 (s, broad, 1H), 8.1 (d, 1H), 8.05 (d, 1H), 7.85 (s, broad, 1H), 7.75 (s, 1H), 7.55 (t, 1H), 7.45 (t, 1H), 7.35 (s, 1H), 6.1 (s, 1H), 4.8-4.4 (m, broad, 2H), 2.8-2.7 (m, broad, 2H), 2.4-2.2 (m, broad, 2H), 1.9-1.5 (m, broad, 4H). |
| YY-01 | δ 12.5 (s, broad, 1H), 8.55 (d, 1H), 7.95 (m, broad, 1H), 7.8 (m, broad 1H), 7.75 (m, broad, 1H), 7.6 (s, 1H), 7.35 (m, broad, 1H), 7.3 (s, 1H), 5.5 (s, broad, 1H), 4.5-3.0 (m, broad, 4H), 2.2-2.1 (m, broad, 2H), 1.7-1.5 (m, broad, 2H). |
| YY-02 | δ 13.1 (s, broad, 1H), 8.5 (d, 1H), 8.1 (s, broad, 1H), 7.95 (d, 1H), 7.85 (s, broad, 1H), 7.6 (s, 1H), 7.35 (q, 1H), 7.3 (s, 1H), 5.55 (s, 1H), 4.4-3.0 (m, broad, 4H), 2.3-2.2 (m, 2H), 2.0-1.9 (m, broad, 2H). |
| YY-03 | $^1$H NMR (400 MHz, d6-DMSO): δ 13.05 (s, broad, 1H), 8.6 (s, 1H), 8.2 (s, 1H), 8.15 (s, 1H), 7.8 (s, broad, 1H), 7.55 (s, 1H), 7.3 (s, 1H), 5.5 (s, 1H), 4.4-3.2 (m, broad, 4H), 2.2-2.1 (m, broad, 2H), 2.1-1.9 (m, broad, 2H) |
| YY-04 | δ 13.1 (s, broad, 1H), 8.75 (d, 1H), 8.25 (d, 1H), 8.1 (s, broad, 1H), 7.8 (s, broad, 1H), 7.6 (s, 1H), 7.5 (q, 1H), 7.3 (s, 1H), 5.45 (s, broad, 1H), 4.5-3.0 (m, broad, 4H), 2.3-2.1 (m, broad, 2H), 1.9-1.7 (m, broad, 2H). |
| YY-07 | δ 13.0 (s, broad, 1H), 8.5 (d, 1H), 8.45 (d, 1H), 7.95 (broad, 2H), 7.65 (q, 1H), 7.6 (s, 1H), 7.3 (s, 1H), 5.75 (s, 1H), 4.5-3.0 (m, broad, 4H), 2.2-2.0 (m, broad, 2H), 1.8-1.6 (m, broad, 2H). |
| YY-08 | δ 13.1 (s, broad, 1H), 8.4 (m, 1H), 8.1 (s, broad, 1H), 7.8 (s, broad, 1H), 7.7 (q, 1H), 7.55 (s, 1H), 7.45 (m, 1H), 7.3 (s, 1H), 5.5 (s, 1H), 4.4-3.0 (m, broad, 4H), 2.2-2.1 (m, broad, 2H), 2.0-1.8 (m, broad, 2H). |
| YY-09 | $^1$H NMR (400 MHz, d6-DMSO): δ 13.1 (s, broad, 1H), 8.55 (d, 1H), 8.1 (s, broad, 1H), 8.0 (d, 1H), 7.8 (s, broad, 1H), 7.6 (s, 1H), 7.5 (q, 1H), 7.3 (s, 1H), 4.5-3.0 (m, broad, 4H), 2.2-2.1 (m, broad, 4H). |
| YY-10 | δ 12.8 (s, broad, 1H), 9.8 (d, 2H), 7.9 (s, broad, 2H), 7.5 (s, 1H), 7.4 (t, 1H), 7.25 (s, 1H), 4.95 (s, broad, 1H), 4.1-3.9 (m, broad, 2H), 3.5-3.4 (m, broad, 2H), 2.2-2.1 (m, broad, 2H), 1.9-1.75 (m, broad, 2H). |
| YY-11 | δ 13.2 (s, broad, 1H), 9.9 (d, 2H), 7.95 (s, broad, 2H), 7.6 (s, 1H), 7.55 (t, 1H), 7.35 (s, 1H), 4.4-3.0 (m, broad, 4H), 2.4-2.1 (m, broad, 4H). |

Synthesis 2

[3-Fluoro-3-(3-methyl-pyridin-2-yl)-8-aza-bicyclo[3.2.1]oct-8-yl]-[5-(1H-pyrazol-4-yl)-thiophen-3-yl]-methanone (PA Isomer 1: XX-16) and

[3-Fluoro-3-(3-methyl-pyridin-2-yl)-8-aza-bicyclo[3.2.1]oct-8-yl]-[5-(1H-pyrazol-4-yl)-thiophen-3-yl]-methanone (PA Isomer 2: XX-17)

5-(1H-Pyrazol-4-yl)-thiophene-3-carboxylic acid (0.04 g, 0.2 mmol) and 3-fluoro-3-(3-methyl-pyridin-2-yl)-8-aza-bicyclo[3.2.1]octane (PA Mixture) (0.058 g, 0.2 mmol) were dissolved in DMF (3 mL). HATU (0.093 g, 0.24 mmol) and diisopropylethylamine (0.144 mL, 0.89 mmol) were added and the resulting mixture was stirred for 1 hour. Aqueous sodium hydroxide (1 N, 3 mL) was added and the mixture stirred for 0.5 hours. The mixture was diluted with ethyl acetate and washed with brine, dried over magnesium sulphate, filtered and the solvent evaporated under vacuum. The residues were purified by HPLC on a C18 cartridge, eluting with 40%-70% methanol/water with 0.1% formic acid. The fractions containing the desired products were concentrated under vacuum and further lyophilised from methanol and water to give the title compounds.

PA Isomer 1: XX-16: LCMS m/z 397.2 [M+H]+ R.T.=3.93 min (Analytical Method 1). $^1$H NMR (400 MHz, d6-DMSO): b 13.05 (s, broad, 1H), 8.45 (d, 1H), 8.15 (s, broad, 1H), 7.85 (s, broad, 1H), 7.75 (s, 1H), 7.65 (d, 1H), 7.35 (s, 1H), 7.3 (q, 1H), 4.8-4.4 (m, broad, 2H), 2.9-2.8 (m, broad, 2H), 2.6-2.39 (m, broad, 5H), 1.9-1.6 (m, broad, 4H).

PA Isomer 2: XX-17: LCMS m/z 397.2 [M+H]+ R.T.=3.79 min (Analytical Method 1). $^1$H NMR (400 MHz, d6-DMSO): b 13.05 (s, broad, 1H), 8.4 (d, 1H), 8.15 (s, broad, 1H), 7.85 (s, broad, 1H), 7.7 (s, 1H), 7.6 (d, 1H), 7.35 (s, 1H), 7.25 (q, 1H), 4.8-4.4 (m, broad, 2H), 2.8-1.8 (m, broad, 11H).

Synthesis 3

3-Hydroxy-3-pyrimidin-2-yl-8-aza-bicyclo[3.2.1]octane-8-carboxylic acid tert-butyl ester

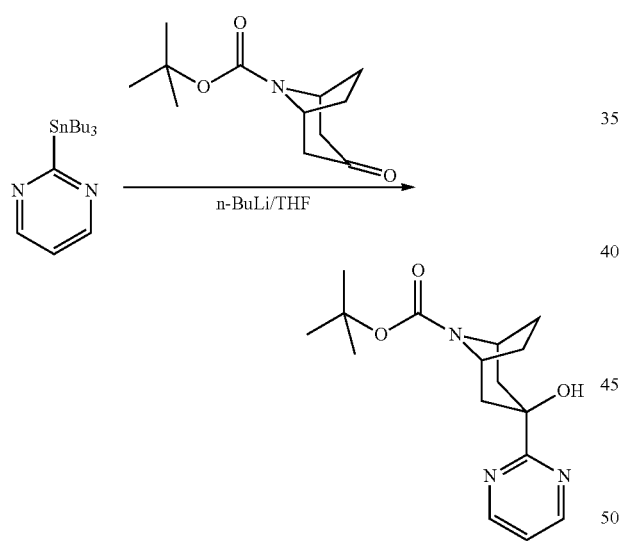

n-Butyl lithium (2.5M, 1.1 mL, 2.77 mmol) was added dropwise to a solution of 2-tributylstannanyl-pyrimidine (1 g, 2.71 mmol) in THF (5 mL), under nitrogen at −78° C. 3-Oxo-8-aza-bicyclo[3.2.1]octane-8-carboxylic acid tert-butyl ester (0.25 g, 1.13 mmol) in THF (2 mL) was added and the reaction mixture stirred at −78° C. for 3 hours. A solution of saturated aqueous ammonium chloride was added and the mixture extracted into ethyl acetate, dried over magnesium sulphate, filtered and the solvent removed by evaporation under vacuum. The residue was purified by flash chromatography on silica eluting with 5-30% ethyl acetate/cyclohexane. The fractions containing the desired product were concentrated under vacuum to give the title compound (0.14 g). LCMS m/z 306.2 [M+H]+. R.T.=3.44 min (Analytical Method 3).

Synthesis 4

3-Pyrimidin-2-yl-8-aza-bicyclo[3.2.1]octan-3-ol hydrochloride

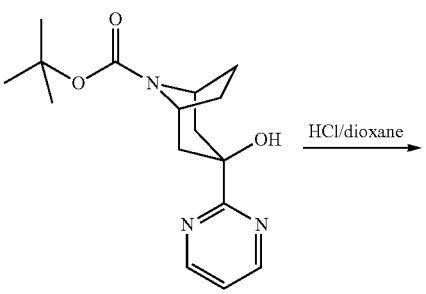

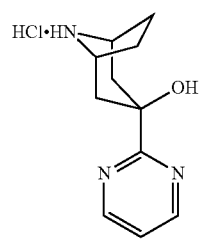

3-Hydroxy-3-pyrimidin-2-yl-8-aza-bicyclo[3.2.1]octane-8-carboxylic acid tert-butyl ester (0.13 g, 0.426 mmol) was dissolved in a solution of hydrogen chloride in dioxane (4 N, 3 mL). The mixture was stirred for 1 hour and the solvent removed by evaporation under vacuum. The solid was triturated from ether to afford the title compound (0.113 g). LCMS m/z 206.1 [M+H]+. R.T.=0.34 min (Analytical Method 3).

The hydrochloride salt of the following substituted piperidine was made by methods analogous to those used to prepare 3-pyrimidin-2-yl-8-aza-bicyclo[3.2.1]octan-3-ol hydrochloride:

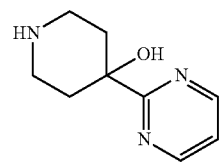

4-Pyrimidin-2-yl-piperidin-4-ol

Synthesis 5

3-(3-Fluoro-pyridin-2-yl)-3-hydroxy-8-aza-bicyclo[3.2.1]octane-8-carboxylic acid tert-butyl ester

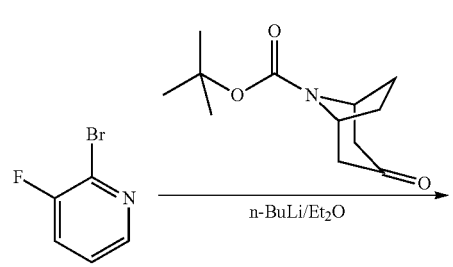

-continued

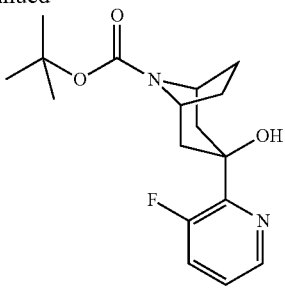

n-Butyl lithium (2.5M, 1 mL, 2.5 mmol) was added dropwise to a solution of 2-bromo-3-fluoro-pyridine (0.4 g, 2.27 mmol) in diethyl ether (8 mL), under nitrogen at −78° C. and stirred for 1 hour. 3-Oxo-8-aza-bicyclo[3.2.1]octane-8-carboxylic acid tert-butyl ester (0.51 g, 2.27 mmol) in diethyl ether (5 mL) was added dropwise at −78° C. and the reaction mixture stirred for 0.5 hours before warming to room temperature. The reaction mixture was poured onto ice, acidified with acetic acid and extracted into ethyl acetate. The remaining aqueous solution was basified with 1 M sodium hydroxide, extracted with DCM and the combined organics were dried over magnesium sulphate, filtered and the solvent removed by evaporation under vacuum. Methanol (10 mL) and sodium borohydride (0.14 g) were added to the residues and stirred for 2 hours to reduce any unreacted ketone. The solvent was removed by evaporation under vacuum, DCM added to the residues and the organics washed with water and brine, dried over magnesium sulphate, filtered and the solvent removed by evaporation under vacuum. The residue was purified by flash chromatography on silica eluting with 5-10% ethyl acetate/cyclohexane. The fractions containing the desired product were concentrated under vacuum to give the title compound (0.25 g). LCMS m/z 323 [M+H]⁺. R.T.=4.67 min (Analytical Method 3).

Synthesis 6

3-(3-Fluoro-pyridin-2-yl)-8-aza-bicyclo[3.2.1]octan-3-ol hydrochloride

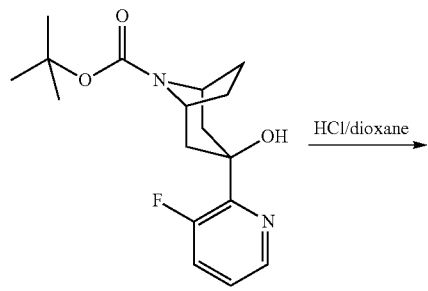

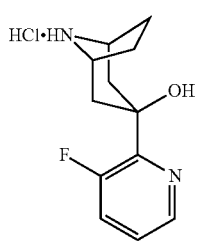

3-(3-Fluoro-pyridin-2-yl)-3-hydroxy-8-aza-bicyclo[3.2.1]octane-8-carboxylic acid tert-butyl ester (0.25 g, 0.775 mmol) was dissolved in a solution of hydrogen chloride in dioxane (4 N, 5 mL). The mixture was stirred for 1 hour and the solvent removed by evaporation under vacuum. The solid was triturated from ether to afford the title compound (0.225 g). ¹H NMR (400 MHz, d6-DMSO): b 9.4 (broad, 1H), 8.85 (s, 1H), 7.8-7.7 (m, 1H), 7.45 (m, 1H), 6.7 (broad), 4.05 (broad, 2H), 2.65-2.55 (m, broad, 2H), 2.45-2.40 (m, broad, 2H), 2.3-2.2 (m, broad, 2H), 2.0-1.9 (m, broad, 2H).

The hydrochloride salts of the following substituted piperidines were made by methods analogous to those used to prepare 3-(3-fluoro-pyridin-2-yl)-8-aza-bicyclo[3.2.1]octan-3-ol hydrochloride:

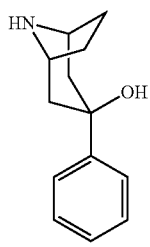

3-Pyrimidin-5-yl-8-aza-bicyclo[3.2.1]octan-3-ol

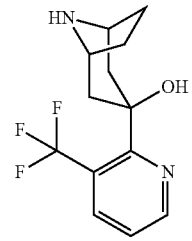

3-(3-Trifluoromethyl-pyridin-2-yl)-8-aza-bicyclo[3.2.1]octan-3-ol

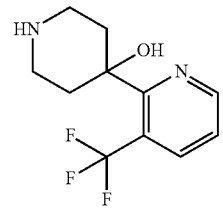

3-Trifluoromethyl-2′,3′,5′,6′-tetrahydro-1′H-[2,4′]bipyridinyl-4′-ol

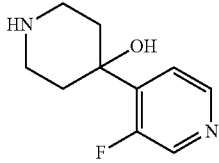

3′-Fluoro-2,3,5,6-tetrahydro-1H[4,4′]bipyridinyl-4-ol

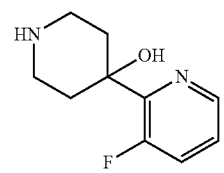

3-Fluoro-2′,3′,5′,6′-tetrahydro-1′H-[2,4′]bipyridinyl-4′-ol

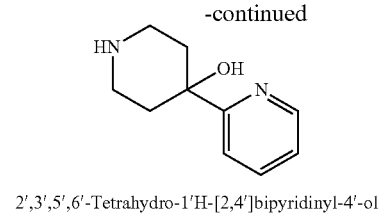

2',3',5',6'-Tetrahydro-1'H-[2,4']bipyridinyl-4'-ol

Synthesis 7

3-Hydroxy-3-(4-methyl-thiazol-2-yl)-8-aza-bicyclo[3.2.1]octane-8-carboxylic acid tert-butyl ester (PA Isomer 1) and 3-Hydroxy-3-(4-methyl-thiazol-2-yl)-8-aza-bicyclo[3.2.1]octane-8-carboxylic acid tert-butyl ester (PA Isomer 2)

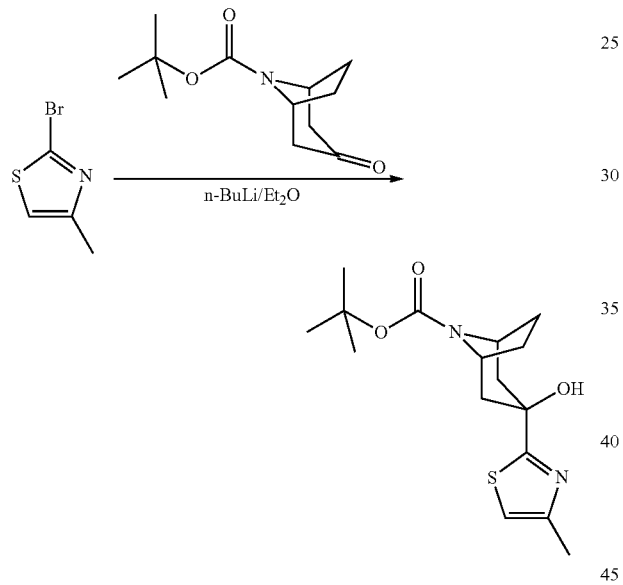

n-Butyl lithium (2.5 M in hexane, 0.33 mL, 0.81 mmol) was added dropwise to a solution of 2-bromo-4-methyl-thiazole (0.13 g, 0.74 mmol) in diethyl ether (2 mL), under nitrogen at −78° C. and stirred for 1 hour. 3-Oxo-8-aza-bicyclo[3.2.1]octane-8-carboxylic acid tert-butyl ester (0.2 g, 0.88 mmol) in diethyl ether (1.5 mL) was added dropwise at −78° C. and the reaction mixture stirred for 0.5 hours before warming to room temperature. The reaction mixture was poured onto ice, acidified with acetic acid and extracted into ethyl acetate. The remaining aqueous solution was basified with 1 M sodium hydroxide, extracted with DCM and the combined organics were dried over magnesium sulphate, filtered and the solvent removed by evaporation under vacuum. Methanol (10 mL) and sodium borohydride (0.14 g) were added to the residues and stirred for 2 hours to reduce any unreacted ketone. The solvent was removed by evaporation under vacuum, DCM added to the residues and the organics washed with water and brine, dried over magnesium sulphate, filtered and the solvent removed by evaporation under vacuum. The residue was purified by flash chromatography on silica eluting with 0-100% ethyl acetate/pentane. The fractions containing the two desired products were concentrated under vacuum to give the title compounds.

PA Isomer 1: (0.13 g). LCMS m/z 325 [M+H]⁺. R.T.=3.62 min (Analytical Method 3).

PA Isomer 2: (0.07 g). LCMS m/z 325 [M+H]⁺. R.T.=3.51 min (Analytical Method 3).

The following substituted piperidines were made by methods analogous to those used to prepare 3-hydroxy-3-(4-methyl-thiazol-2-yl)-8-aza-bicyclo[3.2.1]octane-8-carboxylic acid tert-butyl ester PA Isomer 1 and PA Isomer 2:

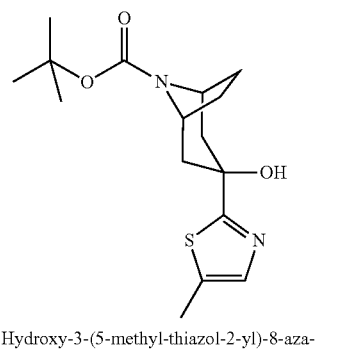

3-Hydroxy-3-(5-methyl-thiazol-2-yl)-8-aza-bicyclo[3.2.1]octane-8-carboxylic acid tert-butyl ester PA Isomer 1

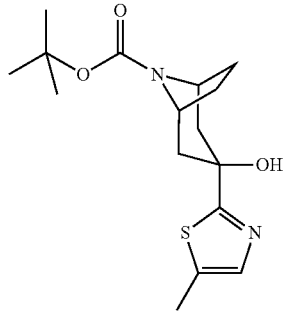

3-Hydroxy-3-(5-methyl-thiazol-2-yl)-8-aza-bicyclo[3.2.1]octane-8-carboxylic acid tert-butyl ester PA Isomer 2

Synthesis 8

3-(4-Methyl-thiazol-2-yl)-8-aza-bicyclo[3.2.1]octan-3-ol PA Isomer 1 hydrochloride

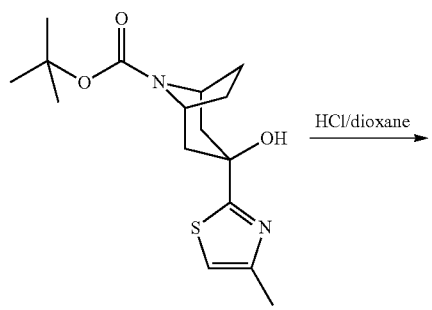

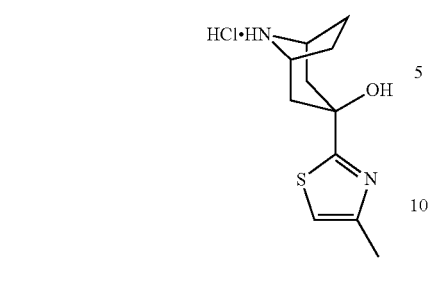

3-Hydroxy-3-(4-methyl-thiazol-2-yl)-8-aza-bicyclo[3.2.1]octane-8-carboxylic acid tert-butyl ester PA Isomer 1 (0.13 g, 0.775 mmol) was dissolved in a solution of hydrogen chloride in dioxane (4 N, 2 mL). The mixture was stirred for 1 hour and the solvent removed by evaporation under vacuum. The solid was triturated from ether to afford the title compound (0.1 g).

The hydrochloride salts of the following substituted piperidines were made by methods analogous to those used to prepare 3-(4-methyl-thiazol-2-yl)-8-aza-bicyclo[3.2.1]octan-3-ol PA Isomer 1 hydrochloride:

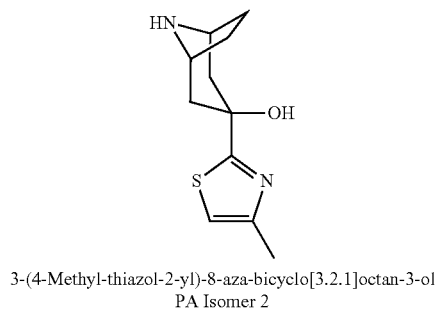

3-(4-Methyl-thiazol-2-yl)-8-aza-bicyclo[3.2.1]octan-3-ol PA Isomer 2

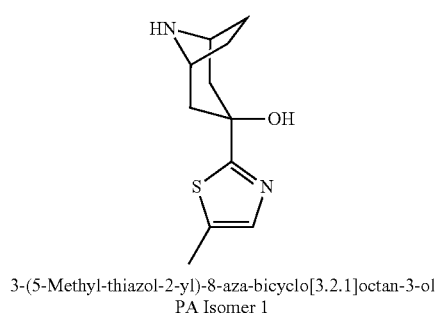

3-(5-Methyl-thiazol-2-yl)-8-aza-bicyclo[3.2.1]octan-3-ol PA Isomer 1

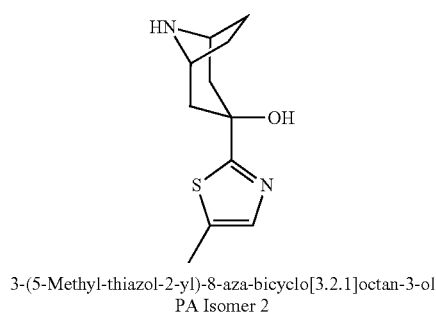

3-(5-Methyl-thiazol-2-yl)-8-aza-bicyclo[3.2.1]octan-3-ol PA Isomer 2

Synthesis 9

3-(3-Chloro-pyridin-2-yl)-3-hydroxy-aza-bicyclo[3.2.1]octane-8-carboxylic acid tert-butyl ester

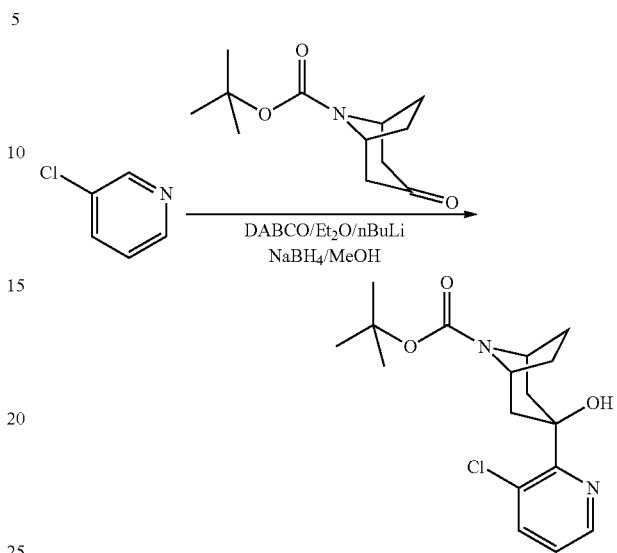

DABCO (0.421 g, 3.7 mmol) in diethyl ether (10 mL) was cooled to −40° C., under nitrogen. Butyl lithium (2.5 M, 0.15 mL) was added dropwise and the mixture stirred for 45 minutes and then cooled to −65° C. 3-Chloropyridine (0.342 mL, 1.1 mmol) was slowly added and the solution stirred for 30 minutes before adding 3-oxo-8-aza-bicyclo[3.2.1]octane-8-carboxylic acid tert-butyl ester in diethyl ether (10 mL). The mixture was allowed to warm to room temperature over 1 hour then saturated aqueous ammonium chloride was added. The mixture was extracted into ethyl acetate, dried over sodium sulphate, filtered and the solvent removed by evaporation under vacuum. Methanol (10 mL) and sodium borohydride (0.148 g, 1.2 mmol) were added to the residues and the mixture stirred for 45 minutes to reduce any unreacted ketone. Saturated aqueous ammonium chloride was added and stirred for 30 minutes then the solvents were removed by evaporation under vacuum. Water and ethyl acetate were added, the organics separated, dried over sodium sulphate, filtered and the solvent removed by evaporation under vacuum. The residue was purified by flash chromatography on silica eluting with 5-10% ethyl acetate/cyclohexane. The fractions containing the desired product were concentrated under vacuum to give the title compound (0.370 g). LCMS m/z 285.3 [M+H]$^+$. R.T.=4.85 min (Analytical Method 3).

Synthesis 10

3-(3-Chloro-pyridin-2-yl)-8-aza-bicyclo[3.2.1]octan-3-ol hydrochloride

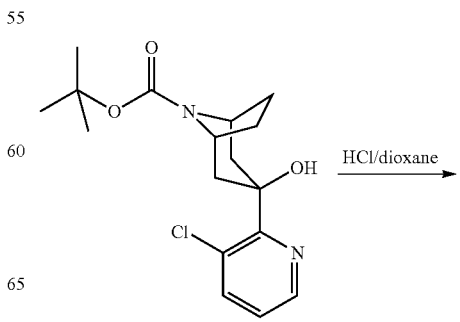

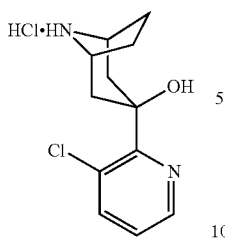

3-(3-Chloro-pyridin-2-yl)-3-hydroxy-aza-bicyclo[3.2.1]octane-8-carboxylic acid tert-butyl ester (0.115 g, 0.34 mmol) was dissolved in a solution of hydrogen chloride in dioxane (4 N, 1 mL). The mixture was stirred for 1 hour and the solvent removed by evaporation under vacuum. The product was used without further purification. LCMS m/z 239.3 [M+H]⁺. R.T.=1.62 min (Analytical Method 3).

Synthesis 11

3-Hydroxy-3-(1-methyl-1H-imidazol-2-yl)-8-aza-bicyclo[3.2.1]octane-8-carboxylic acid tert-butyl ester

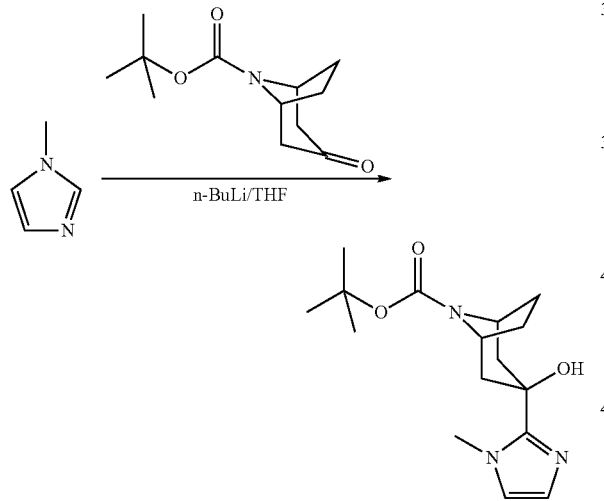

n-Butyl lithium (2.5 M, 1 mL, 2.5 mmol) was added dropwise to a solution of 1-methyl imidazole (0.193 g, 2.35 mmol) in THF (10 mL), under nitrogen at −78° C. 3-Oxo-8-aza-bicyclo[3.2.1]octane-8-carboxylic acid tert-butyl ester (0.55 g, 2.45 mmol) in THF (2.5 mL) was added and the mixture stirred at −78° C. for 1 hour before warming to room temperature. A solution of saturated aqueous ammonium chloride was added and the mixture extracted into ethyl acetate, dried over magnesium sulphate, filtered and the solvent removed by evaporation under vacuum. The residue was purified by flash chromatography on silica eluting with 1:1 ethyl acetate/cyclohexane. The fractions containing the desired product were concentrated under vacuum to give the title compound (0.12 g). LCMS m/z 308.2 [M+H]⁺. R.T.=2.14 min (Analytical Method 3).

Synthesis 12

3-(1-methyl-1H-imidazol-2-yl)-8-aza-bicyclo[3.2.1]octan-3-ol hydrochloride

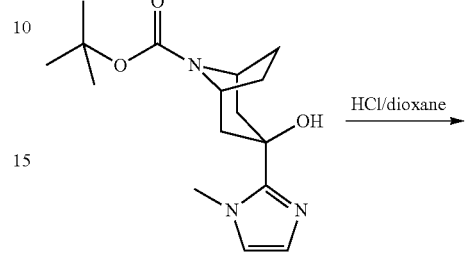

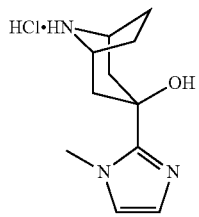

3-Hydroxy-3-(1-methyl-1H-imidazol-2-yl)-8-aza-bicyclo[3.2.1]octane-8-carboxylic acid tert-butyl ester (0.12 g) was dissolved in a solution of hydrogen chloride in dioxane (4 N, 1.5 mL). The mixture was stirred for 1 hour and the solvent removed by evaporation under vacuum. The solid was triturated from ether to afford the title compound (0.09 g) which was used without further purification.

The hydrochloride salts of the following substituted piperidines were made by methods analogous to those used to prepare 3-(1-methyl-1H-imidazol-2-yl)-8-aza-bicyclo[3.2.1]octan-3-ol hydrochloride:

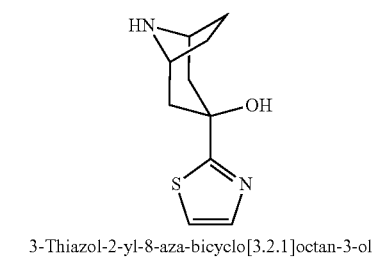

3-Thiazol-2-yl-8-aza-bicyclo[3.2.1]octan-3-ol

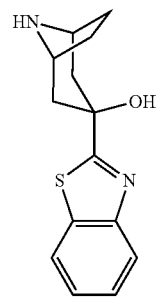

3-Benzothiazol-2-yl-8-aza-bicyclo[3.2.1]octan-3-ol

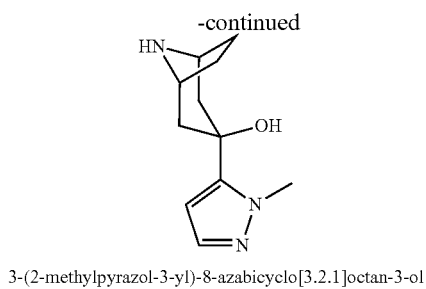

3-(2-methylpyrazol-3-yl)-8-azabicyclo[3.2.1]octan-3-ol

Synthesis 13

8-Benzyl-3-(5-bromo-pyrimidin-4-yl)-8-aza-bicyclo[3.2.1]octan-3-ol

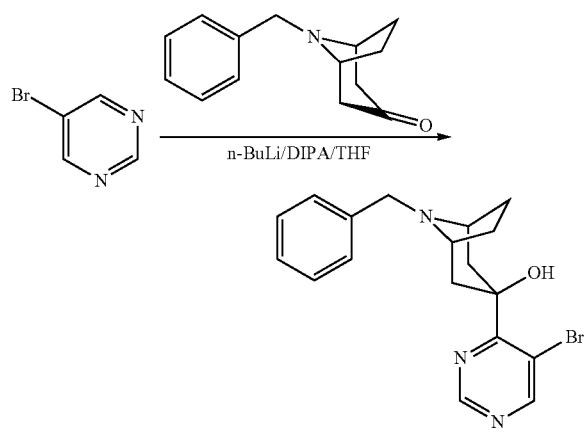

n-Butyl lithium (2.5M, 1.2 mL, 3.00 mmol) was added dropwise to a solution of diisopropylamine (0.406 mL, 3.0 mmol) in THF (5 mL) at 0° C. under nitrogen and stirred for 30 minutes. The mixture was then added to a solution of 8-benzyl-8-aza-bicyclo[3.2.1]octan-3-one (0.64 g, 3.0 mmol) and 5-bromopyrimidine (0.477 g, 3.0 mmol) in THF (5 mL) and stirred at 0° C. for 1 hour. Water and ethyl acetate were added, the organics separated, dried over sodium sulphate, filtered and the solvent removed by evaporation under vacuum. The residue was purified by flash chromatography on silica eluting with 20-50% ethyl acetate/cyclohexane. The fractions containing the desired product were concentrated under vacuum to give the title compound. LCMS m/z 374.2 [M+H]⁺. R.T.=2.06 min (Analytical Method 3).

Synthesis 14

3-(5-bromo-pyrimidin-4-yl)-8-aza-bicyclo[3.2.1]octan-3-ol

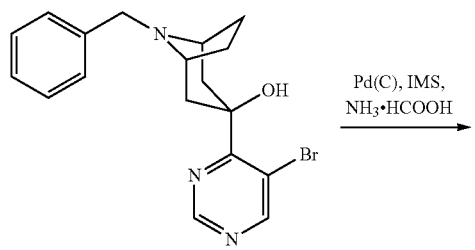

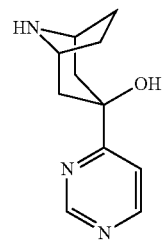

8-Benzyl-3-(b-bromo-pyrimidin-4-yl)-8-aza-bicyclo[3.2.1]octan-3-ol (0.90 g, 2.4 mmol) was dissolved in IMS (20 mL) and water (1 mL). Palladium on carbon (10%; 0.40 g) was added under nitrogen. Ammonium formate (1.5 g, 24 mmol) was added and the mixture heated at reflux for 0.5 hour. The mixture was allowed to cool, filtered and the solvent removed by evaporation under vacuum. The residues were passed through an SCX cartridge, eluting with 2 M ammonia in methanol to give the title compound as a colourless oil (0.30 g).

Synthesis 15

8-Benzyl-3-pyrazin-2-yl-8-aza-bicyclo[3.2.1]octan-3-ol

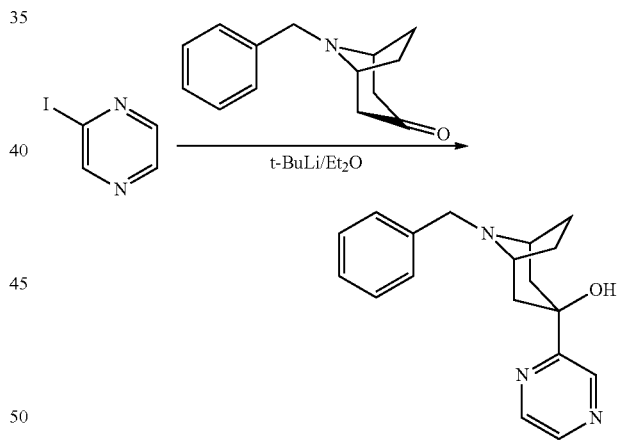

t-Butyl lithium (1.7 M, 1.18 mL, 2.00 mmol) was added dropwise to a solution of 2-iodopyrazine (0.1 mL, 1.0 mmol) in diethyl ether (10 mL) at −78° C. under nitrogen and stirred for 30 minutes. A solution of 8-benzyl-8-aza-bicyclo[3.2.1]octan-3-one (0.19 g, 0.88 mmol) in diethyl ether (5 mL) was added dropwise and stirred at −78° C. for 1 hour. It was warmed to room temperature, water and ethyl acetate were added, the organics separated, dried over sodium sulphate, filtered and the solvent removed by evaporation under vacuum. The residue was purified by flash chromatography on silica eluting with 1:1 ethyl acetate/cyclohexane. The fractions containing the desired product were concentrated under vacuum to give the title compound (0.06 g). LCMS m/z 296.3 [M+H]⁺. R.T.=1.97 min (Analytical Method 3).

Synthesis 16

3-Pyrazin-2-yl-8-aza-bicyclo[3.2.1]octan-3-ol

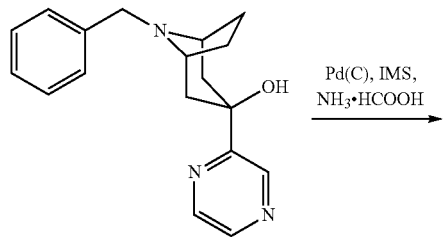

8-Benzyl-3-pyrazin-2-yl-8-aza-bicyclo[3.2.1]octan-3-ol (0.25 g, 0.85 mmol) was dissolved in IMS (10 mL) and water (1 mL). Palladium on carbon (10%; 0.1 g) was added under nitrogen. Ammonium formate (0.58 g, 9.2 mmol) was added and the mixture heated at reflux for 1 hour. The mixture was allowed to cool, filtered and the solvent removed by evaporation under vacuum. The residues were passed through an SCX cartridge, eluting with 2 M ammonia in methanol to give the title compound as a colourless oil (0.11 g). LCMS m/z 206.2 [M+H]$^+$. R.T.=0.34 min (Analytical Method 3).

Synthesis 17

3-Hydroxy-3-(3-methyl-pyrazin-2-yl)-8-aza-bicyclo[3.2.1]octane-8-carboxylic acid tert-butyl ester

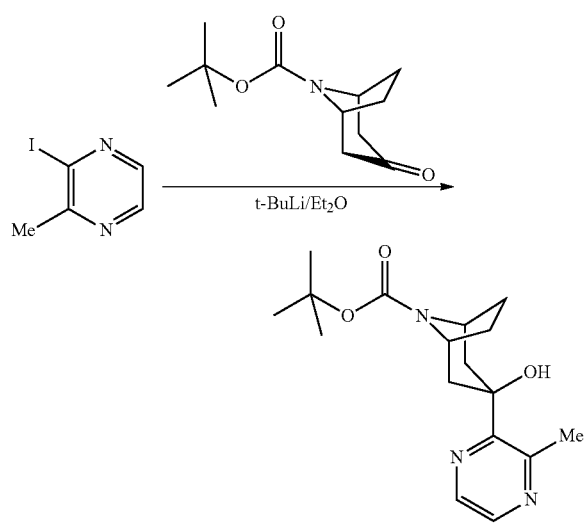

t-Butyl lithium in pentane (1.7 M, 3.8 mL, 6.46 mmol) was added dropwise to a solution of 2-iodo-3-methylpyrazine (0.7 g, 3.18 mmol) in diethyl ether (20 mL) at −50° C. under nitrogen and stirred for 30 minutes. A solution of 3-oxo-8-aza-bicyclo[3.2.1]octane-8-carboxylic acid tert-butyl ester (0.19 g, 0.88 mmol) in diethyl ether (10 mL) was added dropwise and stirred at −50° C. for 1 hour. The reaction mixture was warmed to room temperature, water and ethyl acetate were added, the organics separated, dried over sodium sulphate, filtered and the solvent removed by evaporation under vacuum. The residue was purified by flash chromatography on silica eluting with ethyl acetate/cyclohexane. The fractions containing the desired product were concentrated under vacuum to give the title compound (0.1 g) as a pale yellow oil. LCMS m/z 320.2 [M+H]$^+$. R.T.=3.55 min (Analytical Method 3).

Synthesis 18

3-(3-Methyl-pyrazin-2-yl)-8-aza-bicyclo[3.2.1]octan-3-ol

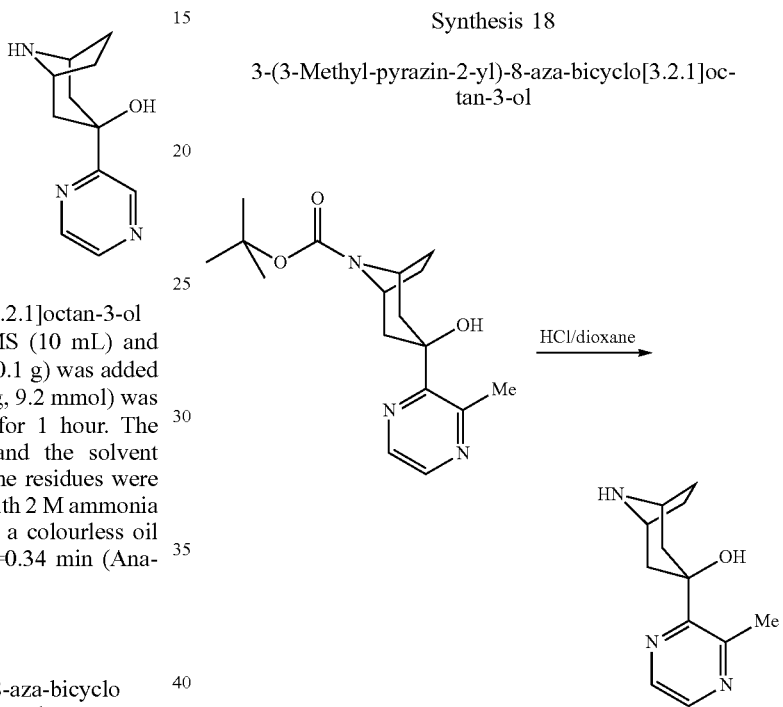

3-Hydroxy-3-(3-methyl-pyrazin-2-yl)-8-aza-bicyclo[3.2.1]octane-8-carboxylic acid tert-butyl ester (0.1 g, 0.41 mmol) was dissolved in a solution of hydrogen chloride in dioxane (4 N, 1.5 mL). The mixture was stirred for 1 hour and the solvent removed by evaporation under vacuum to afford the title compound. LCMS m/z 220.1 [M+H]$^+$. R.T.=0.34 min (Analytical Method 3).

Synthesis 19

3-(5-Chloro-pyrimidin-4-yl)-3-hydroxy-8-aza-bicyclo[3.2.1]octane-8-carboxylic acid tert-butyl ester

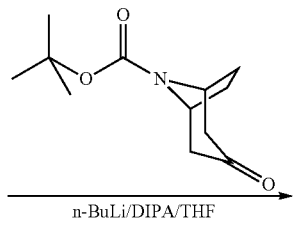

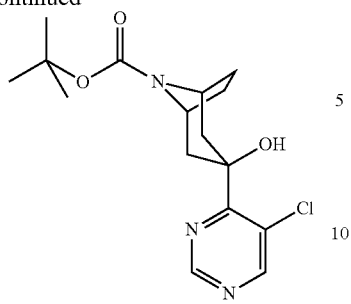

n-Butyl lithium (2.5 M, 1.2 mL, 3.00 mmol) was added dropwise to a solution of diisopropylamine (0.406 mL, 3.0 mmol) in THF (5 mL) at 0° C. under nitrogen and stirred for 30 minutes. The mixture was then added to a solution of 3-oxo-8-aza-bicyclo[3.2.1]octane-8-carboxylic acid tert-butyl ester (0.675 g, 3.0 mmol) and 5-chloropyrimidine (0.343 g, 3.0 mmol) in THF (1.5 mL) and stirred at 0° C. for 1 hour. Water and ethyl acetate were added, the organics separated, dried over sodium sulphate, filtered and the solvent removed by evaporation under vacuum. The residue was purified by flash chromatography on silica eluting with 20-30% ethyl acetate/cyclohexane. The fractions containing the desired product were concentrated under vacuum to give the title compound (0.14 g). LCMS m/z 340.3 [M+H]$^+$. R.T.=3.70 min (Analytical Method 3).

Synthesis 20

3-(5-Chloro-pyrimidin-4-yl)-8-aza-bicyclo{3.2.1} octan-3-ol hydrochloride

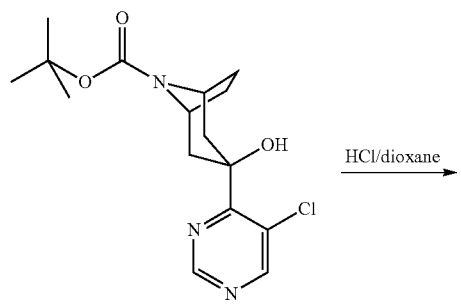

3-(5-Chloro-pyrimidin-4-yl)-3-hydroxy-8-aza-bicyclo{3.2.1}octane-8-carboxylic acid tert-butyl ester (0.14 g, 0.41 mmol) was dissolved in a solution of hydrogen chloride in dioxane (4 N, 2 mL). The mixture was stirred for 1 hour and the solvent removed by evaporation under vacuum to afford the title compound. LCMS m/z 240.3 [M+H]$^+$. R.T.=0.36 min (Analytical Method 3).

Synthesis 21

3-Hydroxy-3-pyridin-2-yl-8-aza-bicyclo[3.2.1]octane-8-carboxylic acid tert-butyl ester

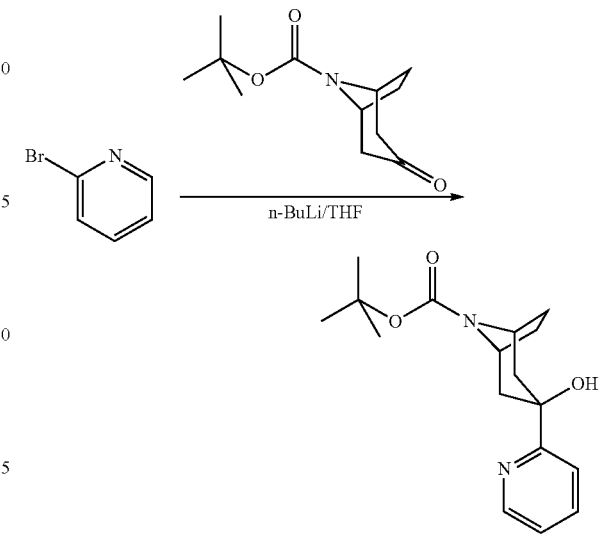

n-Butyl lithium (2.5 M, 2.4 mL, 6.0 mmol) was added dropwise to a solution of 2-bromopyridine (0.57 mL, 6.0 mmol) in THF (10 mL) at −78° C. under nitrogen and stirred for 30 minutes. A solution of 3-oxo-8-aza-bicyclo[3.2.1]octane-8-carboxylic acid tert-butyl ester (1.3 g, 5.78 mmol) in THF (10 mL) was added dropwise and the mixture stirred at −78° C. for 1 hour. The reaction mixture was warmed to room temperature then saturated aqueous sodium hydrogen carbonate and ethyl acetate were added, the organics separated, dried over magnesium sulphate, filtered and the solvent removed by evaporation under vacuum. The residue was purified by flash chromatography on silica eluting with 20-50% ethyl acetate/pentane. The fractions containing the desired product were concentrated under vacuum to give the title compound (0.62 g). LCMS m/z 305.3 [M+H]$^+$. R.T.=2.50 min (Analytical Method 3).

Synthesis 22

3-Pyridin-2-yl-8-aza-bicyclo[3.2.1]octan-3-ol

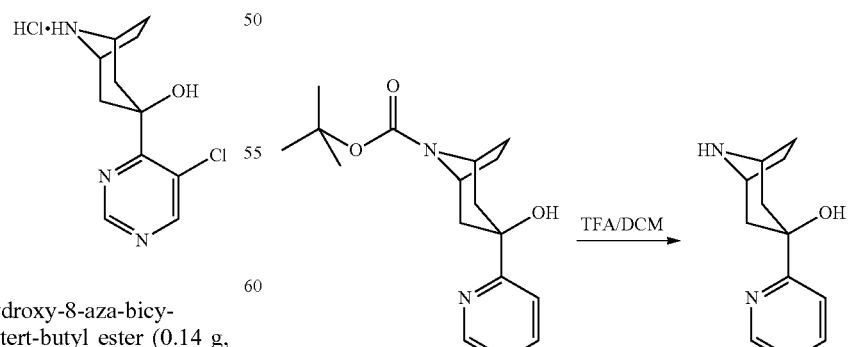

3-Hydroxy-3-pyridin-2-yl-8-aza-bicyclo[3.2.1]octane-8-carboxylic acid tert-butyl ester (0.8 g, 2.6 mmol) was dissolved in TFA (3 mL) and DCM (10 mL). The mixture was stirred for 1 hour and the solvent removed by evaporation under vacuum and the residues were passed through an SCX cartridge, eluting with 2 M ammonia in methanol to give the title compound. LCMS m/z 205.2 [M+H]⁺. R.T.=0.38 min (Analytical Method 3).

The following substituted piperidines were made by methods analogous to those used to prepare 3-pyridin-2-yl-8-aza-bicyclo[3.2.1]octan-3-ol:

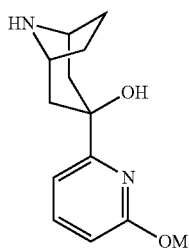

3-(6-Methoxy-pyridin-2-yl)-8-aza-bicyclo[3.2.1]octan-3-ol

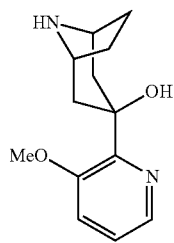

3(3-Methoxy-pyridin-2-yl)-8-aza-bicyclo[3.2.1]octan-3-ol

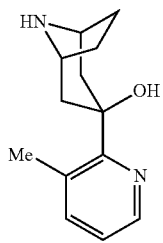

3(3-Methyl-pyridin-2-yl)-8-aza-bicyclo[3.2.1]octan-3-ol

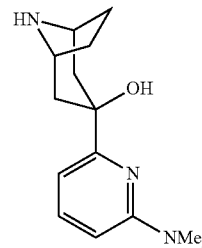

3-(6-Dimethylamino-pyridin-2-yl)-8-aza-bicyclo[3.2.1]octan-3-ol

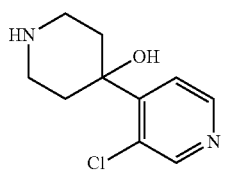

4-(3-chloro-4-pyridyl)piperidin-4-ol

Synthesis 23

3-Hydroxy-3-oxazol-2-yl-8-aza-bicyclo[3.2.1]octane-8-carboxylic acid tert-butyl ester PA Mixture

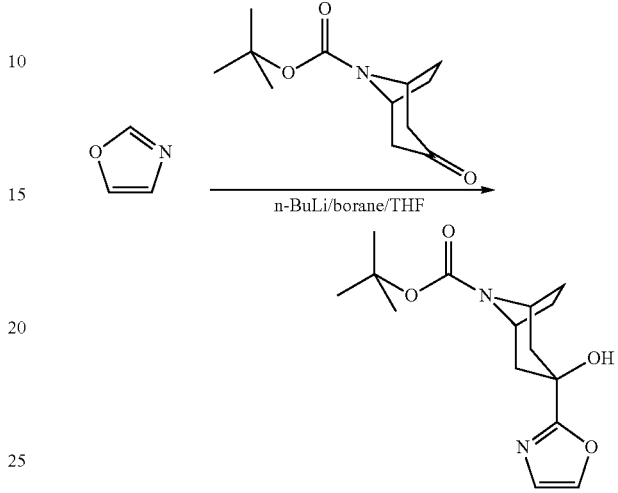

Borane-THF complex (1 M, 4.5 mL, 4.5 mmol) was added to a solution of oxazole (0.3 mL, 4.5 mmol) in THF (5 mL) and stirred for 1 hour under nitrogen before cooling to −78° C. n-Butyl lithium (2.5M, 1.8 mL, 4.5 mmol) was added and the reaction mixture stirred for a further 30 minutes. A solution of 3-oxo-8-aza-bicyclo[3.2.1]octane-8-carboxylic acid tert-butyl ester (0.675 g, 3.0 mmol) in THF (5 mL) was added and the reaction mixture stirred for 30 minutes. 10% acetic acid in IMS (10 mL) was added and the reaction mixture warmed to room temperature and then further to 40° C. for 30 minutes. The solvent was removed by evaporation under vacuum, water and ethyl acetate were added to the residues, the organics extracted, dried over magnesium sulphate, filtered and evaporated to dryness. The residue was purified by flash chromatography on silica eluting with 25-60% ethyl acetate/cyclohexane. The fractions containing the desired product were concentrated under vacuum to give the title compound (0.3 g) as a colourless oil. LCMS m/z 295.2 [M+H]⁺. R.T.=3.07 min (Analytical Method 3).

Synthesis 24

3-Oxazol-2-yl-8-aza-bicyclo[3.2.1]octan-3-ol hydrochloride PA Mixture

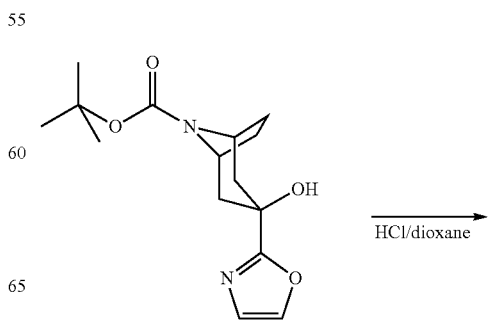

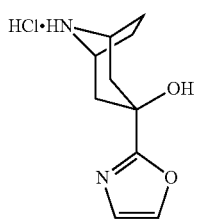

3-Hydroxy-3-oxazol-2-yl-8-aza-bicyclo[3.2.1]octane-8-carboxylic acid tert-butyl ester (0.3 g) was dissolved in a solution of hydrogen chloride in dioxane (4 N, 4 mL). The mixture was stirred for 1 hour and the solvent removed by evaporation under vacuum. The solid was triturated from ether to afford the title compound (0.28 g). LCMS m/z 195.2 [M+H]$^+$. R.T.=0.35 min (Analytical Method 3).

Synthesis 25

3-Hydroxy-3-pyridazin-3-yl-8-aza-bicyclo[3.2.1]octane-8-carboxylic acid tert-butyl ester PA Isomer 1 and 3-Hydroxy-3-pyridazin-3-yl-8-aza-bicyclo[3.2.1]octane-8-carboxylic acid tert-butyl ester PA Isomer 2

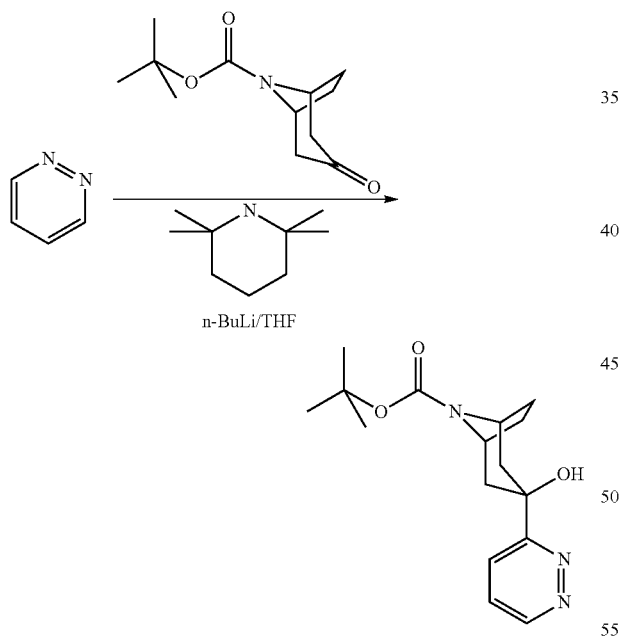

n-Butyl lithium (1.8 mL, 4.5 mmol) was added to a solution of 2,2,6,6-tetramethylpiperidine (0.76 mL, 4.5 mmol) in THF (25 mL) at −30° C., warmed to 0° C. and stirred for 30 minutes. After cooling to −78° C., a solution of 3-oxo-8-aza-bicyclo[3.2.1]octane-8-carboxylic acid tert-butyl ester (0.675 g, 3.0 mmol) and pyridazine (0.29 mL, 4. mmol) in THF (5 mL) was added dropwise and stirred for 1 hour. A solution of saturated aqueous ammonium chloride was added and the mixture extracted into ethyl acetate, dried over magnesium sulphate, filtered and the solvent removed by evaporation under vacuum. The residue was purified by flash chromatography on silica eluting with 60-100% ethyl acetate/cyclohexane. The fractions containing the two desired products were concentrated under vacuum to give the title compounds.

PA Isomer 1: LCMS m/z 306.3 [M+H]$^+$. R.T.=2.91 min (Analytical Method 3).

PA Isomer 2: LCMS m/z 306.3 [M+H]$^+$. R.T.=2.78 min (Analytical Method 3).

Synthesis 26

3-Pyridazin-3-yl-8-aza-bicyclo[3.2.1]octan-3-ol hydrochloride PA Isomer 1

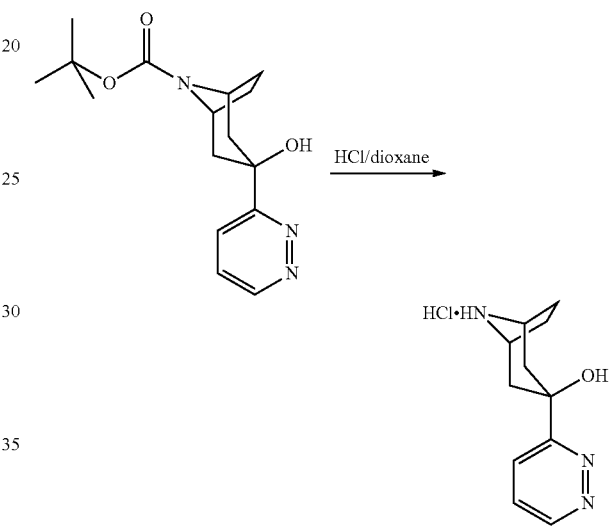

3-Hydroxy-3-pyridazin-3-yl-8-aza-bicyclo[3.2.1]octane-8-carboxylic acid tert-butyl ester (0.22 g) was dissolved in a solution of hydrogen chloride in dioxane (4 N, 2.5 mL). The mixture was stirred for 0.5 hours and the solvent removed by evaporation under vacuum. The solid was triturated from ether to afford the title compound (0.22 g). LCMS m/z 206.2 [M+H]$^+$. R.T.=0.35 min. (Analytical Method 3).

The hydrochloride salt of the following substituted piperidine was made by methods analogous to those used to prepare 3-pyridazin-3-yl-8-aza-bicyclo[3.2.1]octan-3-ol hydrochloride PA Isomer 1:

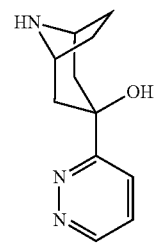

3-Pyridazin-3-yl-8-aza-bicyclo[3.2.1]octan-3-ol PA Isomer 2

Synthesis 27

3-Hydroxy-3-thiazol-4-yl-8-aza-bicyclo[3.2.1]octane-8-carboxylic acid tert-butyl ester

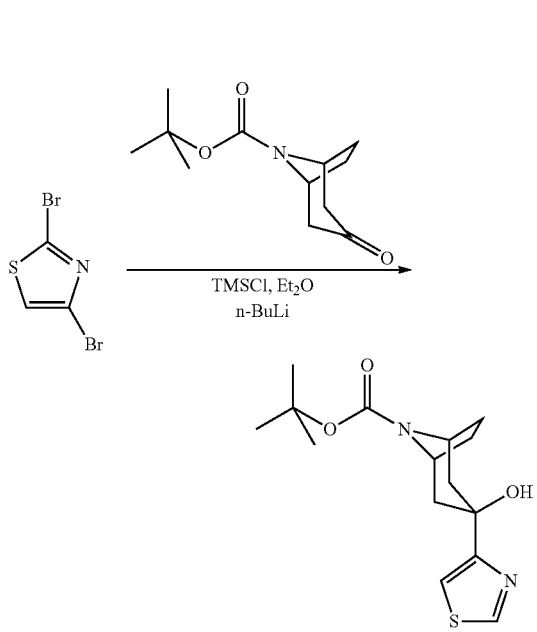

2,4-dibromothiazole (1.1 g, 4.52 mmol) in diethyl ether (5 mL) was added to a solution of n-butyl lithium (2.5 M, 2 mL, 5 mmol) in diethyl ether (10 mL) at −78° C. and stirred for 0.5 hours. Trimethylsiliyl chloride (0.57 mL, 4.52 mmol) was added and the reaction mixture stirred for a further 0.5 hours before more n-butyl lithium (2.5M, 2 mL, 5 mmol) was added and stirred for 0.5 hours. 3-Oxo-8-aza-bicyclo[3.2.1]octane-8-carboxylic acid tert-butyl ester (0.9 g, 4 mmol) in diethyl ether (5 mL) was added and stirred for 0.5 hours before the reaction mixture was warmed to room temperature. Saturated aqueous ammonium chloride was added and the mixture extracted into ethyl acetate, dried over magnesium sulphate, filtered and the solvent removed by evaporation under vacuum. The residue was purified by flash chromatography on silica eluting with 20-30% ethyl acetate/cyclohexane. The fractions containing the desired product were concentrated under vacuum to give the title compound (0.22 g). LCMS m/z 311.3 [M+H]+. R.T.=3.05 min. (Analytical Method 3).

Synthesis 28

3-Thiazol-4-yl-8-aza-bicyclo[3.2.1]octan-3-ol hydrochloride

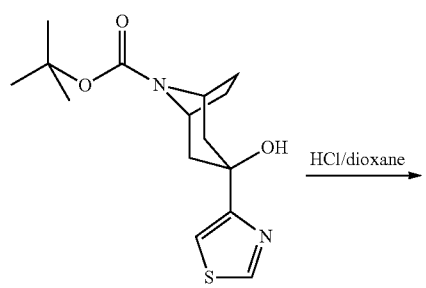

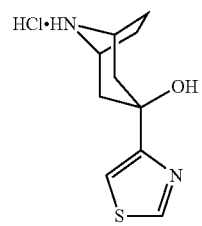

3-Hydroxy-3-thiazol-4-yl-8-aza-bicyclo[3.2.1]octane-8-carboxylic acid tert-butyl ester (0.22 g) was dissolved in a solution of hydrogen chloride in dioxane (4 N, 2.5 mL). The mixture was stirred for 0.5 hours at 45° C. and the solvent removed by evaporation under vacuum. The solid was triturated from ether to afford the title compound (0.20 g). LCMS m/z 211.1 [M+H]+. R.T.=0.35 min. (Analytical Method 3).

Synthesis 29

3-(3-Chloro-pyridin-4-yl)-3-hydroxy-8-aza-bicyclo[3.2.1]octane-8-carboxylic acid tert-butyl ester

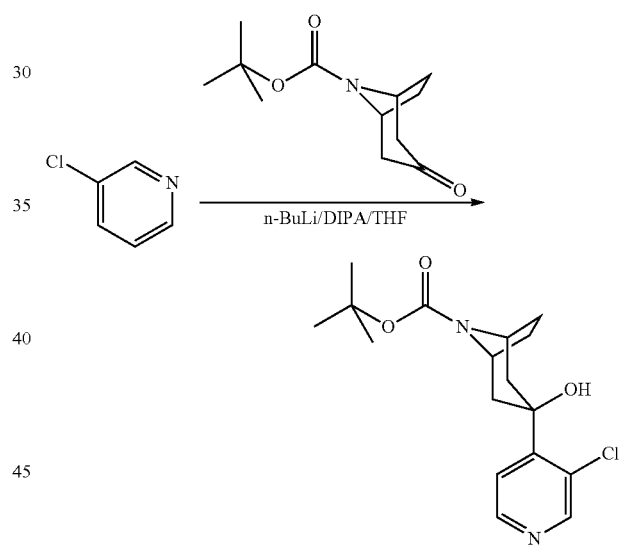

n-Butyl lithium (2.5M, 3.88 mL, 9.7 mmol) was added dropwise to a solution of diisopropylamine (1.43 mL, 10.13 mmol) in THF (20 mL) at −78° C. under nitrogen, warmed to 0° C., stirred for 30 minutes then re-cooled to −78° C. This was then added to a solution of 3-chloropyridine (0.83 mL, 8.81 mmol) in THF (12 mL) and stirred for 1.5 hours. 3-Oxo-8-aza-bicyclo[3.2.1]octane-8-carboxylic acid tert-butyl ester (1.98 g, 8.81 mmol) in THF (12 mL) was added, the reaction mixture warmed to room temperature for 1.5 hours. Saturated aqueous ammonium chloride and ethyl acetate were added, the organics separated, washed with more saturated aqueous ammonium chloride and brine, dried over magnesium sulphate, filtered and the solvent removed by evaporation under vacuum. The residue was purified by flash chromatography on silica eluting with 0-100% ethyl acetate/pentane. The fractions containing the desired product were concentrated under vacuum to give the title compound (0.34 g). 1H NMR (400 MHz, CDCl3): δ 8.48 (s, 1H), 8.47 (d, 1H), 7.69 (d, 1H), 4.38 (m, broad, 2H), 3.05-2.80 (m, broad, 2H), 2.28-2.0 (broad, 5H), 1.6-1.5 (m, broad, 2H), 1.49 (s, 9H).

Synthesis 30

3-(3-Chloro-pyridin-4-yl)-8-aza-bicyclo[3.2.1]octan-3-ol

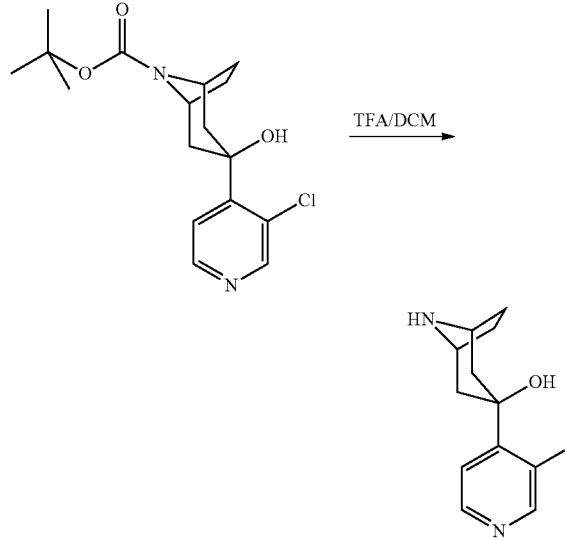

3-(3-Chloro-pyridin-4-yl)-3-hydroxy-8-aza-bicyclo [3.2.1]octane-8-carboxylic acid tert-butyl ester (0.34 g, 1.0 mmol) was dissolved in TFA (1 mL) and DCM (2 mL). The mixture was stirred for 1 hour and the solvent removed by evaporation under vacuum and the residues were passed through an SCX cartridge, eluting with 2 M ammonia in methanol to give the title compound (0.24 g, 1.0 mmol). $^1$H NMR (400 MHz, CDCl$_3$): δ 8.49 (s, 1H), 8.46 (d, 1H), 7.66 (d, 1H), 3.74 (m, broad, 2H), 2.79-2.71 (m, broad, 2H), 2.25-2.17 (m, broad, 3H), 1.98-1.85 (m, broad, 3H), 1.70-1.62 (m, broad, 2H).

Synthesis 31

3-Hydroxy-3-pyrimidin-5-yl-8-aza-bicyclo[3.2.1] octane-8-carboxylic acid tert-butyl ester

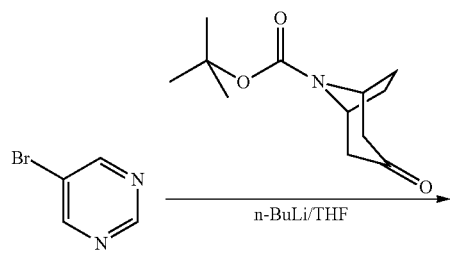

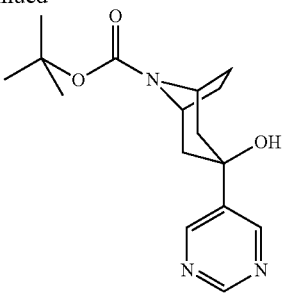

n-Butyl lithium (2.5 M, 1.8 mL, 4.5 mmol) was added dropwise to a solution of 5-bromopyrimidine (0.668 g, 4.2 mmol) in THF (10 mL), under nitrogen at −78° C. and stirred for 1 hour. 3-Oxo-8-aza-bicyclo[3.2.1]octane-8-carboxylic acid tert-butyl ester (0.675 g, 3.0 mmol) in THF (5 mL) was added dropwise at −78° C. and the reaction mixture warmed to room temperature over 1 hour. Saturated aqueous ammonium chloride and ethyl acetate were added, the organics separated, dried over magnesium sulphate, filtered and the solvent removed by evaporation under vacuum. The residue was purified by flash chromatography on silica eluting with 10% methanol/ethyl acetate. The fractions containing the desired product were concentrated under vacuum to give the title compound (0.14 g). LCMS m/z 306 [M+H]$^+$. R.T.=2.89 min (Analytical Method 3).

Synthesis 32

3-Pyrimidin-5-yl-8-aza-bicyclo[3.2.1]octan-3-ol hydrochloride

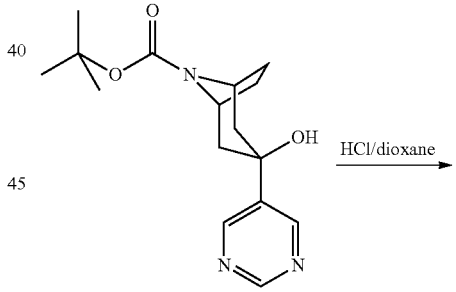

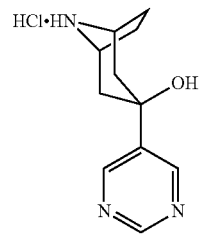

3-Hydroxy-3-pyrimidin-5-yl-8-aza-bicyclo[3.2.1]octane-8-carboxylic acid tert-butyl ester (0.14 g, 0.46 mmol) was dissolved in a solution of hydrogen chloride in dioxane (4 N, 1.5 mL). The mixture was stirred for 1 hour at 45° C., DCM (3 mL) added and stirred for 5 minutes. The solvent was removed by evaporation under vacuum afford the title compound. LCMS m/z 206.3 [M+H]$^+$. R.T.=2.90 min (Analytical Method 3).

Synthesis 33

[3-(3-Chloro-pyridin-2-yl)-3-fluoro-8-aza-bicyclo[3.2.1]oct-8-yl]-[5-(1H-pyrazol-4-yl)-thiophen-3-yl]-methanone (PA Mixture) (XX-13)

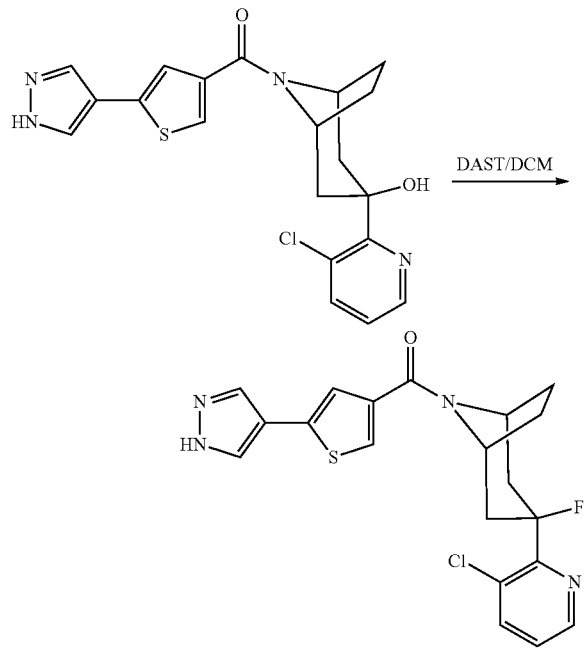

[3-(3-Chloro-pyridin-2-yl)-3-hydroxy-8-aza-bicyclo[3.2.1]oct-8-yl]-[5-(1H-pyrazol-4-yl)-thiophen-3-yl]-methanone (0.17 g, 0.41 mmol) in DCM (4 mL) was cooled to −78° C., under nitrogen, DAST (0.216 mL, 1.64 mmol) added and the reaction mixture stirred for 1 hour. Saturated aqueous sodium hydrogen carbonate and DCM were added, the organics separated, dried over sodium sulphate, filtered and the solvent removed by evaporation under vacuum. The residue was purified by flash chromatography on silica eluting with 1-6% methanol/DCM. Then further purified by HPLC on a C18 cartridge, eluting with 5%-98% methanol/water with 0.1% formic acid. The fractions containing the desired product were concentrated under vacuum to give the title compound as a white solid (0.07 g). LCMS m/z 418.9 [M+H]⁺. R.T.=4.05/4.14 min (Analytical Method 1).

Synthesis 34

(3-Fluoro-3-thiazol-2-yl-8-aza-bicyclo[3.2.1]oct-8-yl)-[5-(1H-pyrazol-4-yl)-thiophen-3-yl]-methanone (PA Isomer 1 (XX-34)

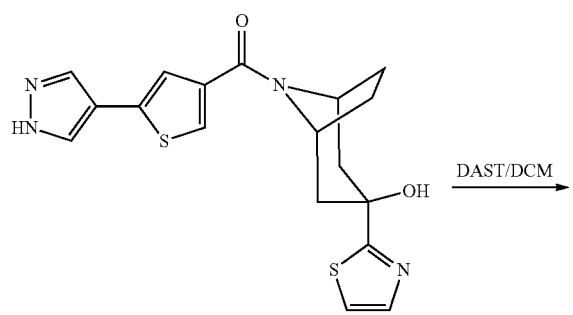

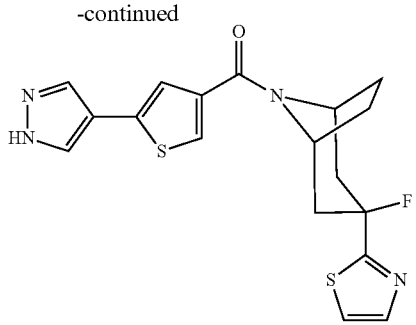

(3-Hydroxy-3-thiazol-2-yl-8-aza-bicyclo[3.2.1]oct-8-yl)-[5-(1H-pyrazol-4-yl)-thiophen-3-yl]-methanone (0.09 g, 0.23 mmol) in DCM (30 mL) was cooled to −78° C., under nitrogen. DAST (0.04 mL, 0.3 mmol) was added and the reaction mixture stirred for 1 hour. Saturated aqueous sodium hydrogen carbonate and DCM were added, the organics separated, washed with brine, dried over magnesium sulphate, filtered and the solvent removed by evaporation under vacuum. The residues were purified by flash chromatography, eluting with ethyl acetate. The fraction containing the desired product was concentrated under vacuum to give the title compound as a white solid (0.012 g). LCMS m/z 389.1 [M+H]⁺. R.T.=8.05 min (Analytical Method 2).

Synthesis 35

3-Fluoro-3-pyridin-2-yl-8-aza-bicyclo[3.2.1]octane-8-carboxylic acid tert-butyl ester (PA Isomer 1) and 3-Fluoro-3-pyridin-2-yl-8-aza-bicyclo[3.2.1]octane-8-carboxylic acid tert-butyl ester (PA Isomer 2)

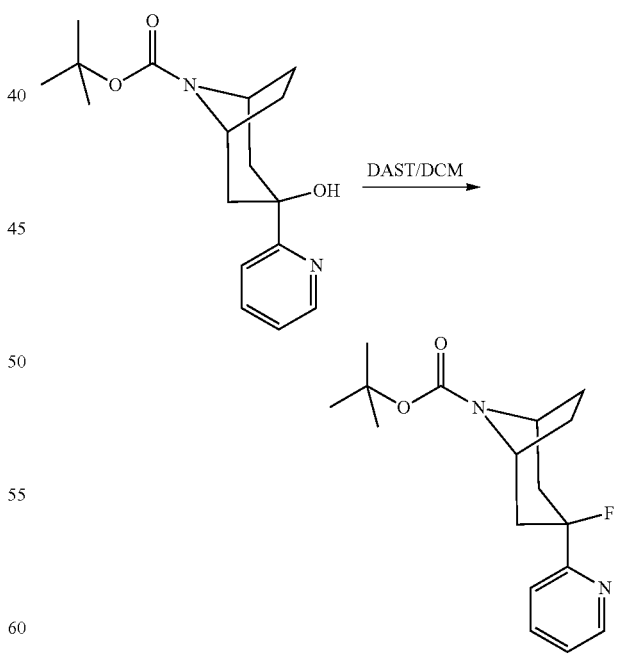

DAST (0.3 mL, 2.26 mmol) was added to DCM (15 mL) and the mixture was cooled to −78° C. under an atmosphere of argon. 3-Hydroxy-3-pyridin-2-yl-8-aza-bicyclo[3.2.1]octane-8-carboxylic acid tert-butyl ester (0.55 g) in DCM (5 mL) was then added and the mixture stirred for 1 hour. Saturated aqueous sodium hydrogen carbonate was added and the products extracted into DCM. The organic solution was washed with brine and dried with magnesium sulphate and then the solvent evaporated under vacuum. The residue was purified by flash chromatography on silica eluting with 0-100% diethylether/pentane. The fractions containing the desired products were concentrated under vacuum to give the title compounds.

PA Isomer 1 (0.056 g): LCMS m/z 307 [M+H]$^+$. R.T.=4.16 min (Analytical Method 3).

PA Isomer 2 (0.127 g): LCMS m/z 307 [M+H]$^+$. R.T.=3.89 min (Analytical Method 3).

Synthesis 36

3-Fluoro-3-pyridin-2-yl-8-aza-bicyclo[3.2.1]octane (PA Isomer 1)

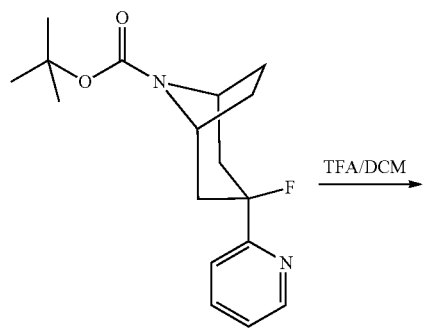

TFA/DCM

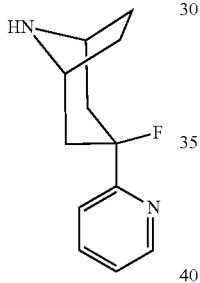

3-Fluoro-3-pyridin-2-yl-8-aza-bicyclo[3.2.1]octane-8-carboxylic acid tert-butyl ester (PA Isomer 1) (0.056 g) was dissolved in DCM (1 mL) and TFA (5 mL). The solution was stirred for 2 hours then the solvent was removed by evaporation under vacuum. The residue was loaded onto an SCX-2 cartridge and washed with DCM, methanol and then eluted with ammonia (2 M in methanol). The solvent was removed by evaporation under vacuum to afford the title compound as a white solid (0.032 g). LCMS m/z 207 [M+H]$^+$. R.T.=0.37 min (Analytical Method 3).

The following substituted piperidines were made by methods analogous to those used to prepare 3-fluoro-3-pyridin-2-yl-8-aza-bicyclo[3.2.1]octane PA Isomer 1:

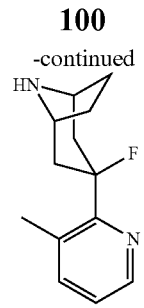

3-Fluoro-3-pyridin-2-yl-8-aza-bicyclo[3.2.1]octane
PA Isomer 2

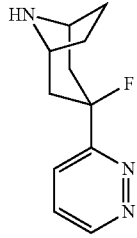

3-Fluoro-3-(3-methyl-pyridin-2-yl)-8-aza bicyclo[3.2.1]octane
PA Mixture

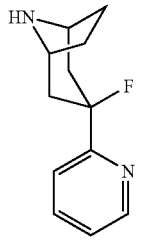

3-Fluoro-3-pyridazin-3-yl-8-aza-bicyclo[3.2.1]octane
PA Isomer 1

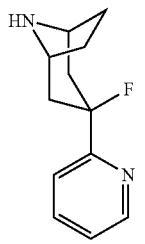

3-Fluoro-3-pyridin-2-yl-8-aza-bicyclo[3.2.1]octane
PA Isomer 1

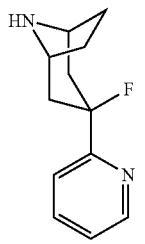

3-Fluoro-3-pyridin-2-yl-8-aza-bicyclo[3.2.1]octane
PA Isomer 2

Synthesis 37

3-Methoxy-3-(3-methyl-pyridin-2-yl)-8-aza-bicyclo[3.2.1]octane hydrochloride

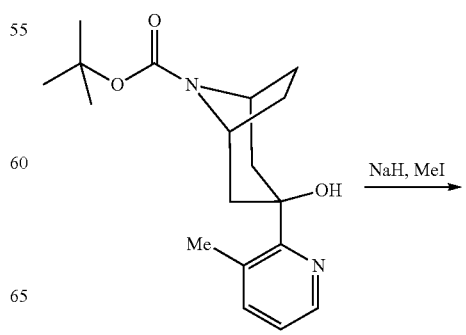

NaH, MeI

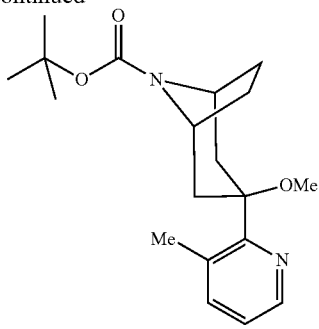

To a solution of 3-hydroxy-3-(3-methyl-pyridin-2-yl)-8-aza-bicyclo[3.2.1]octane-8-carboxylic acid tert-butyl ester (0.4 g) in DMF (12 mL) was added sodium hydride (60% disp. in mineral oil, 0.06 g), and the mixture stirred for 0.5 hours. Methyl iodide (0.125 mL) was added and the mixture stirred for 2 hours. Sodium hydride (60% disp. in mineral oil, 0.06 g) and methyl iodide (0.5 mL) were added and the mixture stirred for 18 hours. Water (70 mL) was added and the mixture extracted with ethyl acetate. The organic solution was dried with anhydrous magnesium sulphate, filtered and the solvent removed by evaporation. The residue was purified by flash chromatography on silica eluting with 25% ethyl acetate/hexane. The fractions containing the desired product were concentrated under vacuum to give the title compound (0.09 g).

Synthesis 38

3-Methoxy-3-(3-methyl-pyridin-2-yl)-8-aza-bicyclo[3.2.1]octane hydrochloride

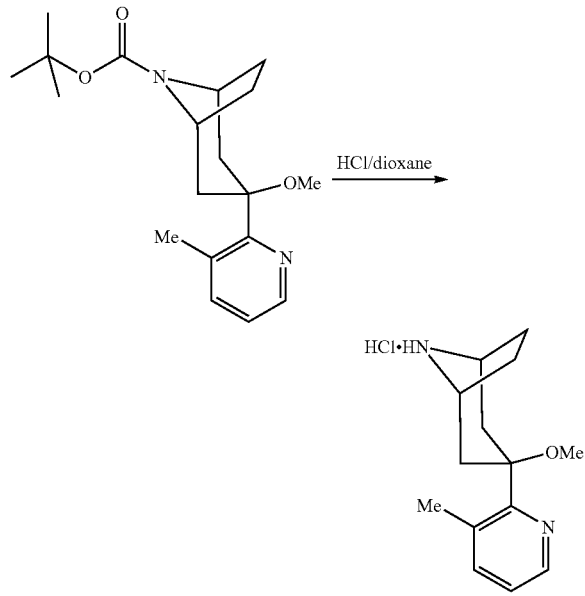

3-Methoxy-3-(3-methyl-pyridin-2-yl)-8-aza-bicyclo[3.2.1]octane-8-carboxylic acid tert-butyl ester (0.09 g) was dissolved in a solution of hydrogen chloride in dioxane (4 N, 1.5 mL). The mixture was stirred for 1 hour at 50° C., DCM (3 mL) added and stirred for 5 minutes. The solvent was removed by evaporation under vacuum afford the title compound as a white solid. LCMS m/z 233.1 [M+H]$^+$. R.T.=1.72 min (Analytical Method 3).

The hydrochloride salts of the following substituted piperidines were made by methods analogous to those used to prepare 3-methoxy-3-(3-methyl-pyridin-2-yl)-8-aza-bicyclo[3.2.1]octane hydrochloride:

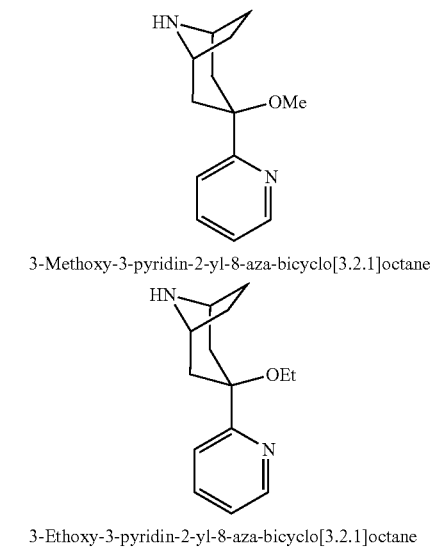

3-Methoxy-3-pyridin-2-yl-8-aza-bicyclo[3.2.1]octane

3-Ethoxy-3-pyridin-2-yl-8-aza-bicyclo[3.2.1]octane

Synthesis 39

3-Cyano-3-thiazol-2-yl-8-aza-bicyclo[3.2.1]octane-8-carboxylic acid tert-butyl ester

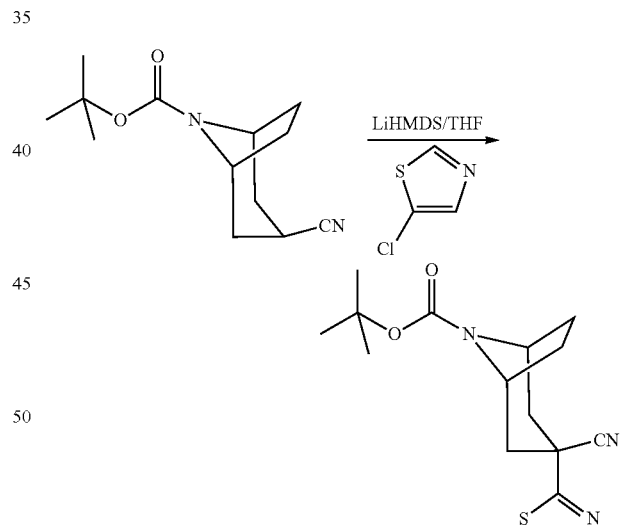

3-Cyano-8-aza-bicyclo[3.2.1]octane-8-carboxylic acid tert-butyl ester (0.15 g) and 2-chloro-1,3-thiazole (0.09 g, 0.75 mmol) were dissolved in THF (4 mL). The mixture was cooled to −78° C. and lithium HMDS (1 M in THF; 0.89 mL) was added dropwise. After 5 minutes, the mixture was allowed to warm to room temperature and after 0.5 hour saturated aqueous ammonium chloride was added and the products extracted into ethyl acetate. The organic solution was dried with anhydrous magnesium sulphate, filtered and the solvent removed by evaporation. The residue was purified by flash chromatography on silica eluting with 30% ethyl acetate/hexane. The fractions containing the desired product were concentrated under vacuum to give the title compound (0.2 g).

Synthesis 40

3-Thiazol-2-yl-8-aza-bicyclo[3.2.1]octane-3-carbonitrile hydrochloride

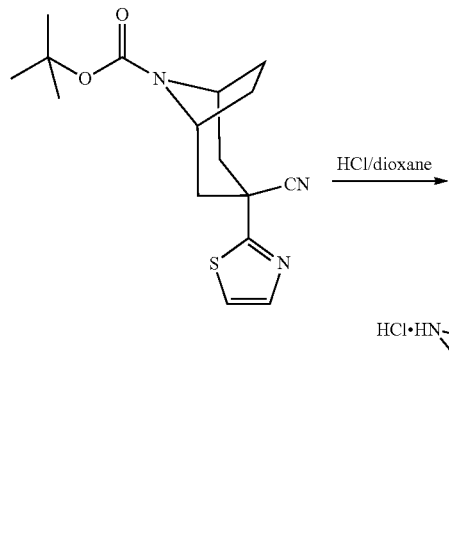

3-Cyano-3-thiazol-2-yl-8-aza-bicyclo[3.2.1]octane-8-carboxylic acid tert-butyl ester (0.2 g) was dissolved in a solution of hydrogen chloride in dioxane (4 N, 3 mL). The mixture was stirred for 1 hour at 40° C. The solvent was removed by evaporation under vacuum afford the title compound as a white solid. LCMS m/z 220.1 [M+H]$^+$. R.T.=0.58 min (Analytical Method 3).

The hydrochloride salts of the following substituted piperidines were made by methods analogous to those used to prepare 3-thiazol-2-yl-8-aza-bicyclo[3.2.1]octane-3-carbonitrile hydrochloride:

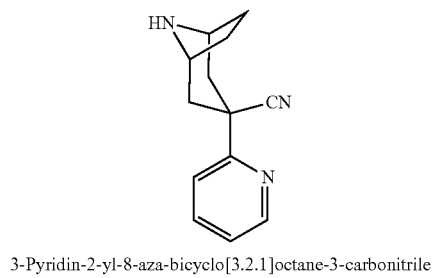

3-Pyridin-2-yl-8-aza-bicyclo[3.2.1]octane-3-carbonitrile 3-(3-Methyl-pyridin-2-yl)-8-aza-bicyclo[3.2.1]octane-3-carbonitrile

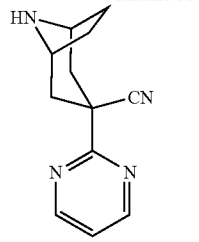

3-Pyrimidin-2-yl-8-aza-bicyclo[3.2.1]octane-3-carbonitrile

Synthesis 41

3-Chloro-4'-hydroxy-3',4',5',6'-tetrahydro-2'H-[2,4']bipyridinyl-1'-carboxylic acid tert-butyl ester

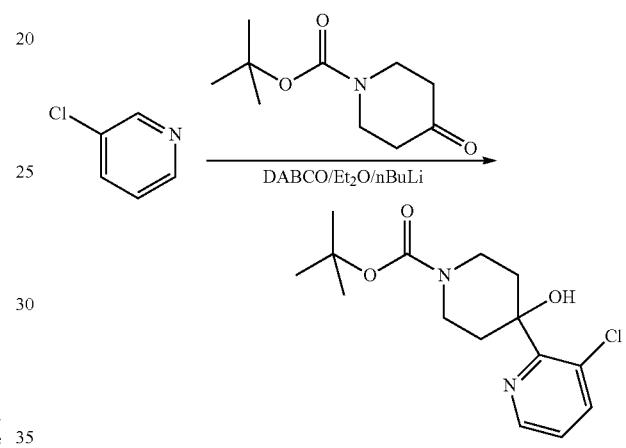

DABCO (0.31 g, 2.75 mmol) in diethyl ether (11 mL) was cooled to −40° C., under nitrogen. n-Butyl lithium (2.5 M, 1.0 mL, 2.5 mmol) was added dropwise and stirred for 30 minutes. The temperature was decreased to −65° C., 3-chloropyridine (0.284 mL, 2.5 mmol) was slowly added and stirred for 30 minutes before a solution of 4-oxo-piperidine-1-carboxylic acid tert-butyl ester (0.5 g, 2.5 mmol) in diethyl ether (5 mL) was added for 30 minutes. Ammonium chloride was added and the mixture extracted into ethyl acetate, dried over sodium sulphate, filtered and the solvent removed by evaporation under vacuum. The residue was purified by flash chromatography on silica eluting with 20% ethyl acetate/cyclohexane. The fractions containing the desired product were concentrated under vacuum to give the title compound (0.18 g). LCMS m/z 313.3 [M+H]$^+$. R.T.=4.51 min (Analytical Method 3).

Synthesis 42

3-Chloro-2',3',5',6'-tetrahydro-1'H-[2,4']bipyridinyl-4'-ol hydrochloride

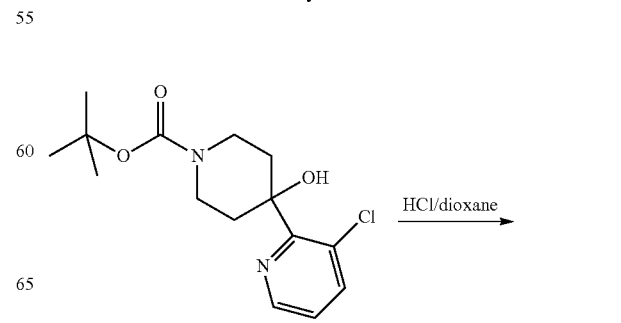

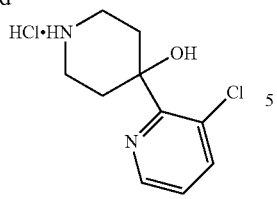

3-Chloro-4'-hydroxy-3',4',5',6'-tetrahydro-2'H-[2,4']bipyridinyl-1'-carboxylic acid tert-butyl ester (0.18 g) was dissolved in a solution of hydrogen chloride in dioxane (4 N, 2 mL). The mixture was stirred for 0.5 hours and the solvent removed by evaporation under vacuum. The solid was triturated from ether to afford the title compound (0.15 g). LCMS m/z 213.1 [M+H]$^+$. R.T.=0.79 min (Analytical Method 3).

The hydrochloride of the following substituted piperidine was made by methods analogous to those used to prepare 3-chloro-2',3',5',6'-tetrahydro-1'H-[2,4']bipyridinyl-4'-ol hydrochloride:

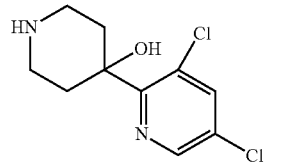

3,5-Dichloro-2',3',5',6'-tetrahydro-1'H-[2,4']bipyridinyl-4'-ol

Synthesis 43

3-Chloro-4'-fluoro-3',4',5',6'-tetrahydro-2'H-[2,4']bipyridinyl-1'-carboxylic acid tert-butyl ester

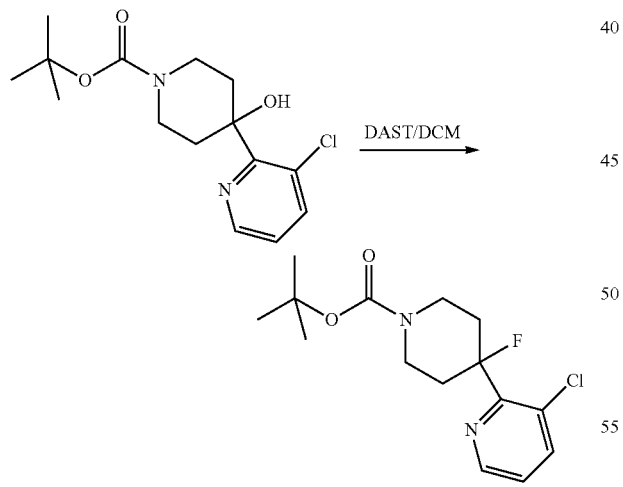

To a solution of DAST (0.837 mL, 6.3 mmol) in DCM (20 mL) at −78° C. a solution of 3-chloro-4'-hydroxy-3',4',5',6'-tetrahydro-2'H-[2,4']bipyridinyl-1'-carboxylic acid tert-butyl ester (1.8 g, 5.8 mmol) in DCM (50 mL) was slowly added and allowed to warm to room temperature. Further DAST (0.6 mL) was added at 0° C. and stirred at room temperature for 30 minutes. Sodium hydrogen carbonate (sat. aq.) and DCM were added, the organics separated, dried over magnesium sulphate, filtered and the solvent removed by evaporation under vacuum. The residue was purified by flash chromatography on silica eluting with 20% ethyl acetate/cyclohexane. The fractions containing the desired product were concentrated under vacuum to give the title compound as a white solid (0.13 g).

Synthesis 44

3-Chloro-4'-fluoro-2',3',5',6'-tetrahydro-1'H-[2,4']bipyridinyl hydrochloride

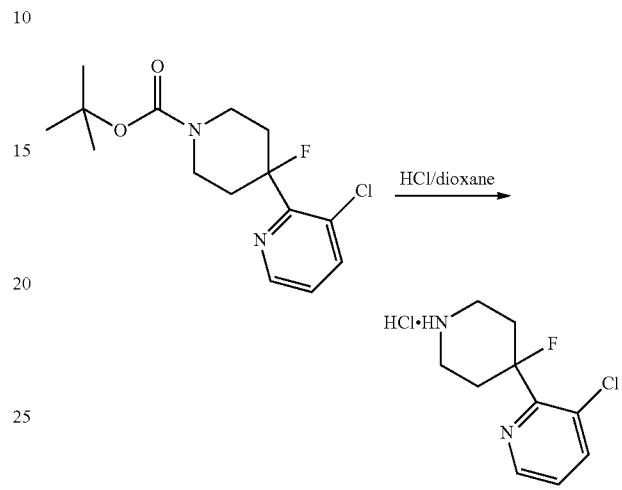

3-Chloro-4'-fluoro-3',4',5',6'-tetrahydro-2'H-[2,4']bipyridinyl-1'-carboxylic acid tert-butyl ester (0.13 g, 0.41 mmol) was dissolved in a solution of hydrogen chloride in dioxane (4 N, 2 mL). The mixture was stirred for 30 minutes and the solvent removed by evaporation under vacuum. The solid was triturated from ether to afford the title compound (0.10 g). LCMS m/z 215.28 [M+H]$^+$. R.T.=1.87 min (Analytical Method 3).

The hydrochloride salt of the following substituted piperidine was made by methods analogous to those used to prepare 3-chloro-4'-fluoro-2',3',5',6'-tetrahydro-1'H-[2,4']bipyridinyl hydrochloride:

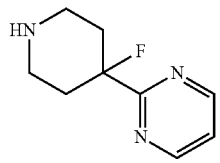

2-(4-Fluoro-piperidin-4-yl)-pyrimidine

Synthesis 45

3,6-Dichloro-4'-hydroxy-3',4',5',6'-tetrahydro-2'H[2,4']bipyridinyl-1'-carboxylic acid tert-butyl ester

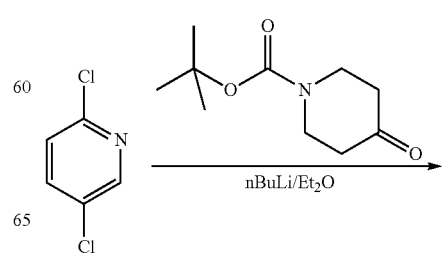

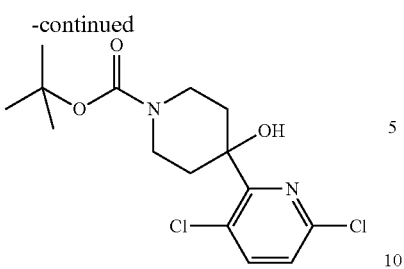

n-Butyl lithium (1.7M, 1 mL) was added dropwise to a solution of 2,5-dichloro-pyridine (2.0 g, 13.57 mmol) in diethyl ether (20 mL), under nitrogen at −78° C. and stirred for 1 hour. 4-Oxo-piperidine-1-carboxylic acid tert-butyl ester (2.69 g, 13.57 mmol) in diethyl ether (5 mL) was added dropwise at −78° C. and the reaction mixture stirred for 0.5 hours before warming to room temperature. A solution of saturated aqueous ammonium chloride was added and the mixture extracted into ethyl acetate. The organics washed with brine, dried over sodium sulphate, filtered and the solvent removed by evaporation under vacuum. The residue was purified by flash chromatography on silica eluting with 5-20% ethyl acetate/cyclohexane. The fractions containing the desired product were concentrated under vacuum to give the title compound (1.44 g).

Synthesis 46

3-Chloro-6-ethyl-4'-hydroxy-3',4',5',6'-tetrahydro-2'H[2,4']bipyridinyl-1'-carboxylic acid tert-butyl ester

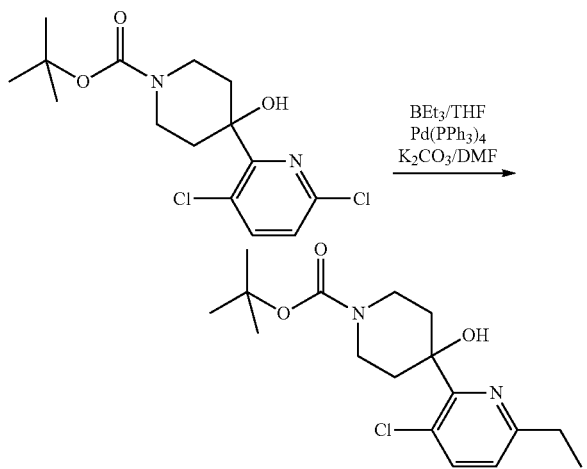

Tetrakis-triphenylphosphine (0.083 g, 0.072 mmol) was added to a solution of 3,6-dichloro-4'-hydroxy-3',4',5',6'-tetrahydro-2'H[2,4']bipyridinyl-1'-carboxylic acid tert-butyl ester (0.25 g, 0.72 mmol) and potassium carbonate (0.2 g, 1.44 mmol) in DMF (4 mL). Triethylborane in THF (1 M, 0.79 mL, 0.79 mmol) was added via syringe under a nitrogen atmosphere and the reaction heated by microwave at 150° C. for 20 minutes. The reaction mixture was then cooled, filtered through celite and partitioned between DCM and water. The organics were separated, washed with 15% lithium chloride, dried over sodium sulphate, filtered and the solvent removed by evaporation under vacuum. The residue was purified by flash chromatography on silica eluting with 5-10% ethyl acetate/cyclohexane. The fractions containing the desired product were concentrated under vacuum to give the title compound (0.086 g). LCMS m/z 241.3 [M+H]$^+$. R.T.=5.20 min (Analytical Method 3).

Synthesis 47

3-Chloro-6-ethyl-2',3',5',6'-tetrahydro-1'H[2,4']bipyridinyl-4'-ol

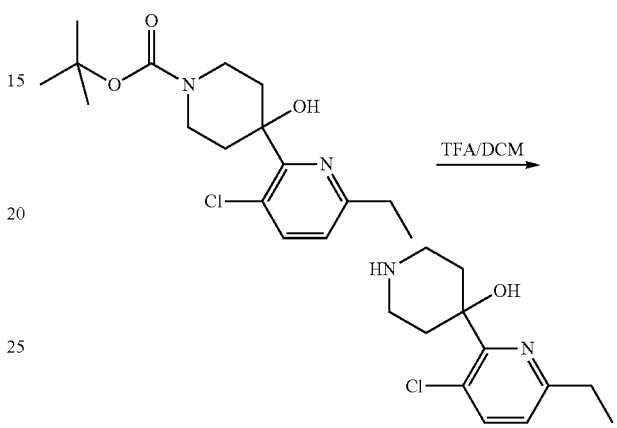

3-Chloro-6-ethyl-4'-hydroxy-3',4',5',6'-tetrahydro-2'H[2,4']bipyridinyl-1'-carboxylic acid tert-butyl ester (0.086 g, 0.25 mmol) was dissolved in TFA (1 mL) and DCM (1 mL). The mixture was stirred for 20 minutes and the solvent removed by evaporation under vacuum and the residues were passed through an SCX cartridge, eluting with 2 M ammonia in methanol to give the title compound (0.052 g). LCMS m/z 243.25 [M+H]$^+$. R.T.=2.45 min (Analytical Method 3).

Biological Methods

Cellular In Vitro 11β-HSD1 Enzyme Inhibition Assay

Compounds were assessed by a Scintillation Proximity Assay (SPA) performed according to the following protocol:

HEK293 cells were stably transfected with a construct containing the full-length gene coding for the human 11β-HSD1 enzyme to create HEK293/11β-HSD1 cells. Cells were routinely cultured in DMEM containing 10% calf foetal serum, 1% glutamine, and 1% penicillin and streptomycin. Prior to assay, cells were plated at $2\times10^4$ cells/well in 96-well poly-D-Lys coated flat-bottomed microplates and incubated in 5% $CO_2$, 95% $O_2$ at 37° C. for 24 hours. The media in each well was removed immediately before assay.

Compounds to be tested were dissolved in DMSO at 10 mM and serially diluted into water containing 10% DMSO. Diluted compounds at a volume of 10 μL were added to wells of a 96-well V-bottomed microplate. A solution of DMEM, 1% glutamine, 1% penicillin and streptomycin, and 22 nM tritiated cortisone was prepared and 90 μL added to each well of the assay plate. This solution (100 μL/well) was transferred to the plate containing the cells. The plate was then incubated in 5% $CO_2$, 95% $O_2$ at 37° C. for 2 hours.

Following this incubation, 50 μL of the assay solution was transferred to each well of a 96-well scintillation microplate. A mixture consisting of anti-mouse YSi SPA beads, pre-mixed with anti-cortisol antibody in assay buffer (50 mM Tris.HCl, pH 7.0; 300 mM NaCl; 1 mM EDTA, 5% glycerol) was prepared and 50 μL added to each well of the scintillation microplate. An adhesive strip was applied to the microplate and the plate gently shaken for at least 2 hours at room temperature, and then spun briefly on a low speed centrifuge. The plate was read on a scintillation counter suitable for 96-well microplates. For the calculation of percentage inhibition, a series of wells were added to the plate that represented the assay maximum and the assay minimum: one set that contained substrate without cells (minimum) and another set that contained substrate and cells without any compound (maximum).

The calculation of median inhibitory concentration ($IC_{50}$) values for the compounds was performed using GraphPad Prism® software. Dose-response curves for each compound were plotted as fractional inhibition and data fitted to the four parameter logistic equation.

Cellular In Vitro 11β-HSD2 Enzyme Inhibition Assay

For measurement of inhibition of 11β-HSD2, CHO cells stably transfected with the full-length gene coding for human 11β-HSD2 were used. Assays were carried out in 96-well microplates containing $1 \times 10^5$ cells/well. Controls and compounds were plated as above, so that the final DMSO concentration in each well was 1%. To initiate the assay, 90 µL of a solution of HAMS F-12 medium containing 1% glutamine, 1% penicillin and streptomycin, and 22 nM tritiated cortisol was added to each well of the assay plate. The plate was then incubated in 5% $CO_2$, 95% $O_2$ at 37° C. for 16 hours.

The assay solutions were transferred to glass tubes and 20 µL ethyl acetate added to each tube. Each tube was vortexed thoroughly and the upper layer containing the tritiated steroid transferred to a fresh glass tube. The solvent was evaporated by placing the tubes in a heating block at 65° C. under a stream of nitrogen gas. 20 µL ethanol was added to each of the dried samples and vortexed briefly. Each sample was applied to a silica TLC plate and the plate dried. The plate was placed vertically in a glass tank containing 92% chloroform: 8% ethanol and the solvent allowed to rise up the plate. The plate was dried, placed in an imaging cassette, and overlayed with a tritium imaging plate for 1-2 days. The amount of enzyme inhibition in each sample was determined by measuring the intensity of the substrate and product spots using a phospho-imager. $IC_{50}$ values for inhibitors were determined as described above for 11β-HSD1.

In Vitro Human Liver Microsomal Stability Assay

To predict in vivo metabolism of compounds, the stability of compounds incubated with human liver microsomes in vitro was determined. Human liver microsome preparations were stored at −80° C. and thawed on ice prior to use. The thawed microsomes were diluted to a concentration of 2 mg/mL in 50 mM sodium phosphate, pH 7.4. Reference and test compounds were prepared as 10 mM stocks in 100% DMSO and diluted to 1 mM in acetonitrile before use. Each compound was tested in triplicate as follows:

4 µL of test or reference compound was added to a well of a 24-well microplate and 0.5 mL of 4 mM NADPH added. The plate was then transferred to a shaker for 10 minutes at room temperature. 30 µL of the compound/NADPH solution was transferred to the well of a 96-well microplate and incubated at 37° C. for 5 minutes. 30 µL of human liver microsomes (pre-incubated at 37° C. for 5 minutes) was added to the well containing the compound/NADPH solution and the plate incubated for the selected period of time (typically 0 or 30 minutes). The reaction was stopped by adding 60 µL of ice cold 300 µM trichloroacetic acid. The plate was centrifuged at 1000 rpm for 5 minutes at room temperature and the supernatant transferred to the well of a new 96-well V-bottomed microplate for mass spectrometric analysis.

Samples were analyzed by TSQ Quantum Discovery Tandem Mass Spectrometer and Surveyor Liquid Chromatogram (Thermo, Hemel-Hempstead, UK). 10 µL of each sample was injected in a mobile phase consisting of 60%: 40% methanol:5 mM ammonium acetate at a flow rate of 0.5 mL/minute. The column used was a BDS hypersil, C18, 50×2.1 mm with a 5 µm particle size.

Each compound was tuned with a spray voltage of 3000 V and a capillary temperature of 300° C. and values for tube lens, CID and product ions were determined.

The peak area for each compound was measured in triplicate for the 0 and 30 minute samples and the average of each was reported. The percentage remaining after 30 minutes was calculated as the average peak area of the sample after 30 minutes divided by the average peak area at 0 minutes. The RSD was 10% or lower for each compound.

Oral Exposure and Tissue Distribution in Rats

The circulating plasma levels and tissue distribution of certain compounds were determined following oral administration of compound (10 mg/kg) to male Sprague Dawley rats. Rats (n=3 per group) were culled at 1, 4 and 6 hours post dosing and trunk blood and tissues (liver, adipose and brain) excised. Blood samples at 30 minutes and 2 hours post dosing were taken by tail nick from the 4 hour and 6 hour rats respectively.

Compound was triple extracted from plasma (prepared from blood by a high speed centrifugation step) spiked with 1 µg of a standard compound using ethyl acetate. Extracts were dried under nitrogen and re-suspended in 60% methanol/40% ammonium acetate (5 mM).

A known weight of tissue was homogenized in 3 volumes Krebs buffer. Compound was triple extracted with ethyl acetate from the supernatant of a low speed spin spiked with 1 µg of a standard compound. Extracts were dried under nitrogen and re-suspended in 60% methanol/40% ammonium acetate (5 mM).

Samples from plasma and tissue were analyzed by TSQ Quantum Discovery Tandem Mass Spectrometer and Surveyor Liquid Chromatogram (Thermo, Hemel-Hempstead, UK). 10 µL of each sample was injected in a mobile phase consisting of 60%:40% methanol:5 mM ammonium acetate at a flow rate of 0.5 mL/minute. The column used was a BDS hypersil, C18, 50×2.1 mm with a 5 µm particle size.

Each compound was tuned with a spray voltage of 3000 V and a capillary temperature of 300° C. and values for tube lens, CID and product ions were determined.

The peak area for each compound and for the internal standard was determined and the concentration of compound per gram of tissue or mL of plasma was calculated by comparison of the peak area ratio to a standard curve.

Pharmacokinetics in Rat

The pharmacokinetic parameters of certain compounds were determined following intravenous (1 mg/kg) and oral (5 mg/kg) administration to male Sprague Dawley rats. Dosing solution was prepared by mixing each compound with 2% DMSO, 38% PEG-400 and 60% (0.9%) NaCl. Solutions were passed through 0.2 µm filters prior to administration.

Following dosing and at appropriate time points, blood samples were taken from a lateral tail vein and transferred into a tube pre-treated with EDTA. Blood samples were analysed for parent compound by LCMS and the quantity of parent compound remaining determined. Non-compartmental analysis was applied to the data using WinNonlin™ software to determine the pharmacokinetic parameters for each compound.

Biological Data
Cellular In Vitro Enzyme Inhibition Data

The following compounds were tested using the cellular in vitro enzyme inhibition assays described above: XX-01 through XX-43, and YY-01 through YY-11.

All of the compounds tested have an $IC_{50}$ of less than about 10 µM. Most of the compounds have an $IC_{50}$ of less than about 500 nM. Many of the compounds have an $IC_{50}$ of less than about 100 nM.

Generally, the $IC_{50}$ ratio for 11β-HSD2 to 11β-HSD1 is at least about ten or greater, and in most cases is one hundred or greater. For example, data for some of the compounds is shown in the following table.

TABLE 1

In vitro Enzyme Inhibition Data

| Compound No. | $IC_{50}$ for 11β-HSD1 (HEK293) | $IC_{50}$ for 11β-HSD2 (CHO) |
| --- | --- | --- |
| YY-02 | 49 nM (* 41 nM) | >10,000 nM |
| YY-06 | 28 nM | >10,000 nM |
| XX-01 | 21 nM (* 28 nM) | >10,000 nM |
| XX-03 | 12 nM | >10,000 nM |
| XX-07 | 3 nM | >10,000 nM |
| XX-13 | 31 nM | >10,000 nM |
| XX-16 | 9 nM | >10,000 nM |
| XX-18 | 15 nM | >10,000 nM |
| XX-20 | 67 nM (* 42 nM) | >10,000 nM |
| XX-24 | 37 nM | >10,000 nM |
| XX-29 | 33 nM (* 31 nM) | >10,000 nM |
| XX-43 | 47 nM (* 50 nM) | >10,000 nM |

(*) These $IC_{50}$ values represent the average of at least two individual experiments.

The following compounds have an $IC_{50}$ for 11β-HSD1 (HEK293) of less than or equal to 100 nM (0.1 µM): XX-01, XX-03, XX-04, XX-05, XX-06, XX-07, XX-08, XX-09, XX-10, XX-11, XX-12, XX-13, XX-14, XX-15, XX-16, XX-17, XX-18, XX-19, XX-20, XX-23, XX-24, XX-26, XX-27, XX-29, XX-32, XX-33, XX-35, XX-36, XX-37, XX-41, XX-42, XX-43, YY-02 and YY-06.

The following compounds have an $IC_{50}$ for 11β-HSD1 (HEK293) of more than 100 nM (0.1 µM) and less than or equal to 500 nM (0.5 µM): XX-25, XX-30, XX-31, XX-34, XX-39, XX-40, YY-03, YY-04, YY-05, YY-07 and YY-09.

The following compounds have an $IC_{50}$ for 11β-HSD1 (HEK293) of more than 500 nM (0.5 µM) and less than or equal to 10 µM: XX-02, XX-21, XX-22, XX-28, XX-38, YY-01, YY-08, YY-10 and YY-11.

Human Liver Microsomal Stability Data

Data for some of the compounds are shown in the following table.

TABLE 2

Human Liver Microsomal Stability Data

| Compound No. | % Parent Remaining at 30 min [a] |
| --- | --- |
| YY-02 | ++ |
| YY-06 | ++ |
| YY-07 | +++ |
| YY-09 | +++ |
| XX-01 | +++ |
| XX-13 | ++ |
| XX-18 | +++ |
| XX-20 | +++ |
| XX-27 | +++ |
| XX-29 | +++ |
| XX-35 | ++ |
| XX-36 | +++ |

TABLE 2-continued

Human Liver Microsomal Stability Data

| Compound No. | % Parent Remaining at 30 min [a] |
| --- | --- |
| XX-37 | +++ |
| XX-43 | +++ |

[a] Parent remaining after 30 minutes: 0-30% +; 31-60% ++; 61-100% +++.

Compounds administered in vivo usually undergo metabolism, which occurs predominantly in the liver and to a lesser extent in the gut. Metabolism of compounds typically generates polar species that are cleared more rapidly from the body than the parent compound. One method of increasing the concentration of a compound in the body is to slow down its metabolism in the liver (and gut) and hence reduce its clearance from the body. If a compound is administered orally and metabolism in the gut wall occurs, slowing the metabolism of a compound may also increase its absorption through the intestine leading to increased oral bioavailability. Increasing the metabolic stability and lowering the clearance of a compound is desirable since it helps to maintain levels of the compound in the body thus prolonging the duration of action of the compound. Incubation of compounds with human liver microsomes is commonly used to predict the metabolism of compounds in vivo. Compounds with high microsomal stability are generally favoured since this often correlates with an improved pharmacokinetic profile in vivo.

The majority of the DSPT compounds tested in human microsomal stability assays have high microsomal stability (61-100% parent compound remaining). Fewer compounds have moderate microsomal stability (31-60% parent compound remaining) and fewer still have low microsomal stability (0-30%).

Rat Pharmacokinetic Data

Data for some of the compounds are shown in the following table:

TABLE 3

Rat Pharmacokinetic Data

| Compound No. | Cl [b] | % F [c] |
| --- | --- | --- |
| XX-20 | + | +++ |
| XX-29 | + | +++ |

[b] Plasma clearance (Cl, mL/min/kg): 0-25 +; 26-50 ++; >51 +++.
[c] % Bioavailability (% F): 0-20 +; 21-40 ++; 41-100 +++.

For the majority of the DSPT compounds tested, the plasma clearance (Cl) is less than 25 mL/min/kg and the bioavailability (% F) is greater than 40%.

Rat Plasma and Tissue Data

Data for some of the compounds are shown in the following table:

TABLE 4

Rat Plasma and Tissue Data

| Compound No. | Plasma $C_{max}$ [d] | Liver $C_{max}$ [e] |
| --- | --- | --- |
| YY-02 | +++ | +++ |
| XX-01 | +++ | ++ |
| XX-20 | +++ | +++ |

TABLE 4-continued

Rat Plasma and Tissue Data

| Compound No. | Plasma $C_{max}^{(d)}$ | Liver $C_{max}^{(e)}$ |
|---|---|---|
| XX-24 | ++ | ++ |
| XX-29 | ++ | ++ |
| XX-36 | +++ | ++ |

$^{(d)}$Maximum Plasma Concentration ($C_{max}$, ng/mL): 0-500 +; 501-1000 ++; >1001 +++.
$^{(e)}$Maximum Liver Concentration ($C_{max}$, ng/g): 0-3000 +, 3001-5000 ++, >5001 +++.

High levels of a compound in plasma are required to maintain its supply to tissues within the body, while high tissue levels are required to maintain inhibition of 11β-HSD1 enzyme in specific tissues such as liver, adipose and brain.

For the majority of DSPT compounds tested, compound is present in liver, adipose and brain tissue; the plasma concentration is greater than 1000 ng/mL; and the concentration in the liver is greater than 3000 ng/g of tissue.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Andrews, R. C., et al., 2003, "Effects of the 11 beta-hydroxysteroid dehydrogenase inhibitor carbenoxolone on insulin sensitivity in men with type 2 diabetes," *J. Clin. Endocrinol. Metab.*, Vol. 88, pp. 285-291.

Christy, C., et al., 2003, "Glucocorticoid action in mouse aorta; localisation of 11β-hydroxysteroid dehydrogenase type 2 and effects on responses to glucocorticoids in vitro," *Hypertension*, Vol. 42, pp. 580-587.

Cooper, M. S., et al., 2000, "Expression and functional consequences of 11β-hydroxysteroid dehydrogenase activity in human bone," *Bone*, Vol. 27, pp. 375-381.

Eckhardt et al., 2010, "Aryl- and Heteroarylcarbonyl derivatives of substituted nortropanes, medicaments containing such compounds and their use", international patent publication number WO 2010/023161 A1 published 4 Mar. 2010.

Eckhardt, M., et al., 2010, "Aryl- and Heteroarylcarbonyl Derivatives of Substituted Nortropanes, Medicaments Containing Such Compounds and Their Use", international patent application publication number WO 2010/023161 A1 published 4 Mar. 2010.

Hadoke, P. W. F., et al., 2001, "Endothelial cell dysfunction in mice after transgenic knockout of type 2, but not type 1, 11β-hydroxysteroid dehydrogenase," *Circulation*, Vol. 104, pp. 2832-2837.

Kotelevtsev, Y. V., et al., 1997, "11β-Hydroxysteroid dehydrogenase type 1 knockout mice show attenuated glucocorticoid inducible responses and resist hyperglycaemia on obesity and stress," *Proc. Natl. Acad. Sci., Vol.* 94, pp. 14924-14929

Masuzaki, H., et al., 2001, "A Transgenic Model of Visceral Obesity and the Metabolic Syndrome," *Science, Vol.* 294, pp. 2166-2170.

Moisan, M. P., et al., 1990, "11 beta-hydroxysteroid dehydrogenase bioactivity and messenger RNA expression in rat forebrain: localization in hypothalamus, hippocampus, and cortex," *Endocrinologqy, Vol.* 127, pp. 1450-1455.

Morton, N. M., et al., 2001, "Improved lipid and lipoprotein profile, hepatic insulin sensitivity, and glucose tolerance in 11β-hydroxysteroid dehydrogenase type 1 null mice," *J. Biol. Chem.*, Vol. 276, pp. 41293-41300.

Morton, N. M., et al., 2004, "Novel adipose tissue-mediated resistance to diet-induced visceral obesity in 11β-hydroxysteroid dehydrogenase type 1 deficient mice," *Diabetes*, Vol. 53, pp. 931-938.

Paterson, J. M., et al., 2004, "Metabolic syndrome without obesity: hepatic overexpression of 11β-hydroxysteroid dehydrogenase type 1 in transgenic mice," *Proc. Natl. Acad. Sci., Vol.* 101, pp. 7088-7093).

Rask, E., et al., 2001, "Tissue-specific dysregulation of cortisol metabolism in human obesity," *J. Clin. Endocrinol. Metab., Vol.* 86, pp. 1418-1421.

Rauz, S., et al., 2001, "Expression and putative role of 11 beta-hydroxysteroid dehydrogenase isozymes within the human eye," *Investigative Opthalmologqy & Visual Science*, Vol. 42, pp. 2037-2042.

Sandeep, T. C., et al., 2004, "11β-hydroxysteroid dehydrogenase inhibition improves cognitive function in healthy elderly men and type 2 diabetics," *Proc. Natl. Acad. Sci., Vol.* 101, pp. 6734-6739.

Seckl, J. R., Walker, B. R., 2001, "11β-Hydroxysteroid dehydrogenase type 1—a tissue-specific amplifier of glucocorticoid action," *Endocrinologqy*, Vol. 142, pp. 1371-1376.

Small, G. R., et al., 2005, "Preventing local regeneration of glucocorticoids by 11β-hydroxysteroid dehydrogenase type 1 enhances angiogenesis," *Proc. Natl. Acad. Sci., Vol.* 102, pp. 12165-12170.

Stimson, R. H., et al., 2010, "Extra-adrenal cortisol production in obese men with type two diabetes mellitus—how big is the therapeutic target for 11βHSD1 inhibitors?" $92^{nd}$ Annual Meeting of the Endocrine Society, San Diego, USA.

Walker, B. R., et al., 1991, "11β-Hydroxysteroid dehydrogenase in vascular smooth muscle and heart: implications for cardiovascular responses to glucocorticoids," *Endocrinology*, Vol. 129, pp. 3305-3312.

Walker, B. R., et al., 1995, "Carbenoxolone increases hepatic insulin sensitivity in man: a novel role for 11-oxosteroid reductase in enhancing glucocorticoid receptor activation," *J. Clin. Endocrinol. Metab.*, Vol. 80, pp. 3155-3139.

Webster et al., 2009, "Amido-thiophene compounds and their use", international patent publication number WO 2009/112845 A1 published 17 Sep. 2009.

Webster, S. P., et al., 2009, "Amido-Thiophene Compounds and Their Use", international patent application publication number WO 2009/112845 A1 published 17 Sep. 1999.

Yau, J. L. W., et al., 2001, "Lack of tissue glucocorticoid reactivation in 11β-hydroxysteroid dehydrogenase type 1

The invention claimed is:

1. A compound of the following formula, or a pharmaceutically acceptable salt thereof:

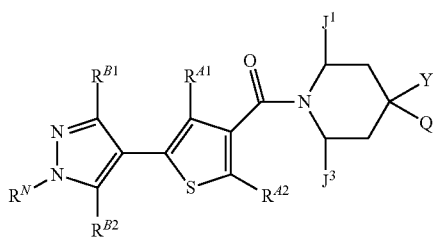

wherein:
-J¹ and -J³ taken together form —CH$_2$CH$_2$—;
-Q is pyrid-2-yl and has n substituents —R$^F$;
n is independently 0 or 1;
each —R$^F$ is independently —R$^Z$, —F, —Cl, —CF$_3$, —OH, —OR$^Z$, —OCF$_3$, —NH$_2$, —NHR$^{ZZ}$, or —NR$^{ZZ}$$_2$;
each —R$^Z$ is independently unsubstituted saturated aliphatic C$_{1-4}$ alkyl;
each —R$^{ZZ}$ is independently saturated aliphatic C$_{1-4}$ alkyl;
—Y is independently —OH, —F, or —CN;
—R$^{A1}$ is independently —H or —R$^{AA}$;
—R$^{A2}$ is independently —H or —R$^{AA}$;
each —R$^{AA}$ is —R$^{AA1}$;
each —R$^{AA1}$ is independently unsubstituted saturated aliphatic C$_{1-4}$ alkyl;
—R$^{B1}$ is independently —H or —R$^{BB}$;
—R$^{B2}$ is independently —H or —R$^{BB}$;
each —R$^{BB}$ is —R$^{BB1}$;
each —R$^{BB1}$ is independently unsubstituted saturated aliphatic C$_{1-4}$ alkyl;
—R$^N$ is independently —H or —R$^{NN}$; and
each —R$^{NN}$ is independently saturated aliphatic C$_{1-4}$ alkyl.

2. A compound according to claim 1, wherein —R$^{A1}$ is —H; and —R$^{A2}$ is —H.
3. A compound according to claim 1, wherein —R$^{B1}$ is —H; and —R$^{B2}$ is —H.
4. A compound according to claim 2, wherein —R$^{B1}$ is —H; and —R$^{B2}$ is —H.
5. A compound according to claim 1, wherein —R$^N$ is —H.
6. A compound according to claim 2, wherein —R$^N$ is —H.
7. A compound according to claim 3, wherein —R$^N$ is —H.
8. A compound according to claim 4, wherein —R$^N$ is —H.
9. A compound according to claim 1, wherein each —R$^Z$ is -Me; and each —R$^{ZZ}$ is -Me.
10. A compound according to claim 2, wherein each —R$^Z$ is -Me; and each —R$^{ZZ}$ is -Me.
11. A compound according to claim 3, wherein each —R$^Z$ is -Me; and each —R$^{ZZ}$ is -Me.
12. A compound according to claim 4, wherein each —R$^Z$ is -Me; and each —R$^{ZZ}$ is -Me.
13. A compound according to claim 5, wherein each —R$^Z$ is -Me; and each —R$^{ZZ}$ is -Me.
14. A compound according to claim 6, wherein each —R$^Z$ is -Me; and each —R$^{ZZ}$ is -Me.
15. A compound according to claim 7, wherein each —R$^Z$ is -Me; and each —R$^{ZZ}$ is -Me.
16. A compound according to claim 8, wherein each —R$^Z$ is -Me; and each —R$^{ZZ}$ is -Me.
17. A compound according to claim 1, wherein n is 0.
18. A compound according to claim 2, wherein n is 0.
19. A compound according to claim 3, wherein n is 0.
20. A compound according to claim 4, wherein n is 0.
21. A compound according to claim 5, wherein n is 0.
22. A compound according to claim 6, wherein n is 0.
23. A compound according to claim 7, wherein n is 0.
24. A compound according to claim 8, wherein n is 0.
25. A compound according to claim 1, wherein Y is —OH.
26. A compound according to claim 8, wherein Y is —OH.
27. A compound according to claim 16, wherein Y is —OH.
28. A compound according to claim 24, wherein Y is —OH.
29. A compound according to claim 1, wherein Y is —F.
30. A compound according to claim 8, wherein Y is —F.
31. A compound according to claim 16, wherein Y is —F.
32. A compound according to claim 24, wherein Y is —F.
33. A compound according to claim 1, wherein Y is —CN.
34. A compound according to claim 8, wherein Y is —CN.
35. A compound according to claim 16, wherein Y is —CN.
36. A compound according to claim 24, wherein Y is —CN.
37. A compound according to claim 27, wherein —Y and the —CH$_2$CH$_2$— bridge are positioned on the same face of the piperidine ring.
38. A compound according to claim 28, wherein —Y and the —CH$_2$CH$_2$— bridge are positioned on the same face of the piperidine ring.
39. A compound according to claim 31, wherein —Y and the —CH$_2$CH$_2$— bridge are positioned on the same face of the piperidine ring.
40. A compound according to claim 32, wherein —Y and the —CH$_2$CH$_2$— bridge are positioned on the same face of the piperidine ring.
41. A compound according to claim 35, wherein —Y and the —CH$_2$CH$_2$— bridge are positioned on the same face of the piperidine ring.
42. A compound according to claim 36, wherein —Y and the —CH$_2$CH$_2$— bridge are positioned on the same face of the piperidine ring.
43. A compound according to claim 27, wherein —Y and the —CH$_2$CH$_2$— bridge are positioned on opposite faces of the piperidine ring.
44. A compound according to claim 28, wherein —Y and the —CH$_2$CH$_2$— bridge are positioned on opposite faces of the piperidine ring.
45. A compound according to claim 31, wherein —Y and the —CH$_2$CH$_2$— bridge are positioned on opposite faces of the piperidine ring.
46. A compound according to claim 32, wherein —Y and the —CH$_2$CH$_2$— bridge are positioned on opposite faces of the piperidine ring.
47. A compound according to claim 35, wherein —Y and the —CH$_2$CH$_2$— bridge are positioned on opposite faces of the piperidine ring.
48. A compound according to claim 36, wherein —Y and the —CH$_2$CH$_2$— bridge are positioned on opposite faces of the piperidine ring.

49. A pharmaceutical composition comprising a compound according to claim 1 or a pharmaceutically acceptable salt thereof, and a pharmaceutically acceptable carrier or diluent.

50. A method of preparing a pharmaceutical composition comprising the step of admixing a compound according to claim 1 or a pharmaceutically acceptable salt thereof, and a pharmaceutically acceptable carrier or diluent.

* * * * *